United States Patent [19]
Mabilat et al.

[11] Patent Number: 5,976,791
[45] Date of Patent: Nov. 2, 1999

[54] NUCLEOTIDE FRAGMENTS CAPABLE OF HYBRIDIZING SPECIFICALLY TO RICKETTSIA RDNA OR RRNA AND THEIR USE AS PROBES OR PRIMERS

[75] Inventors: Claude Mabilat, Rilleux la Pape; Didier Raoult, Marseilles, both of France

[73] Assignee: Bio Merieux, Marcy l'Etoile, France

[21] Appl. No.: 08/632,470

[22] PCT Filed: Aug. 24, 1995

[86] PCT No.: PCT/FR95/01114

§ 371 Date: Jul. 8, 1996

§ 102(e) Date: Jul. 8, 1996

[87] PCT Pub. No.: WO96/06186

PCT Pub. Date: Feb. 29, 1996

[30] Foreign Application Priority Data

Aug. 24, 1994 [FR] France ................................ 94 10263

[51] Int. Cl.⁶ .............................. C12Q 1/68; C07H 21/02; C07H 21/04; C12N 15/00
[52] U.S. Cl. ............................ 435/6; 536/23.1; 536/24.3; 935/76; 935/77; 935/78
[58] Field of Search ................................ 435/6; 536/23.1, 536/24.3

[56] References Cited

FOREIGN PATENT DOCUMENTS 0425217  5/1991  European Pat. Off. .

OTHER PUBLICATIONS

Gray et al. "On the Evolutionary Descent of Organisms and Organelles: a Global Phylogeny Based on a Highly Conserved Structural Core in Small Subunit Ribosomal RNA." *Nucleic Acids Research*, vol. 12, pp. 5837–5852, 1984.
Woese et al. "Detailed Analysis of the Higher–Order Structure of 16S–Like Ribosomal Ribonucleic Acids." *Microbiology Reviews*, vol. 47, No. 4, pp. 621–669, Dec. 1983.
Pang et al., J. of Bacteriology 175(12): 3893–3896 (1993).
Sexton et al., Am. J. Trop. Med. Hyg. 50(1): 59–63 (1994).
Roux et al., Res. Microbiol. 146: 385–396 (1995).
Matthews et al., Analytical Biochemistry 169 : pp. 1–25 (1988).
Friedmann, T., Nature Medicine 2(2) : 144–147 (Feb. 1996).
Marshall, E., Science 269 : 1050–1055 (Aug. 1995).
Kenneth H. Wilson et al., "Probe Directed at a Segment of *Rickettsia rickettsii* rRNA Amplified with Polymerase Chain Reaction", *Journal of Clinical Microbiology*, pp. 2692–2696, Dec. 1989.
Martin E. Schriefer et al., "Identification of a Novel Rickettsial Infection in a Patient Diagnosed with Murine Typhus", *Journal of Clinical Microbiology*, pp. 949–954, Apr. 1994.
Kenneth H. Wilson et al., "Amplification of Bacterial 16S Ribosomal DNA with Polymerase Chain Reaction", *Journal of Clinical Microbiology*, pp. 1942–1946, Sep. 1990.
Gary J. Olsen et al. "The Ribosomal Database Project", *Nucleic Acids Research*, vol. 20, Supplement pp. 2199–2200, May 11, 1992.
W.G. Weisburg et al., "Phylogenetic Diversity of the Rickettsiae", *Journal of Bacteriology*, pp. 4202–4206, Aug. 1989.
F.J.M. van Kuppeveld et al., "Genus—and Species–Specific Identification of Mycoplasmas by 16S rRNA Amplification", *Applied and Environmental Microbiology*, vol. 58, No. 8, pp. 2606–2615, Aug. 1992.
Y. Yoshida et al., *Chemical Abstracts*, vol. 117, No. 13, p. 218, Abstract No. 125902m, 1992.
K.S. Greisen et al., *Database Geneseq*, Accession No. Q37314, WO 93–03186A, Jun. 20, 1993.
D.E. Schwartz et al., *Database Geneseq*, Accession No. N90449, WO 89–06704A, Nov. 30, 1989.

*Primary Examiner*—W. Gary Jones
*Assistant Examiner*—Ethan Whisenant
*Attorney, Agent, or Firm*—Oliff & Berridge, PLC

[57] ABSTRACT

The invention relates to oligonucleotide primers and probes that can specifically hybridize to the rDNA or rRNA of at least one species of the genus Rickettsia.

27 Claims, No Drawings

SEQUENCE LISTING (1) GENERAL INFORMATION:

(iii) NUMBER OF SEQUENCES: 53

(2) INFORMATION FOR SEQ ID NO:1:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (genomic)

(iv) ANTI-SENSE: NO (vi) ORIGINAL SOURCE:
          (A) ORGANISM: R. tsutsugamushi (viii) POSITION IN GENOME:
          (A) CHROMOSOME/SEGMENT: R. rickettsii
          (B) MAP POSITION: 130-170

(xi) SEQUENCE DESCRIPTION: SEQ ID NO:1:

CGAATTAATG CTGAGTTTGC TTAGTATTAA TTA                              33

(2) INFORMATION FOR SEQ ID NO:2:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(iv) ANTI-SENSE: NO (vi) ORIGINAL SOURCE:
          (A) ORGANISM: R. tsutsugamushi (viii) POSITION IN GENOME:
          (A) CHROMOSOME/SEGMENT: R. rickettsii
          (B) MAP POSITION: 181-201

(xi) SEQUENCE DESCRIPTION: SEQ ID NO:2:

GTGAGTAACA CGTGGGAATC T                                          21

(2) INFORMATION FOR SEQ ID NO:3:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(iv) ANTI-SENSE: NO (vi) ORIGINAL SOURCE:
          (A) ORGANISM: R. tsutsugamushi (viii) POSITION IN GENOME:
          (A) CHROMOSOME/SEGMENT: R. rickettsii
          (B) MAP POSITION: 241-272

(xi) SEQUENCE DESCRIPTION: SEQ ID NO:3:

TACCGTATGC CCTCTATAAG GAGGAAA                                    27

-continued (2) INFORMATION FOR SEQ ID NO:4:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(iv) ANTI-SENSE: NO (vi) ORIGINAL SOURCE:
(A) ORGANISM: R. tsutsugamushi (viii) POSITION IN GENOME:
(A) CHROMOSOME/SEGMENT: R. rickettsii
(B) MAP POSITION: 284-298

(xi) SEQUENCE DESCRIPTION: SEQ ID NO:4:

TATCGCTGAT GGATG 15

(2) INFORMATION FOR SEQ ID NO:5:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(iv) ANTI-SENSE: NO (vi) ORIGINAL SOURCE:
(A) ORGANISM: R. tsutsugamushi (viii) POSITION IN GENOME:
(A) CHROMOSOME/SEGMENT: R. rickettsii
(B) MAP POSITION: 299-315

(xi) SEQUENCE DESCRIPTION: SEQ ID NO:5:

AGCCCGCGGC AGATTAG 17

(2) INFORMATION FOR SEQ ID NO:6:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(iv) ANTI-SENSE: NO (vi) ORIGINAL SOURCE:
(A) ORGANISM: R. tsutsugamushi (viii) POSITION IN GENOME:
(A) CHROMOSOME/SEGMENT: R. rickettsii
(B) MAP POSITION: 334-357

(xi) SEQUENCE DESCRIPTION: SEQ ID NO:6:

GCTTACCAAG CCTGTGATCT GTAG 24

(2) INFORMATION FOR SEQ ID NO:7:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(iv) ANTI-SENSE: NO (vi) ORIGINAL SOURCE:
             (A) ORGANISM: R. tsutsugamushi (viii) POSITION IN GENOME:
             (A) CHROMOSOME/SEGMENT: R. rickettsii
             (B) MAP POSITION: 460-481

(xi) SEQUENCE DESCRIPTION: SEQ ID NO:7:

CCAGCAATGC CGCGTGAGTG AT 22

(2) INFORMATION FOR SEQ ID NO:8:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(iv) ANTI-SENSE: NO (vi) ORIGINAL SOURCE:
(A) ORGANISM: R. tsutsugamushi (viii) POSITION IN GENOME:
(A) CHROMOSOME/SEGMENT: R. rickettsii
(B) MAP POSITION: 504-536

(xi) SEQUENCE DESCRIPTION: SEQ ID NO:8:

TCTTTTAGTA GGGATGATAA T 21

(2) INFORMATION FOR SEQ ID NO:9:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(iv) ANTI-SENSE: NO (vi) ORIGINAL SOURCE:
(A) ORGANISM: R. tsutsugamushi (viii) POSITION IN GENOME:
(A) CHROMOSOME/SEGMENT: R. rickettsii
(B) MAP POSITION: 550-570

(xi) SEQUENCE DESCRIPTION: SEQ ID NO:9:

GACAGTACCT ACAGAAAAAG C 21

(2) INFORMATION FOR SEQ ID NO:10:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(iv) ANTI-SENSE: NO (vi) ORIGINAL SOURCE:
(A) ORGANISM: R. tsutsugamushi (viii) POSITION IN GENOME:

```
    (A) CHROMOSOME/SEGMENT: R. rickettsii
    (B) MAP POSITION: 561-585

(xi) SEQUENCE DESCRIPTION: SEQ ID NO:10:

CAGAAAAAGC CCCGGCTAAC TCCGT                                        25

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: R. tsutsugamushi (viii) POSITION IN GENOME:
        (A) CHROMOSOME/SEGMENT: R. rickettsii
        (B) MAP POSITION: 661-684

(xi) SEQUENCE DESCRIPTION: SEQ ID NO:11:

TAATAAGTTA GGAGTGAAAT CCCA                                         24

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: R. tsutsugamushi (viii) POSITION IN GENOME:
        (A) CHROMOSOME/SEGMENT: R. rickettsii
        (B) MAP POSITION: 710-739

(xi) SEQUENCE DESCRIPTION: SEQ ID NO:12:

AAAACTGTTA GGCTAGAGTA TGGTAGAGGG                                   30

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (vi) ORIGINAL SOURCE:
        (A) ORGANISM: R. tsutsugamushi (viii) POSITION IN GENOME:
        (A) CHROMOSOME/SEGMENT: R. rickettsii
        (B) MAP POSITION: 903-929

(xi) SEQUENCE DESCRIPTION: SEQ ID NO:13:

GATATTGGGG GATTTTTCTT TCA                                          23
```

-continued (2) INFORMATION FOR SEQ ID NO:14:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(iv) ANTI-SENSE: NO (vi) ORIGINAL SOURCE:
(A) ORGANISM: R. tsutsugamushi (viii) POSITION IN GENOME:
(A) CHROMOSOME/SEGMENT: R. rickettsii
(B) MAP POSITION: 940-960

(xi) SEQUENCE DESCRIPTION: SEQ ID NO:14:

TAACGCATTA AGCACTCCGC C 21

(2) INFORMATION FOR SEQ ID NO:15:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(iv) ANTI-SENSE: NO (vi) ORIGINAL SOURCE:
(A) ORGANISM: R. tsutsugamushi (viii) POSITION IN GENOME:
(A) CHROMOSOME/SEGMENT: R. rickettsii
(B) MAP POSITION: 1035-1055

(xi) SEQUENCE DESCRIPTION: SEQ ID NO:15:

AATTCGATGA TCCGCGAAAA A 21

(2) INFORMATION FOR SEQ ID NO:16:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(iv) ANTI-SENSE: NO (vi) ORIGINAL SOURCE:
(A) ORGANISM: R. tsutsugamushi (viii) POSITION IN GENOME:
(A) CHROMOSOME/SEGMENT: R. rickettssii
(B) MAP POSITION: 1078-1107

(xi) SEQUENCE DESCRIPTION: SEQ ID NO:16:

AGTCGCGAAA AATGGAGACA TTTTTCTTCA 30

(2) INFORMATION FOR SEQ ID NO:17:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(iv) ANTI-SENSE: NO (vi) ORIGINAL SOURCE:
            (A) ORGANISM: R. tsutsugamushi (viii) POSITION IN GENOME:
            (A) CHROMOSOME/SEGMENT: R. rickettsii
            (B) MAP POSITION: 1199-1213

(xi) SEQUENCE DESCRIPTION: SEQ ID NO:17:

ATTCTTATTT GCCAG 15

(2) INFORMATION FOR SEQ ID NO:18:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iv) ANTI-SENSE: NO (vi) ORIGINAL SOURCE:
(A) ORGANISM: R. tsutsugamushi (viii) POSITION IN GENOME:
(A) CHROMOSOME/SEGMENT: R. rickettsii
(B) MAP POSITION: 1330-1350

(xi) SEQUENCE DESCRIPTION: SEQ ID NO:18:

CTACAGAGTG ATGCGATACG 20

(2) INFORMATION FOR SEQ ID NO:19:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(iv) ANTI-SENSE: NO (vi) ORIGINAL SOURCE:
(A) ORGANISM: R. tsutsugamushi (viii) POSITION IN GENOME:
(A) CHROMOSOME/SEGMENT: R. rickettsii
(B) MAP POSITION: 1361-1387

(xi) SEQUENCE DESCRIPTION: SEQ ID NO:19:

AGCTAATCAT TAAAAGGTAT CTCAGT 26

(2) INFORMATION FOR SEQ ID NO:20:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (genomic)

(iv) ANTI-SENSE: NO (vi) ORIGINAL SOURCE:
(A) ORGANISM: R. tsutsugamushi (viii) POSITION IN GENOME:

(A) CHROMOSOME/SEGMENT: R. rickettsii
                (B) MAP POSITION: 1429-1463

(xi) SEQUENCE DESCRIPTION: SEQ ID NO:20:

CGCTAGTAAT CGCGGATCAG CATGCCGCGG TGAAT                              35

(2) INFORMATION FOR SEQ ID NO:21:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: DNA (genomic)

(iv) ANTI-SENSE: NO (vi) ORIGINAL SOURCE:
                (A) ORGANISM: R. tsutsugamushi (viii) POSITION IN GENOME:
                (A) CHROMOSOME/SEGMENT: R. rickettsii
                (B) MAP POSITION: 1501-1520

(xi) SEQUENCE DESCRIPTION: SEQ ID NO:21:

TGGGAGTCAG TGGTACCTGA                                               20

(2) INFORMATION FOR SEQ ID NO:22:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (ii) MOLECULE TYPE: DNA (genomic)

(iv) ANTI-SENSE: NO (vi) ORIGINAL SOURCE:
                (A) ORGANISM: R. tsutsugamushi (viii) POSITION IN GENOME:
                (A) CHROMOSOME/SEGMENT: R. rickettsii
                (B) MAP POSITION: 1555-1576

(xi) SEQUENCE DESCRIPTION: SEQ ID NO:22:

CACGGTAGAA CTGGTGACTG GG                                            22

(2) INFORMATION FOR SEQ ID NO:23:

(i) SEQUENCE CHARACTERISTICS:
                (A) LENGTH: 1440 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:23:

CCTGGCTCAG AACGAACGCT ATCGGTATGC TTAACACATG CAAGTCGAAC GGACTAATTG    60

GGGCTTGCTC CAATTAGTTA GTGGCAGACG GGTGAGTAAC ACGTGGGAAT CTACCCATCA   120

GTACGGAATA ACTTTTAGAA ATAAAAGCTA ATACCGTATA TTCTCTGCGG AGGAAAGATT   180

TATCGCTGAT GGATGAGCCC GCGTCAGATT AGGTAGTTGG TGAGGTAATG GCTCACCAAG   240

CCGACGATCT GTAGCTGGTC TGAGAGGATG ATCAGCCACA CTGGGACTGA GACACGGCCC   300

AGACTCCTAC GGGAGGCAGC AGTGGGGAAT ATTGGACAAT GGGCGAAAGC CTGATCCAGC   360

```
AATACCGAGT GAGTGATGAA GGCCTTAGGG TTGTAAAGCT CTTTTAGCAA GGAAGATAAT      420

GACGTTACTT GCAGAAAAAG CCCCGGCTAA CTCCGTGCCA GCAGCCGCGG TAAGACGGAG      480

GGGGCTAGCG TTGTTCGGAA TTACTGGGCG TAAAGAGTGC GTAGGCGGTT TAGTAAGTTG      540

GAAGTGAAAG CCCGGGGCTT AACCTCGGAA TTGCTTTCAA AACTACTAAT CTAGAGTGTA      600

GTAGGGGATG ATGGAATTCC TAGTGTAGAG GTGAAATTCT TAGATATTAG GAGGAACACC      660

GGTGGCGAAG GCGGTCATCT GGGCTACCAC TGACGCTGAT GCACGAAAGC GTGGGGAGCA      720

AACAGGATTA GATACCCTGG TAGTCCACGC CGTAAACGAT GAGTGCTAGA TATCGGAAGA      780

TTCTCTTTCG GTTTCGCAGC TAACGCATTA AGCACTCCGC CTGGGGAGTA CGGTCGCAAG      840

ATTAAAACTC AAAGGAATTG ACGGGGCTC GCACAAGCGG TGGAGCATGC GGTTTAATTC       900

GATGTTACGC GAAAAACCTT ACCAACCCTT GACATGGTGG TTGCGGATCG CAGAGATGCT      960

TTTCTTCAGC TCGGCTGGAC CACACACAGG TGTTGCATGG CTGTCGTCAG CTCGTGTCGT     1020

GAGATGTTGG GTTAAGTCCC GCAACGAGCG CAACCCTCAT TCTTATTTGC CAGCGGGTAA     1080

TGCCGGGAAC TATAAGAAAA CTGCCGGTGA TAAGCCGGAG GAAGGTGGGG ACGACGTCAA     1140

GTCATCATGG CCCTTACGGG TTGGGCTACA CGCGTGCTAC AATGGTGTTT ACAGAGGGAA     1200

GCAAGACGGC GACGTGGAGC AAATCCCTAA AAGACATCTC AGTTCGGATT GTTCTCTGCA     1260

ACTCGAGAGC ATGAAGTTGG AATCGCTAGT AATCGCGGAT CAGCATGCCG CGGTGAATAC     1320

GTTCTCGGGC CTTGTACACA CTGCCCGTCA CGCCATGGGA GTTAGTTTTA CCTGAAGGTG     1380

GTGAGCTAAC GCAAGAGGCA GCCAACCACG GTAAAATTAG CGACTGGGGT GAAGTCGTAA     1440

(2) INFORMATION FOR SEQ ID NO:24:

(i) SEQUENCE CHARACTERISTICS:
        (A) LENGTH: 1438 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

TGGCTCAGAA CGAACGCTAT CGGTATGCTT AACACATGCA AGTCGAACGG ACTAATTGGG       60

GCTTGCTCCA ATTAGTTAGT GGCAGACGGG TGAGTAACAC GTGGGAATCT ACCCATCAGT      120

ACGGAATAAC TTTTAGAAAT AAAAGCTAAT ACCGTATATT CTCTGCGGAG GAAAGATTTA      180

TCGCTGATGG ATGAGCCCGC GTCAGATTAG GTAGTTGGTG AGGTAATGGC TCACCAAGCC      240

GACGATCTGT AGCTGGTCTG AGAGGATGAT CAGCCACACT GGGACTGAGA CACGGCCCAG      300

ACTCCTACGG GAGGCAGCAG TGGGGAATAT TGGACAATGG GCGAAAGCCT GATCCAGCAA      360

TACCGAGTGA GTGATGAAGG CCTTAGGGTT GTAAAGCTCT TTTAGCAAGG AAGATAATGA      420

CGTTACTTGC AGAAAAGCC CCGGCTAACT CCGTGCCAGC AGCCGCGGTA AGACGGAGGG       480

GGCTAGCGTT GTTCGGAATT ACTGGGCGTA AAGAGTGCGT AGGCGGTTTA GTAAGTTGGA     540

AGTGAAAGCC CGGGGCTTAA CCTCGGAATT GCTTTCAAAA CTACTAGTCT AGAGTGTAGT      600

AGGGGATGAT GGAATTCCTA GTGTAGAGGT GAAATTCTTA GATATTAGGA GGAACACCAG      660

TGGCGAAGGC GGTCATCTGG GCTACAACTG ACGCTGATGC ACGAAAGCGT GGGGAGCAAA      720

CAGGATTAGA TACCCTGGTA GTCCACGCCG TAAACGATGA GTGCTAGATA TCGGAAGATT      780

CTCTTTCGGT TTCGCAGCTA ACGCATTAAG CACTCCGCCT GGGGAGTACG GTCGCAAGAT      840

TAAAACTCAA AGGAATTGAC GGGGCTCGC ACAAGCGGTG GAGCATGCGG TTTAATTCGA       900

TGTTACGCGA AAAACCTTAC CAACCCTTGA CATGGTGGTC GCGGATCGCA GAGATGCTTT      960
```

```
TCTTCAGCTC GGCTGGACCA CACACAGGTG TTGCATGGCT GTCGTCAGCT CGTGTCGTGA    1020

GATGTTGGGT TAAGTCCCGC AACGAGCGCA ACCCTCATTC TTATTTGCCA GCGGGTAATG    1080

CCGGGAACTA TAAGAAAACT GCCGGTGATA AGCCGGAGGA AGGTGGGGAC GACGTCAAGT    1140

CATCATGGCC CTTACGGGTT GGGCTACACG CGTGCTACAA TGGTGTTTAC AGAGGGAAGC    1200

AAGACGGCGA CGTGGAGCAA ATCCCTAAAA GACATCTCAG TTCGGATTGT TCTCTGCAAC    1260

TCGAGAGCAT GAAGTTGGAA TCGCTAGTAA TCGCGGATCA GCATGCCGCG GTGAATACGT    1320

TCTCGGGCCT TGTACACACT GCCCGTCACG CCATGGGAGT TAGTTTTACC TGAAGGTGGT    1380

GAGCTAACGC AAGAGGCAGC CAACCACGGT AAAATTAGCG ACTGGGTGA AGTCGTAA      1438

(2) INFORMATION FOR SEQ ID NO:25:

(i) SEQUENCE CHARACTERISTICS:
        (A) LENGTH: 1432 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

AGAACGAACG CTATCGGTAT GCTTAACACA TGCAAGTCGA ACGGACTAAT TGGGGCTTGC      60

TCCAATTAGT TAGTGGCAGA CGGGTGAGTA ACACGTGGGA ATCTACCCAT CAGTACGGAA    120

TAACTTTTAG AAATAAAAGC TAATACCGTA TATTCTCTGC GGAGGAAAGA TTTATCGCTG    180

ATGGATGAGC CCGCGTCAGA TTAGGTAGTT GGTGAGGTAA TGGCTCACCA AGCCGACGAT    240

CTGTAGCTGG TCTGAGAGGA TGATCAGCCA CACTGGGACT GAGACACGGC CCAGACTCCT    300

ACGGGAGGCA GCAGTGGGGA ATATTGGACA ATGGGCGAAA GCCTGATCCA GCAATACCGA    360

GTGAGTGATG AAGGCCTTAG GGTTGTAAAG CTCTTTTAGC AAGGAAGATA ATGACGTTAC    420

TTGCAGAAAA AGCCCCGGCT AACTCCGTGC CAGCAGCCGC GGTAAGACGG AGGGGGCTAG    480

CGTTGTTCGG AATTACTGGG CGTAAAGAGT GCGTAGGCGG TTTAGTAAGT TGGAAGTGAA    540

AGCCCGGGGC TTAACCTCGG AATTGCTTTC AAAACTACTA ATCTAGAGTG TAGTAGGGGA    600

TGATGGAATT CCTAGTGTAG AGGTGAAATT CTTAGATATT AGGAGGAACA CCGGTGGCGA    660

AGGCGGTCAT CTGGGCTACA ACTGACGCTG ATGCACGAAA GCGTGGGGAG CAAACAGGAT    720

TAGATACCCT GGTAGTCCAC GCCGTAAACG ATGAGTGCTA GATATCGGAA GATTCTCTTT    780

CGGTTTCGTA GCTAACGCAT TAAGCACTCC GCCTGGGGAG TACGGTCGCA AGATTAAAAC    840

TCAAAGGAAT TGACGGGGGC TCGCACAAGC GGTGGAGCAT GCGGTTTAAT TCGATGTTAC    900

GCGAAAAACC TTACCAACCC TTGACATGGT GGTCGCGGAT CGCAGAGATG CTTTTCTTCA    960

GCTCGGCTGG ACCACACACA GGTGTTGCAT GGCTGTCGTC AGCTCGTGTC GTGAGATGTT   1020

GGGTTAAGTC CCGCAACGAG CGCAACCCTC ATTCTTATTT GCCAGCGGGT AATGCCGGGA   1080

ACTATAAGAA AACTGCCGGT GATAAGCCGG AGGAAGGTGG GGACGACGTC AAGTCATCAT   1140

GGCCCTTACG GGTTGGGCTA CACGCGTGCT ACAATGGTGT TTACAGAGGG AAGCAAGACG   1200

GCGACGTGGA GCAAATCCCT AAAAGACATC TCAGTTCGGA TTGTTCTCTG CAACTCGAGA   1260

GCATGAAGTT GGAATCGCTA GTAATCGCGG ATCAGCATGC CGCGGTGAAT ACGTTCTCGG   1320

GCCTTGTACA CACTGCCCGT CACGCCATGG GAGTTAGTTT TACCTGAAGG TGGTGAGCTA   1380

ACGCAAGAGG CAGCCAACCA CGGTAAAATT AGCGACTGGG GTGAAGTCGT AA           1432

(2) INFORMATION FOR SEQ ID NO:26:
```

(i) SEQUENCE CHARACTERISTICS:
    (A) LENGTH: 1440 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:26:

```
CCTGGCTCAG AACGAACGCT ATCGGTATGC TTAACACATG CAAGTCGAAC GGACTAATTG      60

GGGCTTGCTC CAATTAGTTA GTGGCAGACG GGTGAGTAAC ACGTGGGAAT CTACCCATCA     120

GTACGGAATA ACTTTTAGAA ATAAAAGCTA ATACCGTATA TTCTCTGCGG AGGAAAGATT     180

TATTGCTGAT GGATGAGCCC GCGTCAGATT AGGTAGTTGG TGAGGTAATG GCTCACCAAG     240

CCGACGATCT GTAGCTGGTC TGAGAGGATG ATCAGCCACA CTGGGACTGA GACACGGCCC     300

AGACTCCTAC GGGAGGCAGC AGTGGGGAAT ATTGCACAAT GGGCGAAAGC CTGATCCAGC     360

AATACCGAGT GAGTGATGAA GGCCTTAGGG TTGTAAAGCT CTTTTAGCAA GGAAGATAAT     420

GACGTTACTT GCAGAAAAAG CCCCGGCTAA CTCCGTGCCA GCAGCCGCGG TAAGACGGAG     480

GGGGCTAGCG TTGTTCGGAA TTACTGGGCG TAAAGAGTGC GTAGGCGGTT TAGTAAGTTG     540

GAAGTGAAAG CCCGGGGCTT AACCTCGGAA TTGCTTTCAA AACTACTAAT CTAGAGTGTA     600

GTAGGGGATG ATGGAATTCC TAGTGTAGAG GTGAAATTCT TAGATATTAG GAGGAACACC     660

GGTGGCGAAG GCGATCATCT GGGCTACAAC TGACGCTGAT GCACGAAAGC GTGGGGAGCA     720

AACAGGATTA GATACCCTGG TAGTCCACGC CGTAAACGAT GAGTGCTAGA TATCGGAAGA     780

TTCTCTTTCG GTTTCGCAGC TAACGCATTA AGCACTCCGC CTGGGGAGTA CGGTCGCAAG     840

ATTAAAACTC AAAGGAATTG ACGGGGGCTC GCACAAGCGG TGGAGCATGC GGTTTAATTC     900

GATGTTACGC GAAAAACCTT ACCAACCCTT GACATGGTGG TCGCGGATCG CAGAGATGCT     960

TTTCTTCAGC TCGGCTGGAT CACACACAGG TGTTGCATGG CTGTCGTCAG CTCGTGTCGT    1020

GAGATGTTGG GTTAAGTCCC GCAACGAGCG CAACCCTCAT TCTTATTTGC CAGCGGGTAA    1080

TGCCGGGAAC TATAAGAAAA CTGCCGGTGA TAAGCCGGAG GAAGGTGGGG ACGACGTCAA    1140

GTCATCATGG CCCTTACGGG TTGGGCTACA CGCGTGCTAC AATGGTGTTT ACAGAGGGAA    1200

GCAAGACGGC GACGTGGAGC AAATCCCTAA AAGACATCTC AGTTCGGATT GTTCTCTGCA    1260

ACTCGAGAGC ATGAAGTTGG AATCGCTAGT AATCGCGGAT CAGCATGCCG CGGTGAATAC    1320

GTTCTCGGGC CTTGTACACA CTGCCCGTCA CGCCATGGGA GTTGGTTTTA CCTGAAGGTG    1380

GTGAGCTAAC GCAAGAGGCA GCCAACCACG GTAAAATTAG CGACTGGGGT GAAGTCGTAA    1440
```

(2) INFORMATION FOR SEQ ID NO:27:

(i) SEQUENCE CHARACTERISTICS:
        (A) LENGTH: 1427 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
GAACGCTATC GGTATGCTTA ACACATGCAA GTCGAACGGA CTAATTGGGG CTTGCTCCAG      60

TTAGTTAGTG GCAGACGGGT GAGTAACACG TGGGAATCTA CCCATTAGTA CGGAATAACT     120

TTTAGAAATA AAAGCTAATA CCGTATATTC TCTGCGGAGG AAAGATTTAT CGCTGATGGA     180

TGAGCCCGCG TCAGATTAGG TAGTTGGTGA GGTAATGGCT CACCAAGCCG ACGATCTGTA     240
```

-continued

```
GCTGGTCTGA GAGGATGATC AGCCACACTG GGACTGAGAC ACGGCCCAGA CTCCTACGGG    300

AGGCAGCAGT GGGGAATATT GGACAATGGG CGAAAGCCTG ATCCAGCAAT ACCGAGTGAG    360

TGATGAAGGC CTTAGGGTTG TAAAGCTCTT TTAGCAAGGA AGATAATGAC GTTACTTGCA    420

GAAAAAGCCC CGGCTAACTC CGTGCCAGCA GCCGCGGTAA GACGGAGGGG GCTAGCGTTG    480

TTCGGAATTA CTGGGCGTAA AGAGTGCGTA GGCGGTTTAG TAAGTTGGAA GTGAAAGCCC    540

GGGGCTTAAC CTCGGAATTG CTTTCAAAAC TACTAATCTA GAGTGTAGTA GGGGATGATG    600

GAATTCCTAG TGTAGAGGTG AAATTCTTAG ATATTAGGAG GAACACCGGT GGCGAAGGCG    660

GTCATCTGGG CTACAACTGA CGCTGATGCA CGAAAGCGTG GGGAGCAAAC AGGATTAGAT    720

ACCCTGGTAG TCCACGCCGT AAACGATGAG TGCTAGATAT CGGAAGATTC TCTTTCGGTT    780

TCGCAGCTAA CGCATTAAGC ACTCCGCCTG GGGAGTACGG TCGCAAGATT AAAACTCAAA    840

GGAATTGACG GGGGCTCGCA CAAGCGGTGG AGCATGCGGT TTAATTCGAT GTTACGCGAA    900

AAACCTTACC AACCCTTGAC ATGGTGGTCG CGGATCGCAG AGATGCTTTT CTTCAGCTCG    960

GCTGGACCAC ACACAGGTGT TGCATGGCTG TCGTCAGCTC GTGTCGTGAG ATGTTGGGTT   1020

AAGTCCCGCA ACGAGCGCAA CCCTCATTCT TATTTGCCAG CGGGTAATGC CGGGAACTAT   1080

AAGAAAACTG CCGGTGATAA GCCGGAGGAA GGTGGGGACG ACGTCAAGTC ATCATGGCCC   1140

TTACGGGTTG GGCTACACGC GTGCTACAAT GGTGTTTACA GAGGGAAGCA AGACGGCGAC   1200

GTGGAGCAAA TCCCTAAAAG ACATCTCAGT TCGGATTGTT CTCTGCAACT CGAGAGCATG   1260

AAGTTGGAAT CGCTAGTAAT CGCGGATCAG CATGCCGCGG TGAATACGTT CTCGGGCCTT   1320

GTACACACTG CCCGTCACGC CATGGGAGTT AGTTTTACCT GAAGGTGGTG AGCTAACGCA   1380

AGAGGCAGCC AACCACGGTA AAATTAGCGA CTGGGGTGAA GTCGTAA                 1427
```

(2) INFORMATION FOR SEQ ID NO:28:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
CCTGGCTCAG AACGAACGCT ATCGGTATGC TTAACACATG CAAGTCGAAC GGACTAATTG     60

GGGCTTGCTC CAGTTAGTTA GTGGCAGACG GGTGAGTAAC ACGTGGGAAT CTACCCATTA    120

GTACGGAATA ACTTTTAGAA ATAAAAGCTA ATACCGTATA TTCTCTGCGG AGGAAAGATT    180

TATCGCTGAT GGATGAGCCC GCGTCAGATT AGGTAGTTGG TGAGGTAATG GCTCACCAAG    240

CCGACGATCT GTAGCTGGTC TGAGAGGATG ATCAGCCACA CTGGGACTGA GACACGGCCC    300

AGACTCCTAC GGGAGGCAGC AGTGGGGAAT ATTGGACAAT GGGCGAAAGC CTGATCCAGC    360

AATACCGAGT GAGTGATGAA GGCCTTAGGG TTGTAAAGCT CTTTTAGCAA GGAAGATAAT    420

GACGTTACTT GCAGAAAAAG CCCCGGCTAA CTCCGTGCCA GCAGCCGCGG TAAGACGGAG    480

GGGGCTAGCG TTGTTCGGAA TTACTGGGCG TAAAGAGTGC GTAGGCGGTT TAGTAAGTTG    540

GAAGTGAAAG CCCGGGGCTT AACCTCGGAA TTGCTTTCAA AACTACTAAT CTAGAGTGTA    600

GTAGGGGATG ATGGAATTCC TAGTGTAGAG GTGAAATTCT TAGATATTAG GAGGAACACC    660

GGTGGCGAAG GCGGTCATCT GGGCTACAAC TGACGCTGAT GCACGAAAGC GTGGGGAGCA    720

AACAGGATTA GATACCCTGG TAGTCCACGC CGTAAACGAT GAGTGCTAGA TATCGGAAGA    780

GTCTCTTTCG GTTTCGCAGC TAACGCATTA AGCACTCCGC CTGGGGAGTA CGGTCGCAAG    840
```

```
ATTAAAACTC AAAGGAATTG ACGGGGCTC GCACAAGCGG TGGAGCATGC GGTTTAATTC      900

GATGTTACGC GAAAAACCTT ACCAACCCTT GACATGGTGG TCGCGGATCG CAGAGATGCT      960

TTTCTTCAGC TCGGCTGGAC CACACACAGG TGTTGCATGG CTGTCGTCAG CTCGTGTCGT     1020

GAGATGTTGG GTTAAGTCCC GCAACGAGCG CAACCCTCAT TCTTATTTGC CAGCGGGTAA     1080

TGCCGGGAAC TATAAGAAAA CTGCCGGTGA TAAGCCGGAG GAAGGTGGGG ACGACGTCAA     1140

GTCATCATGG CCCTTACGGG TTGGGCTACA CGCGTGCTAC AATGGTGTTT ACAGAGGGAA     1200

GCAAGACGGC GACGTGGAGC AAATCCCTAA AAGACATCTC AGTTCGGATT GTTCTCTGCA     1260

ACTCGAGAGC ATGAAGTTGG AATCGCTAGT AATCGCGGAT CAGCATGCCG CGGTGAATAC     1320

GTTCTCGGGC CTTGTACACA CTGCCCGTCA CGCCATGGGA GTTAGTTTTA CCTGAAGGTG     1380

GTGAGCTAAC GCAAGAGGCA GCCAACCACG GTAAAATTAG CGACTGGGGT GAAGTCGTAA     1440

(2) INFORMATION FOR SEQ ID NO:29:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CCTGGCTCAG AACGAACGCT ATCGGTATGC TTAACACATG CAAGTCGAAC GGACTAATTG       60

GGGCTTGCTC CAGTTAGTTA GTGGCAGACG GGTGAGTAAC ACGTGGGAAT CTACCCATTA      120

GTACGGAATA ACTTTTAGAA ATAAAAGCTA ATACCGTATA TTCTCTGTGG AGGAAAGATT      180

TATCGCTGAT GGATGAGCCC GCGTCAGATT AGGTAGTTGG TGAGGTAATG GCTCACCAAG      240

CCGACGATCT GTAGCTGGTC TGAGAGGATG ATCAGCCACA CTGGGACTGA GACACGGCCC      300

AGACTCCTAC GGGAGGCAGC AGTGGGGAAT ATTGGACAAT GGGCGAAAGC CTGATCCAGC      360

AATACCGAGT GAGTGATGAA GGCCTTAGGG TTGTAAAGCT CTTTTAGCAA GGAAGATAAT      420

GACGTTACTT GCAGAAAAAG CCCCGGCTAA CTCCGTGCCA GCAGCCGCGG TAAGACGGAG      480

GGGGCTAGCG TTGTTCGGAA TTACTGGGCG TAAAGAGTGC GTAGGCGGTT TAGTAAGTTG      540

GAAGTGAAAG CCCGGGGCTT AACCTCGGAA TTGCTTTCAA AACTACTAAT CTAGAGTGTA      600

GTAGGGGATG ATGGAATTCC TAGTGTAGAG GTGAAATTCT TAGATATTAG GAGGAACACC      660

GGTGGCGAAG GCGGTCATCT GGGCTACAAC TGACGCTGAT GCACGAAAGC GTGGGGAGCA      720

AACAGGATTA GATACCCTGG TAGTCCACGC CGTAAACGAT GAGTGCTAGA TATCGGAAGA      780

TTTTCTTTCG GTTTCGCAGC TAACGCATTA AGCACTCCGC CTGGGGAGTA CGGTCGCAAG      840

ATTAAAACTC AAAGGAATTG ACGGGGCTC GCACAAGCGG TGGAGCATGC GGTTTAATTC      900

GATGTTACGC GAAAAACCTT ACCAACCCTT GACATGGTGG TCGCGGATCG CAGAGATGCT      960

TTTCTTCAGC TCGGCTGGAC CACACACAGG TGTTGCATGG CTGTCGTCAG CTCGTGTCGT     1020

GAGATGTTGG GTTAAGTCCC GCAACGAGCG CAACCCTCAT TCTTATTTGC CAGCGGGTAA     1080

TGCCGGGAAC TATAAGAAAA CTGCCGGTGA TAAGCCGGAG GAAGGTGGGG ACGACGTCAA     1140

GTCATCATGG CCCTTACGGG TTGGGCTACA CGCGTGCTAC AATGGTGTTT ACAGAGGGAA     1200

GCAAGACGGC GACGTGGAGC AAATCCCTAA AAGACATCTC AGTTCGGATT GTTCTCTGCA     1260

ACTCGAGAGC ATGAAGTTGG AATCGCTAGT AATCGCGGAT CAGCATGCCG CGGTGAATAC     1320

GTTCTCGGGC CTTGTACACA CTGCCCGTCA CGCCATGGGA GTTAGTTTTA CCTGAAGGTG     1380
```

-continued

GTGAGCTAAC GCAAGAGGCA GCCAACCACG GTAAAATTAG CGACTGGGGT GAAGTCGTAA    1440

(2) INFORMATION FOR SEQ ID NO:30:

(i) SEQUENCE CHARACTERISTICS:
       (A) LENGTH: 1442 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:30:

CCTGGCTCAG AACGAACGCT ATCGGTATGC TTAACACATG CAAGTCGAAC GGACTAATTT      60

GGGGCTTGCT CCAATTTAGT TAGTGGCAGA CGGGTGAGTA ACACGTGGGA ATCTACCCAT    120

TAGTACGGAA TAACTTTTAG AAATAAAAGC TAATACCGTA TATTCTCTGC GGAGGAAAGA    180

TTTATCGCTG ATGGATGAGC CCGCGTCAGA TTAGGTAGTT GGTGAGGTAA TGGCTCACCA    240

AGCCGACGAT CTGTAGCTGG TCTGAGAGGA TGATCAGCCA CACTGGGACT GAGACACGGC    300

CCAGACTCCT ACGGGAGGCA GCAGTGGGGA ATATTGGACA ATGGGCGAAA GCCTGATCCA    360

GCAATACCGA GTGAGTGATG AAGGCCTTAG GGTTGTAAAG CTCTTTTAGC AAGGAAGATA    420

ATGACGTTAC TTGCAGAAAA AGCCCCGGCT AACTCCGTGC CAGCAGCCGC GGTAAGACGG    480

AGGGGGCTAG CGTTGTTCGG AATTACTGGG CGTAAAGAGT GCGTAGGCGG TTTAGTAAGT    540

TGGGAGTGAA AGCCCGGGGC TTAACCTCGG AATTGCTTTC AAAACTACTA ATCTAGAGTG    600

TAGTAGGGGA TGATGGAATT CCTAGTGTAG AGGTGAAATT CTTAGATATT AGGAGGAACA    660

CCGGTGGCGA AGGCGGTCAT CTGGGCTACA ACTGACGCTG ATGCACGAAA GCGTGGGGAG    720

CAAACAGGAT TAGATACCCT GGTAGTCCAC GCCGTAAACG ATGAGTGCTA GATATCGGAA    780

GATTCTCTTT CGGTTTCGCA GCTAACGCAT TAAGCACTCC GCCTGGGGAG TACGGTCGCA    840

AGATTAAAAC TCAAAGGAAT TGACGGGGGC TCGCACAAGC GGTGGAGCAT GCGGTTTAAT    900

TCGATGTTAC GCGAAAAACC TTACCAACCC TTGACATGGT GGTCGCGGAT CGCAGAGATG    960

CTTTTCTTCA GCTCGGCTGG ACCACACACA GGTGTTGCAT GGCTGTCGTC AGCTCGTGTC   1020

GTGAGATGTT GGGTTAAGTC CCGCAACGAG CGCAACCCTC ATTCTTATTT GCCAGCGGGT   1080

AATGCCGGGA ACTATAAGAA AACTGCCGGT GATAAGCCGG AGGAAGGTGG GGACGACGTC   1140

AAGTCATCAT GGCCCTTACG GGTTGGGCTA CACGCGTGCT ACAATGGTGT TTACAGAGGG   1200

AAGCAAGACG GCGACGTGGA GCAAATCCCT AAAAGACATC TCAGTTCGGA TTGTTCTCTG   1260

CAACTCGAGA GCATGAAGTT GGAATCGCTA GTAATCGCGG ATCAGCATGC CGCGGTGAAT   1320

ACGTTCTCGG GCCTTGTACA CACTGCCCGT CACGCCATGG GAGTTAGTTT TACCTGAAGG   1380

TGGTGAGCTA ACGCAAGAGG CAGCCAACCA CGGTAAAATT AGCGACTGGG GTGAAGTCGT   1440

AA                                                                  1442

(2) INFORMATION FOR SEQ ID NO:31:

(i) SEQUENCE CHARACTERISTICS:
       (A) LENGTH: 1439 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:31:

TGGCTCAGAA CGAACGCTAT CGGTATGCTT AACACATGCA AGTCGAACGG ACTAATTTGG     60

```
GGCTTGCTCC AATTAGTTAG TGGCAGACGG GTGAGTAACA CGTGGGAATC TACCCATTAG      120

TACGGAATAA CTTTTAGAAA TAAAAGCTAA TACCGTATAT TCTCTGCGGA GGAAAGATTT      180

ATCGCTGATG GATGAGCCCG CGTCAGATTA GGTAGTTGGT GAGGTAATAG CTCACCAAGC      240

CGACGATCTG TAGCTGGTCT GAGAGGATGA TCAGCCACAC TGGGACTGAG ACACGGCCCA      300

GACTCCTACG GGAGGCAGCA GTGGGGAATA TTGGACAATG GGCGAAAGCC TGATCCAGCA      360

ATACCGAGTG AGTGATGAAG GCCTTAGGGT TGTAAAGCTC TTTTAGCAAG GAAGATAATG      420

ACGTTACTTG CAGAAAAAGC CCCGGCTAAC TCCGTGCCAG CAGCCGCGGT AAGACGGAGG      480

GGGCTAGCGT TGTTCGGAAT TACTGGGCGT AAAGAGTGCG TAGGCGGTTT AGTAAGTTGG      540

AAGTGAAAGC CCGGGGCTTA ACCTCGGAAT TGCTTTCAAA ACTACTAATC TAGAGTGTAG      600

TAGGGGATGA TGGAATTCCT AGTGTAGAGG TGAAATTCTT AGATATTAGG AGGAACACCG      660

GTGGCGAAGG CGGTCGTCTG GCTACAACT GACGCTGATG CACGAAAGCG TGGGGAGCAA      720

ACAGGATTAG ATACCCTGGT AGTCCACGCC GTAAACGATG AGTGCTAGAT ATCGGAAGAT      780

TCTCTTTCGG TTTCGCAGCT AACGCATTAA GCACTCCGCC TGGGGAGTAC GGTCGCAAGA      840

TTAAAACTCA AAGGAATTGA CGGGGGCTCG CACAAGCGGT GGAGCATGCG GTTTAATTCG      900

ATGTTACGCG AAAAACCTTA CCAACCCTTG ACATGGTGGT CGCGGATCGC AGAGATGCTT      960

TTCTTCAGCT CGGCTGGACC ACACACAGGT GTTGCATGGT TGTCGTCAGC TCGTGTCGTG     1020

AGATGTTGGG TTAAGTCCCG CAACGAGCGC AACCCTCATT CTTATTTGCC AGCGGGTAAT     1080

GCCGGGAACT ATAAGAAAAC TGCCGGTGAT AAGCCGGAGG AAGGTGGGGA CGACGTCAAG     1140

TCATCATGGC CCTTACGGGT TGGGCTACAC GCGTGCTACA ATGGTGTTTA CAGAGGGAAG     1200

CAAGACGGCG ACGTGGAGCA AATCCCTAAA AGACATCTCA GTTCGGATTG TTCTCTGCAA     1260

CTCGAGAGCA TGAAGTTGGA ATCGCTAGTA ATCGCGGATC AGCATGCCGC GGTGAATACG     1320

TTCTCGGGCC TTGTACACAC TGCCCGTCAC GCCATGGGAG TTAGTTTTAC CTGAAGGTGG     1380

TGAGCTAACG CAAGAGGCAG CCAACCACGG TAAAATTAGC GACTGGGGTG AAGTCGTAA     1439

(2) INFORMATION FOR SEQ ID NO:32:

(i) SEQUENCE CHARACTERISTICS:
           (A) LENGTH: 1432 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:32:

ACGAACGCTA TCGGTATGCT TAACACATGC AAGTCGAACG AACTAATTTT TGGGGCTTGC       60

TCCAATTAGT TAGTGGCAGA CGGGTGAGTA ACACGTGGGA ATCTACCCAT TAGTACGGAA      120

TAACTTTTAG AAATAAAAGC TAATACCGTA TATTCTCTGC GGAGGAAAGA TTTATCGCTG      180

ATGGATGAGC CCGCGTCAGA TTAGGTAGTT GGTGAGGTAA TGGCTCACCA AGCCGACGAT      240

CTGTAGCTGG TCTGAGAGGA TGATCAGCCA CACTGGGACT GAGACACGGC CCAGACTCCT      300

ACGGGAGGCA GCAGTGGGGA ATATTGGACA ATGGGCGAAA GCCTGATCCA GCAATACCGA      360

GTGAGTGATG AAGGCCTTAG GGTTGTAAAG CTCTTTTAGC AAGGAAGATA ATGACGTTAC      420

TTGCAGAAAA AGCCCCGGCT AACTCCGTGC CAGCAGCCGC GGTAAGACGG AGGGGCTAG      480

CGTTGTTCGG AATTACTGGG CGTAAAGAGT GCGTAGGCGG TTTAGTAAGT TGGAAGTGAA      540

AGCCCGGGGC TTAACCTCGG AATTGCTTTC AAAACTACTA ATCTAGAGTG TAGTAGGGGA      600

TGATGGAATT CCTAGTGTAG AGGTGAAATT CTTAGATATT AGGAGGAACA CCGGTGGCGA      660
```

```
AGGCGGTCAT CTGGGCTACA ACTGACGCTG ATGCACGAAA GCGTGGGAG CAAACAGGAT      720

TAGATACCCT GGTAGTCCAC GCCGTAAACG ATGAGTGCTA GATATCGGAA GATTCTCTTT      780

CGGTTTCGCA GCTAACGCAT TAAGCACTCC GCCTGGGGAG TACGGTCGCA AGATTAAAAC      840

TCAAAGGAAT TGACGGGGGC TCGCACAAGC GGTGGAGCAT GCGGTTTAAT TCGATGTTAC      900

GCGAAAAACC TTACCAACCC TTGACATGGT GGTCGTGGAT CGCAGAGATG CTTTTCTTCA      960

GCTCGGCTGG ACCACACACA GGTGTTGCAT GGCTGTCGTC AGCTCGTGTC GTGAGATGTT     1020

GGGTTAAGTC CCGCAACGAG CGCAACCCTC ATTCTTATTT GCCAGCGGGT AATGCCGGGA     1080

ACTATAAGAA AACTGCCGGT GATAAGCCGG AGGAAGGTGG GGACGACGTC AAGTCATCAT     1140

GGCCCTTACG GGTTGGGCTA CACGCGTGCT ACAATGGTGT TTACAGAGGG AAGCAAGACG     1200

GCGACGTGGA GCAAATCCCT AAAAGACATC TCAGTTCGGA TTGTTCTCTG CAACTCGAGA     1260

GCATGAAGTT GGAATCGCTA GTAATCGCGG ATCAGCATGC CGCGGTGAAT ACGTTCTCGG     1320

GCCTTGTACA CACTGCCCGT CACGCCATGG GAGTTAGTTT TACCTGAAGG TGGTGAGCTA     1380

ACGCAAGAGG CAGCCAACCA CGGTAAAATT AGCGACTGGG GTGAAGTCGT AA             1432
```

(2) INFORMATION FOR SEQ ID NO:33:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

```
CCTGGCTCAG AACGAACGCT ATCGGTATGC TTAACACATG CAAGTCGAAC GGACTAATTG       60

GGGCTTGCTC TAATTAGTTA GTGGCAGACG GGTGAGTAAC ACGTGGGAAT CTACCCATCA      120

GTACGGAATA ACTTTTAGAA ATAAAGCTA ATACCGTATA TTCTCTACGG AGGAAAGATT      180

TATCGCTGAT GGATGAGCCC GCGTCAGATT AGGTAGTTGG TGAGGTAATG GCTCACCAAG      240

CCGACGATCT GTAGCTGGTC TGAGAGGATG ATCAGCCACA CTGGGACTGA GACACGGCCC      300

AGACTCCTAC GGGAGGCAGC AGTGGGGAAT ATTGGACAAT GGGCGAAAGC CTGATCCAGC      360

AATACCGAGT GAGTGATGAA GGCCTTAGGG TTGTAAAGCT CTTTTAGCAA GGAAGATAAT      420

GACGTTACTT GCAGAAAAAG CCCCGGCTAA CTCCGTGCCA GCAGCCGCGG TAAGACGGAG      480

GGGGCTAGCG TTGTTCGGAA TTACTGGGCG TAAAGAGTGC GTAGGCGGTT TAGTAAGTTG      540

GAAGTGAAAG CCCGGGGCTT AACCTCGGAA TTGCTTTCAA AACTACTAAT CTAGAGTGTA      600

GTAGGGGATG ATGGAATTCC TAGTGTAGAG GTGAAATTCT TAGATATTAG GAGGAACACC      660

GGTGGCGAAG GCGGTCATCT GGGCTACAAC TGACGCTGAT GCACGAAAGC GTGGGGAGCA      720

AACAGGATTA GATACCCTGG TAGTCCACGC CGTAAACGAT GAGTGCTAGA TATCGGAAGA      780

TTCTCTTTCG GTTTCGCAGC TAACGCATTA AGCACTCCGC CTGGGAGTA CGGTCGCAAG      840

ATTAAAACTC AAAGGAATTG ACGGGGCTC GCACAAGCGG TGGAGCATGC GGTTTAATTC      900

GATGTTACGC GAAAAACCTT ACCAACCCTT GACATGGTGG TCGCGGATCG CAGAGATGCT      960

TTTCTTCAGC TCGGCTGGAC CACACACAGG TGTTGCATGG CTGTCGTCAG CTCGTGTCGT     1020

GAGATGTTGG GTTAAGTCCC GCAACGAGCG CAACCCTCAT TCTTATTTGC CAGCGGGTAA     1080

TGCCGGGAAC TATAAGAAAA CTGCCGGTGA TAAGCCGGAG GAAGGTGGGG ATGACGTCAA     1140

GTCATCATGG CCCTTACGGG TTGGGCTACA CGCGTGCTAC AATGGTGTTT ACAGAGGGAA     1200
```

```
GCAAGACGGC GACGTGGAGC AAATCCCTAA AAGACATCTC AGTTCGGATT GTTCTCTGCA    1260

ACTCGAGAGC ATGAAGTTGG AATCGCTAGT AATCGCGGAT CAGCATGCCG CGGTGAATAC    1320

GTTCTCGGGC CTTGTACACA CTGCCCGTCA CGCCATGGGA GTTGGTTTTA CCTGAAGGTG    1380

GTGAGCTAAC GCAAGAGGCA GCCAACCACG GTAAAATTAG CGACTGGGGT GAAGTCGTAA    1440
```

(2) INFORMATION FOR SEQ ID NO:34:

(i) SEQUENCE CHARACTERISTICS:
        (A) LENGTH: 1436 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

```
GCTCAGAACG AACGCTATCG GTATGCTTAA CACATGCAAG TCGAACGGAC TAATTGGGGC     60

TTGCTCCAAT TAGTTAGTGG CAGACGGGTG AGTAACACGT GGGAATCTAC CCATCAGTAC    120

GGAATAACTT TTAGAAATAA AAGCTAATAC CGTATATTCT CTACGGAGGA AAGATTTATC    180

GCTGATGGAT GAGCCCGCGT CAGATTAGGT AGTTGGTGAG GTAATGGCTC ACCAAGCCGA    240

CGATCTGTAG CTGGTCTGAG AGGATGATCA GCCACACTGG GACTGAGACA CGGCCCAGAC    300

TCCTACGGGA GGCAGCAGTG GGGAATATTG GACAATGGGC GAAAGCCTGA TCCAGCAATA    360

CCGAGTGAGT GATGAAGGCC TTAGGGTTGT AAAGCTCTTT TAGCAAGGAA GATAATGACG    420

TTACTTGCAG AAAAAGCCCC GGCTAACTCC GTGCCAGCAG CCGCGGTAAG ACGGAGGGGG    480

CTAGCGTTGT TCGGAATTAC TGGGCGTAAA GAGTGCGTAG GCGGTTTAGT AAGTTGGAAG    540

TGAAAGCCCG GGGCTTAACC TCGGAATTGC TTTCAAAACT ACTAATCTAG AGTGTAGTAG    600

GGATGATGG AATTCCTAGT GTAGAGGTGA AATTCTTAGA TATTAGGAGG AACACCGGTG    660

GCGAAGGCGG TCATCTGGGC TACAACTGAC GCTGATGCAC GAAAGCGTGG GGAGCAAACA    720

GGATTAGATA CCCTGGTAGT CCACGCCGTA ACGATGAGT GCTAGATATC GGAAGATTCT    780

CTTTCGGTTT CGCAGCTAAC GCATTAAGCA CTCCGCCTGG GGAGTACGGT CGCAAGATTA    840

AAACTCAAAG GAATTGACGG GGGCTCGCAC AAGCGGTGGA GCATGCGGTT TAATTCGATG    900

TTACGCGAAA AACCTTACCA ACCCTTGACA TGGTGGTCGC GGATCGCAGA GATGCTTTTC    960

TTCAGCTCGG CTGGACCACA CACAGGTGTT GCATGGCTGT CGTCAGCTCG TGTCGTGAGA   1020

TGTTGGGTTA AGTCCCGCAA CGAGCGCAAC CCTCATTCTT ATTTGCCAGC GGGTAATGCC   1080

GGGAACTATA AGAAAACTGC CGGTGATAAG CCGGAGGAAG GTGGGGATGA CGTCAAGTCA   1140

TCATGGCCCT TACGGGTTGG GCTACACGCG TGCTACAATG GTGTTTACAG AGGGAAGCAA   1200

GACGGCGACG TGGAGCAAAT CCCTAAAAGA CATCTCAGTT CGGATTGTTC TCTGCAACTC   1260

GAGAGCATGA AGTTGGAATC GCTAGTAATC GCGGATCAGC ATGCCGCGGT GAATACGTTC   1320

TCGGGCCTTG TACACACTGC CCGTCACGCC ATGGGAGTTG GTTTTACCTG AAGGTGGTGA   1380

GCTAACGCAA GAGGCAGCCA ACCACGGTAA AATTAGCGAC TGGGGTGAAG TCGTAA       1436
```

(2) INFORMATION FOR SEQ ID NO:35:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

```
CCTGGCTCAG AACGAACGCT ATCGGTATGC TTAACACATG CAAGTCGAAC GGGCTAATTG      60
GGGCTTGCTC CAATTAGTTA GTGGCAGACG GGTGAGTAAC ACGTGGGAAT CTACCCATCA     120
GTACGGAATA ACTTTTAGAA ATAAAAGCTA ATACCGTATA TTCTCTACGG AGGAAAGATT     180
TATCGCTGAT GGATGAGCCC GCGTCAGATT AGGTAGTTGG TGAGGTAATG GCTCACCAAG     240
CCGACGATCT GTAGCTGGTC TGAGAGGATG ATCAGCCACA CTGGGACTGA GACACGGCCC     300
AGACTCCTAC GGGAGGCAGC AGTGGGGAAT ATTGGACAAT GGGCGAAAGC CTGATCCAGC     360
AATACCGAGT GAGTGATGAA GGCCTTAGGG TTGTAAAGCT CTTTTAGCAA GGAAGATAAT     420
GACGTTACTT GCAGAAAAAG CCCCGGCTAA CTCCGTGCCA GCAGCCGCGG TAAGACGGAG     480
GGGGCTAGCG TTGTTCGGAA TTACTGGGCG TAAAGAGTGC GTAGGCGGTT TAGTAAGTTG     540
GAAGTGAAAG CCCGGGGCTT AACCTCGGAA TTGCTTTCAA AACTACTAAT CTAGAGTATA     600
GTAGGGGATG ATGGAATTCC TAGTGTAGAG GTGAAATTCT TAGATATTAG GAGGAACACC     660
GGTGGCGAAG GCGGTCATCT GGGCTACAAC TGACGCTGAT GCACGAAAGC GTGGGGAGCA     720
AACAGGATTA GATACCCTGG TAGTCCACGC CGTAAACGAT GAGTGCTAGA TATCGGAAGA     780
TTCTCTTTCG GTTTCGCAGC TAACGCATTA AGCACTCCGC CTGGGAGTA CGGTCGCAAG     840
ATTAAAACTC AAAGGAATTG ACGGGGCTC GCACAAGCGG TGGAGCATGC GGTTTAATTC     900
GATGTTACGC GAAAAACCTT ACCAACCCTT GACATGGTGG TCGCGGATCG CAGAGATGCT     960
TTTCTTCAGC TCGGCTGGAC CACACACAGG TGTTGCATGG CTGTCGTCAG CTCGTGTCGT    1020
GAGATGTTGG GTTAAGTCCC GCAACGAGCG CAACCCTCAT TCTTATTTGC CAGCGGGTAA    1080
TGCCGGGAAC TATAAGAAAA CTGCCGGTGA TAAGCCGGAG GAAGGTGGGG ACGACGTCAA    1140
GTCATCATGG CCCTTACGGG TTGGGCTACA CGCGTGCTAC AATGGTGTTT ACAGAGGGAA    1200
GCAAGACGGC GACGTGGAGC AAATCCCTAA AAGACATCTC AGTTCGGATT GTTCTCTGCA    1260
ACTCGAGAGC ATGAAGTTGG AATCGCTAGT AATCGCGGAT CAGCATGCCG CGGTGAATAC    1320
GTTCTCGGGC CTTGTACACA CTGCCCGTCA CGCCATGGGA GTTGGTTTTA CCTGAAGGTG    1380
GTAAGCTAAC GCAAGAGGCA GCCAACCACG GTAAAATTAG CGACTGGGGT GAAGTCGTAA    1440
```

(2) INFORMATION FOR SEQ ID NO:36:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

```
CCTGGCTCAG AACGAACGCT ATCGGTATGC TTAACACATG CAAGTCGAAC GGACTAATTG      60
GAGCTTGCTC CAATTAGTTA GTGGCAGACG GGTGAGTAAC GCGTGGGAAT CTACCCATCA     120
GTACGGAATA ACTTTTAGAA ATAAAAGCTA ATACCGTATA TTCTCTACGG AGGAAAGGTT     180
TATCGCTGAT GGATGAGCCC GCGTCAGATT AGGTAGTTGG TGAGGTAATG GCTCACCAAG     240
CCGACGATCT GTAGCTGGTC TGAGAGGATG ATCAGCCACA CTGGGACTGA GACACGGCCC     300
AGACTCCTAC GGGAGGCAGC AGTGGGGAAT ATTGGACAAT GGGCGAAAGC CTGATCCAGC     360
AATACCGAGT GAGTGATGAA GGCCTTAGGG TTGTAAAGCT CTTTTAGCAG GAAGATAAT     420
GACGTTACTT GCAGAAAAAG CCCCGGCTAA CTCCGTGCCA GCAGCCGCGG TAAGACGGAG     480
GGGGCTAGCG TTGTTCGGAA TTACTGGGCG TAAAGAGTGC GTAGGCGGTT TAGTAAGTTG     540
```

```
GAAGTGAAAG CCCGGGGCTT AACCTCGGAA TTGCTTTCAA AACTACTAAT CTAGAGTGTA     600

GTAGGGGATG ATGGAATTCC TAGTGTAGAG GTGAAATTCT TAGATATTAG GAGGAACACC     660

GGTGGCGAAG GCGGTCATCT GGGCTGCAAC TGACGCTGAT GCACGAAAGC GTGGGGAGCA     720

AACAGGATTA GATACCCTGG TAGTCCACGC CGTAAACGAT GAGTGCTAGA TATCGGAAGA     780

TTCTCTTTCG GTTTCGCAGC TAACGCATTA AGCACTCCGC CTGGGGAGTA CGGTCGCAAG     840

ATTAAAACTC AAAGGAATTG ACGGGGCTC GCACAAGCGG TGGAGCATGC GGTTTAATTC     900

GATGTTACGC GAAAAACCTT ACCAACCCTT GACATGGTGG TCGTGAATCG CAGAGATGCT     960

TTTCTTCAGC TCGGCTGGAC CACACACAGG TGTTGCATGG CTGTCGTCAG CTCGTGTCGT    1020

GAGATGTTGG GTTAAGTCCC GCAACGAGCG CAACCCTCAT TCTTATTTGC CAGCGGGTAA    1080

TGCCGGGAAC TATAAGAAAA CTGCCGGTGA TAAGCCGGAG GAAGGTGGGG ACGACGTCAA    1140

GTCATCATGG CCCTTACGGG TTGGGCTACA CGCGTGCTAC AATGGTGTTT ACAGAGGGAA    1200

GCAAGACGGC GACGTGGAGC AAATCCCTAA AAGACATCTC AGTTCGGATT GTTCTCTGCA    1260

ACTCGAGAGC ATGAAGTTGG AATCGCTAGT AATCGCGGAT CAGCATGCCG CGGTGAATAC    1320

GTTCTCGGGC CTTGTACACA CTGCCCGTCA CGCCATGGGA GTTGGTTTTA CCTGAAGGTG    1380

GTGAGCTAAC GCAAGAGGCA GCCAACCACG GTAAAATTAG CGACTGGGGT GAAGTCGTAA    1440

(2) INFORMATION FOR SEQ ID NO:37:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

CCTGGCTCAG AACAAACGCT ATCGGTATGC TTAACACATG CAAGTCGAAC GGACTAATTG      60

GGGCTTGTTC CAGTTAGTTA GTGGCAGACG GGTGAGTAAC ACGTGGGAAT CTACCCATCA     120

GTATGGAATA ACTTTTAGAA ATAAAAGCTA ATACCATATA TTCTCTATGG AGGAAAGATT     180

TATCGCTGAT GGATGAGCCC GCGTCAGATT AGGTAGTTGG TGAGGTAACG GCTCACCAAG     240

CCGACGATCT GTAGCTGGTC TGAGAGGATG ATCAGCCACA CTGGGACTGA GACACGGCCC     300

AGACTCCTAC GGGAGGCAGC AGTGGGGAAT ATTGGACAAT GGGCGAAAGC CTGATCCAGC     360

AATACCGAGT GAGTGATGAA GGCCTTAGGG TTGTAAAGCT CTTTTAGCAA GGAAGATAAT     420

GACGTTACTT GCAGAAAAAG CCCCGGCTAA CTCCGTGCCA GCAGCCGCGG TAAGACGGAG     480

GGGGCTAGCG TTGTTCGGAA TTACTGGGCG TAAAGAGTGC GTAGGCGGTT TAGTAAGTTG     540

GAAGTGAAAG CCCGGGGCTT AACCTCGGAA TTGCTTTCAA AACTACTAAT CTAGAGTGTA     600

GTAGGGGATG ATGGAATTCC TAGTGTAGAG GTGAAATTCT TAGATATTAG GAGGAACACC     660

GGTGGCGAAG GCGATCATCT GGGCTACAAC TGACGCTGAT GCACGAAAGC GTGGGGAGCA     720

AACAGGATTA GATACCCTGG TAGTCCACGC CGTAAACGAT GAGTGCTAGA TATCGGAAGA     780

TTCTCTTTCG GTTTCGCAGC TAACGCATTA AGCACTCCGC CTGGGGAGTA CGGTCGCAAG     840

ATTAAAACTC AAAGGAATTG ACGGGGCTC GCACAAGCGG TGGAGCATGC GGTTTAATTC     900

GATGTTACGC GAAAAACCTT ACCAACCCTT GACATGGTGG TCGCGGATCG CAGAGATGCT     960

TTCCTTCAGC TCGGCTGGAC CACACACAGG TGTTGCATGG CTGTCGTCAG CTCGTGTCGT    1020

GAGATGTTGG GTTAAGTCCC GCAACGAGCG CAACCCTCAT TCTTATTTGC CAGCGGGTAA    1080
```

(2) INFORMATION FOR SEQ ID NO:38:

(i) SEQUENCE CHARACTERISTICS:
        (A) LENGTH: 1441 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

```
TGCCAGGAAC TATAAGAAAA CTGCCGGTGA TAAGCCGGAG GAAGGTGGGG ACGACGTCAA    1140
GTCATCATGG CCCTTACGGG TTGGGCTACA CGCGTGCTAC AATGGTGTTT ACAGAGGGAA    1200
GCAAGACGGC GACGTGGAGC AAATCCCTAA AAGACATCTC AGTTCGGATT GTTCTCTGCA    1260
ACTCGAGAGC ATGAAGTTGG AATCGCTAGT AATCGCGGAT CAGCATGCCG CGGTGAATAC    1320
GTTCTCGGGC CTTGTACACA CTGCCCGTCA CGCCATGGGA GTTGGTTTTA CCTGAAGGTG    1380
GTGAGCTAAC GCAAGAGGCA GCCAACCACG GTAAAATTAG CGACTGGGGT GAAGTCGTAA    1440
```

(2) INFORMATION FOR SEQ ID NO:38:

(i) SEQUENCE CHARACTERISTICS:
        (A) LENGTH: 1441 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

```
CCTGGCTCAG AACGAACGCT ATCGGTATGC TTAACACATG CAAGTCGGAC GGACTAATTG      60
GGGGTTTACT CTAATTAGTT AGTGGCAGAC GGGTGAGTAA CACGTGGGAA TCTGCCCATC     120
AGTACGGAAT AACTTTTAGA AATAAAAGCT AATACCGTAT ATTCTCTACG GAGGAAAGAT     180
TTATCGCTGA TGGATGAGCC CGCGTCAGAT TAGGTAGTTG GTGAGGTAAC GGCTCACCAA     240
GCCGACGATC TGTAGCTGGT CTGAGAGGAT GATCAGCCAC ACTGGGACTG AGACACGGCC     300
CAGACTCCTA CGGGAGGCAG CAGTGGGGAA TATTGGACAA TGGGCGAAAG CCTGATCCAG     360
CAATACCGAG TGAGTGATGA AGGCCCTAGG GTTGTAAAGC TCTTTTAGCA AGGAAGATAA     420
TGACGTTACT TGCAGAAAAA GCCCCGGCTA ACTCCGTGCC AGCAGCCGCG GTAAGACGGA     480
GGGGGCTAGC GTTGTTCGGA ATTACTGGGC GTAAAGAGTG CGTAGGCGGT TTAGTAAGTT     540
GGAAGTGAAA GCCCGGGGCT TAACCTCGGA ATTGCTTTCA AAACTACTAA TCTAGAGTGT     600
AGTAGGGGAT GATGGAATTC CTAGTGTAGA GGTGAAATTC TTAGATATTA GGAGGAACAC     660
CGGTGGCGAA GGCGGTCATC TGGGCTACAA CTGACGCTGA TGCACGAAAG CGTGGGGAGC     720
AAACAGGATT AGATACCCTG GTAGTCCACG CCGTAAACGA TGAGTGCTAG ATATCGGAAG     780
ATTTTCTTTC GGTTTCGCAG CTAACGCATT AAGCACTCCG CCTGGGGAGT ACGGTCGCAA     840
GATTAAAACT CAAAGGAATT GACGGGGGCT CGCACAAGCG GTGGAGCATG CGGTTTAATT     900
CGATGTTACG CGAAGAACCT TACCAACCCT TGACATGGTG GTTGCGGATC GCAGAGATGC     960
TTTCCTTCAG CTCGGCTGGA CCACACACAG GTGTTGCATG GCTGTCGTCA GCTCGTGTCG    1020
TGAGATGTTG GGTTAAGTCC CGCAACGAGC GCAACCCTCA TTCTTATTTG CCAGCGGGTA    1080
ATGCCGGGAA CTATAAGAAA CTGCCGGTG ATAAGCCGGA GGAAGGTGGG GACGACGTCA     1140
AGTCATCATG GCCCTTACGG GTTGGGCTAC ACGCGTGCTA CAATGGTGTT TACAGAGGGA    1200
AGCAAGACGG CGACGTGGAG CAAATCCCTA AAAGACATCT CAGTTCGGAT TGTTCTCTGC    1260
AACTCGAGAG CATGAAGTTG GAATCGCTAG TAATCGCGGA TCAGCATGCC GCGGTGAATA    1320
CGTTCTCGGG CCTTGTACAC ACTGCCCGTC ACGCCATGGG AGTTGGTTTT ACCTGAAGGT    1380
GGTGAGCTAA CGCAAGAGGC AGCCAACCAC GGTAAAATTA GCGACTGGGG TGAAGTCGTA    1440
A                                                                   1441
```

(2) INFORMATION FOR SEQ ID NO:39:

(i) SEQUENCE CHARACTERISTICS:
        (A) LENGTH: 1440 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

CCTGGCTCAG AACGAACGCT ATCGGTATGC TTAACACATG CAAGTCGGAC GGACTGATTG    60

GGGTTTTCTC CAGTTAGTGA GTGGCGAACG GGTGAGTAAC ACGTGGGAAT CTGCCCATCA   120

GTACGGAATA ACTTTTAGAA ATAAAAGCTA ATACCGTATA TTCTCTACGG AGGAAAGATT   180

TATCGCTGAT GGATGAGCCC GCGTCGGATT AGGTAGTTGG TGAGGTAACG GCTCACCAAG   240

CCGACGATCT GTAGTTGGTC TGAGAGGATG ATCAGCCACA CTGGGACTGA GACACGGCCC   300

AGACTCCTAC GGGAGGCAGC AGTGGGGAAT ATTGGACAAT GGGCGAAAGC CTGATCCAGC   360

AATACCGAGT GAGTGATGAA GGCCCTAGGG TTGTAAAGCT CTTTTAGCAA GGAAGATAAT   420

GACGTTACTT GCAGAAAAAG CCCCGGCTAA CTCCGTGCCA GCAGCCGCGG TAAGACGGAG   480

GGGGCTAGCG TTGTTCGGAA TTACTGGGCG TAAAGAGTGC GTAGGCGGTT TAGTAAGTTG   540

GAAGTGAAAG CCCGGGGCTT AACCTCGGAA TTGCTTTCAA AACTACTAAT CTAGAGTGTA   600

GTAGGGGATG ATGGAATTCC TAGTGTAGAG GTGAAATTCT TAGATATTAG GAGGAACACC   660

GGTGGCGAAG GCGGTCATCT GGGCTACGAC TGACGCTGAT GCACGAAAGC GTGGGGAGCA   720

AACAGGATTA GATACCCTGG TAGTCCACGC CGTAAACGAT GAGTGCTAGA TATCGGAAGA   780

GTCTCTTTCG GTTTCGCAGC TAACGCATTA AGCACTCCGC CTGGGGAGTA CGGTCGCAAG   840

ATTAAAACTC AAAGGAATTG ACGGGGCTC GCACAAGCGG TGGAGCATGC GGTTTAATTC   900

GATGTTACGC GAAAAACCTT ACCAACCTTT GACATGGTGG TTGCGGATCG CAGAGATGCT   960

TTCCTTCAGT TCGGCTGGAC CACACACAGG TGTTGCATGG CTGTCGTCAG CTCGTGTCGT  1020

GAGATGTTGG GTTAAGTCCC GCAACGAGCG CAACCCTCAT TCTTATTTGC CAGCGGGTAA  1080

TGCCGGGAAC TATAAGAAAA CTGCCGGTGA TAAGCCGGAG GAAGGTGGGG ACGACGTCAA  1140

GTCATCATGG CCCTTATGGG TTGGGCTACA CGCGTGCTAC AATGGTGTTT ACAGAGGGAA  1200

GCAAGACGGT AACGTGGAGC AAATCCCTAA AAGACATCTC AGTTCGGATT GTTCTCTGCA  1260

ACTCGAGAGC ATGAAGTTGG AATCGCTAGT AATCGCGGAT CAGCATGCCG CGGTGAATAC  1320

GTTCTCGGGC CTTGTACACA CTGCCCGTCA CGCCATGGGA GTTGGTTTTA CCTGAAGGTG  1380

GTGAGCTAAC GCAAGAGGCA GCCAACCACG GTAGAATTAG CGACTGGGGT GAAGTCGTAA  1440

(2) INFORMATION FOR SEQ ID NO:40:

(i) SEQUENCE CHARACTERISTICS:
        (A) LENGTH: 1408 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

CGCTATCGGT ATGCTTAACA CATGCAAGTC GGACGGACTA ATTGGGCTT GCTCCAATTA    60

GTTAGTGGCA GACGGGTGAG TAACACGTGG GAATCTACCC ATCAGTACGG AATAACTTTT   120

AGAAATAAAA GCTAATACCG TATATTCTCT ACAGAGGAAA GATTTATCGC TGATGGATGA   180

GCCCGCGTCA GATTAGGTAG TTGGTGAGGT AACGGCTCAC CAAGCCGACG ATCTGTAGCT   240

GGTCTGAGAG GATGATCAGC CACACTGGGA CTGAGACACG GCCCAGACTC CTACGGGAGG   300

CAGCAGTGGG GAATATTGGA CAATGGGCGA AAGCCTGATC CAGCAATACC GAGTGAGTGA   360

```
TGAAGGCCCT AGGGTTGTAA AGCTCTTTTA GCAAGGAAGA TAATGACGTT ACTTGCAGAA      420

AAAGCCCCGG CTAACTCCGT GCCAGCAGCC GCGGTAAGAC GGAGGGGGCT AGCGTTGTTC      480

GGAATTACTG GGCGTAAAGA GTGCGTAGGC GGTTTAGTAA GTTGGAAGTG AAAGCCCGGG      540

GCTTAACCTC GGAATTGCTT TCAAAACTAC TAATCTAGAG TGTAGTAGGG GATGATGGAA      600

TTCCTAGTGT AGAGGTGAAA TTCTTAGATA TTAGGAGGAA CACCGGTGGC GAAGGCGGTC      660

ATCTGGGCTA CAACTGACGC TGATGCACGA AAGCGTGGGG AGCAAACAGG ATTAGATACC      720

CTGGTAGTCC ACGCCGTAAA CGATGAGTGC TAGATATCGG AAGATTCTCT TTCGGTTTCG      780

CAGCTAACGC ATTAAGCACT CCGCCTGGGG AGTACGGTCG CAAGATTAAA ACTCAAAGGA      840

ATTGACGGGG GCTCGCACAA GCGGTGGAGC ATGCGGTTTA ATTCGATGTT ACGCGAAAAA      900

CCTTACCAAC CCTTGACATG GTGGTCGCGG ATCGCAGAGA TGCTTTCCTT CAGCTCGGCT      960

GGACCACACA CAGGTGTTGC ATGGCTGTCG TCAGCTCGTG TCGTGAGATG TTGGGTTAAG     1020

TCCCGCAACG AGCGCAACCC TCATTCTTAT TTGCCAGCGG GTAATGCCGG GAACTATAAG     1080

AAAACTGCCG GTGATAAGCC GGAGGAAGGT GGGGACGACG TCAAGTCATC ATGGCCCTTA     1140

CGGGTTGGGC TACACGCGTG CTACAATGGT GTTTACAGAG GGAAGCAAGA CGGCGACGTG     1200

GAGCAAATCC CTAAAAGACA TCTCAGTTCG GATTGTTCTC TGCAACTCGA GAGCATGAAG     1260

TTGGAATCGC TAGTAATCGC GGATCAGCAT GCCGCGGTGA ATACGTTCTC GGGCCTTGTA     1320

CACACTGCCC GTCACGCCAT GGGAGTTGGT TTTACCTGAA GGTGGTGAGC TAACGCAAGA     1380

GGCAGCCAAC CACGGTAAAA TTAGCGAC                                       1408

(2) INFORMATION FOR SEQ ID NO:41:

(i) SEQUENCE CHARACTERISTICS:
            (A) LENGTH: 1440 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:41:

CCTGGCTCAG AACGAACGCT ATCGGTATGC TTAACACATG CAAGTCGAAC GGACTAATTG       60

GGGCTTGCTC CAATTAGTTA GTGGCAGACG GGTGAGTAAC ACGTGGGAAT CTGCCCATCA      120

GTACGGAATA ACTTTTAGAA ATAAAAGCTA ATACCGTATA TTCTCTACGG AGGAAAGATT      180

TATCGCTGAT GGATGAGCCC GCGTCAGATT AGGTAGTTGG TGAGGTAATG GCTCACCAAG      240

CCTACGATCT GTAGCTGGTC TGAGAGGATG ATCAGCCACA CTGGGACTGA GACACGGCCC      300

AGACTCCTAC GGGAGGCAGC AGTGGGGAAT ATTGGACAAT GGGCGAAAGC CTGATCCAGC      360

AATACCGAGT GAGTGATGAA GGCCCTAGGG TTGTAAAGCT CTTTTAGCAA GGAAGATAAT      420

GACGTTACTT GCAGAAAAAG CCCCGGCTAA CTCCGTGCCA GCAGCCGCGG TAAGACGGAG      480

GGGGCTAGCG TTGTTCGGAA TTACTGGGCG TAAAGAGTGC GTAGGCGGTT TAGTAAGTTG      540

GAAGTGAAAG CCCGGGGCTT AACCTCGGAA TTGCTTTCAA AACTACTAAT CTAGAGTGTA      600

GTAGGGGATG ATGGAATTCC TAGTGTAGAG GTGAAATTCT TAGATATTAG GAGGAACACC      660

GGTGGCGAAG GCGGTCATCT GGGCTACAAC TGACGCTGAT GCACGAAAGC GTGGGGAGCA      720

AACAGGATTA GATACCCTGG TAGTCCACGC CGTAAACGAT GAGTGCTAGA TATTGGGAGA      780

TTTTCTCTCG GTTTCGCAGC TAACGCATTA AGCACTCCGC CTGGGAGTA CGGTCGCAAG      840

ATTAAAACTC AAAGGAATTG ACGGGGGCTC GCACAAGCGG TGGAGCATGC GGTTTAATTC      900
```

```
GATGTTACGC GAAAAACCTT ACCAACCCTT GACATGGTGG TCGCGGATCG CAGAGATGCT      960

TTCCTTCAGT TCGGCTGGAC CACACACAGG TGTTGCATGG CTGTCGTCAG CTCGTGTCGT     1020

GAGATGTTGG GTTAAGTCCC GCAACGAGCG CAACCCTCAT TCTTATTTGC CAGCGGGTAA     1080

TGCCGGGAAC TATAAGAAAA CTGCCGGTGA TAAGCCGGAG GAAGGTGGGG ACGACGTCAA     1140

GTCATCATGG CCCTTACGGG TTGGGCTACA CGCGTGCTAC AATGGTGTTT ACAGAGGGAA     1200

GCAAGACGGC GACGTGGAGC AAATCCCTAA AAGACATCTC AGTTCGGATT GTTCTCTGCA     1260

ACTCGAGAGC ATGAAGTTGG AATCGCTAGT AATCGCGGAT CAGCATGCCG CGGTGAATAC     1320

GTTCTCGGGC CTTGTACACA CTGCCCGTCA CGCCATGGGA GTTGGTTTTA CCTGAAGGTG     1380

GTGAGCTAAC GCAAGAGGCA GCCAACCACG GTAAAATTAG CGACTGGGGT GAAGTCGTAA     1440

(2) INFORMATION FOR SEQ ID NO:42:

(i) SEQUENCE CHARACTERISTICS:
        (A) LENGTH: 1439 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

AGAGTTTGAT CCTGGCTCAG AACGAACGCT ATCGGTATGC TTAACACATG CAAGTCAAAC       60

GGACTAATTG GGGCTTGCTC CAATTAGTTA GTGGCAGACG GGTGAGTAAC ACGTGGGAAT      120

CTCCCCATCA GTACGGAATA ACTTTTAGAA ATAAAAGCTA ATACCGTATA TTCTCTACGG      180

AGGAAAGATT TATCGCTGAT GGATGAGCCC GCGTCAGATT AGGTAGTTGG TGAGGTAATG      240

GCTCACCAAG CCTACGATCT GTAGCTGGTC TGAGAGGATG ATCAGCCACA CTGGGACTGA      300

GACACGGCCC AGACTCCTAC GGGAGGCAGC AGTGGGGAAT ATTGGACAAT GGGCGAAACG      360

NTGATCCAGC AATACCGAGT GAGTGATGAA GGCCTTAGGG TTGTAAAGCT CTTTTAGCAA      420

GGAAGATAAT GACGTTACTT GCAGAAAAAG TCCCGNCTAA CTCCGTGCCA GCAGCCGCGG      480

TAAGACGGAG GGGGCTAGCG TTGTTCGGAA TTACTGGGCG TAAAGAGTGC GTAGGCGGTT      540

TAGTAAGTTG GAAGTGAAAG CCCGGGGCTT AACCTCGGAA TTGCTTTCAA AACTACTAAT      600

CTAGAGTGTA GTAGGGGATG ATGGAATTCC TAGTGTAGAG GTGAAATTCT TAGATATTAG      660

GAGGAACACC GGTGGCGAAG GCGGTCATCT GGNCTACAAC TGACGCTNAT GCACGAAAGC      720

GTGGGGAGCA AACAGGATTA GATACCCTGG TAGTCCACGC CGTAAACGAT GAGTGCTAGA      780

TATCGGAGAA TCTCTCTCGG TTTCGCACGT AACGCATTAA GCACTCCGCC TGGGGAGTAC      840

GGTCGCAAGA TTAAAACTCA AAGGAATTGA CGGGGGCTCG CACAAGCGGT GGAGCATGCG      900

GTTTAATTCG ATGTTACGCG AAAAACCTTA CCAACCCTTG ACATGGTGGT CGCGGATCGC      960

AGAGATGCTT TCCTTCAGTT CGGCTGGACC ACACACAGGT GTTGCATGGC TGTCGTCAGC     1020

TCGTGTCGTG AGATGTTGGG TTAAGTCCCG CAACGAGCGC AACCCTCATT CTTATTTGCC     1080

AGCGGGTAAT GCCAGGAACT ATAAGAAAAC TGCCGGTGAT AAGCCGAGAA GGTGGGGACG     1140

ACGTCAAGTC ATCATGGCCC TTACGGGTTG GCTGCACGC GTGCTACAAT GGTGTTTACA      1200

GAGGGAAGCA AGACGGCGAC GTGGAGCAAA TCCCTAAAAG ACATCTCAGT TCGGATTGCT     1260

CTCTGCAACT CGAGAGCATG AAGTTGGAAT CGCTAGTAAT CGCGGATCAG CATGCCGCGG     1320

TGAATACGTT CTCGGGCCTT GTACACACTG CCCGTCACGC CATGGGAGTT GGTTTTACCT     1380

GAAGGTGGTG GGCTAACCGC AAGAGGCAGC CAACCACGGT AAAATTAGCG ACTGGGGTG     1439
```

(2) INFORMATION FOR SEQ ID NO:43:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

```
CCTGGCTCAG AACGAACGCT ATCGGTATGC TTAACACATG CAAGTCGAAC GGACTAATTA    60
GGGCTTGCTC TAATTAGTTA GTGGCAGACG GGTGAGTAAC ACGTGGGAAT CTGCCCATCA   120
GTACGGAATA ACTTTTAGAA ATAAAAGCTA ATACCGTATA TTCTCTACAG AGGAAAGATG   180
TATCGCTGAT GGATGAGCCC GCGTCAGATT AGGTAGTTGG TGAGGTAATG GCTCACCAAG   240
CCAACGATCT GTAGCTGGTC TGAGAGGATG ATCAGCCACA CTGGGACTGA GACACGGCCC   300
AGACTCCTAC GGGAGGCAGC AGTGGGGAAT ATTGGACAAT GGGCGAAAGC CTGATCCAGC   360
AATACCGAGT GAGTGATGAA GGCCTTAGGG TTGTAAAGCT CTTTTAGCAA GGAAGATAAT   420
GACGTTACTT GCAGAAAAAG CCCCGGCTAA CTCCGTGCCA GCAGCCGCGG TAAGACGGAG   480
GGGGCTAGCG TTGTTCGGAA TTACTGGGCG TAAAGAGTGC GTAGGCGGTT TAGTAAGTTG   540
GAAGTGAAAG CCCGGGGCTT AACCTCGGAA TTGCTTTCAA AACTACTAAT CTAGAGTGTA   600
GTAGGGGATG ATGGAATTCC TAGTGTAGAG GTGAAATTCT TAGATATTAG GAGGAACACC   660
GGTGGCGAAG GCGATCATCT AGGCTATAAC TGACGCTGAT GCACGAAAGC GTGGGGAGCA   720
AACAGGATTA GATACCCTGG TAGTCCACGC CGTAAACGAT GAGTGCTAGA TATCGGGAGA   780
ATATCTCTCG GTTTCGCAGC TAACGCATTA AGCACTCCGC CTGGGGAGTA CGGTCGCAAG   840
ATTAAAACTC AAAGGAATTG ACGGGGCTC GCACAAGCGG TGGAGCATGC GGTTTAATTC    900
GATGTTACGC GAAAAACCTT ACCAACCCTT GACATGGTGG TCGCGGATTG CAGAGATGCT   960
TTCCTTCAGT TCGGCTGGAC CACACACAGG TGTTGCATGG CTGTCGTCAG CTCGTGTCGT  1020
GAGATGTTGG GTTAAGTCCC GCAACGAGCG CAACCCTCAT TCTTATTTGC CAGCGGATAA  1080
TGCCGGGAAC TATAAGAAAA CTGCCAGTGA TAAGCTGGAG GAAGGTGGGG ACGACGTCAA  1140
GTCATCATGG CCCTTACGGG TTGGGCTACA CGCGTGCTAC AATGGTGTTT ACAGAGGGAA  1200
GCAAAACGGC GACGTGGAGC AAATCCCTAA AAGACATCTC AGTTCGGATT GTTCTCTGCA  1260
ACTCGAGAGC ATGAAGTTGG AATCGCTAGT AATCGCGGAT CAGCATGCCG CGGTGAATAC  1320
GTTCTCGGGC CTTGTACACA CTGCCCGTCA CGCCATGGGA GTTGGTTTTA CCTGAAGGTG  1380
GTGAGCTAAC GCAAGAGGCA GCCAACCACG GTAAAATTAG CGACTGGGGT GAAGTCGTAA  1440
```

(2) INFORMATION FOR SEQ ID NO:44:

(i) SEQUENCE CHARACTERISTICS:
        (A) LENGTH: 1508 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

```
GACAGAATCA AACTTGAGAG TTTGATCCTG GCTCAGAACG AACGCTATCG GTATGCTTAA    60
CACATGCAAG TCGAACGGAT TAACTAGAGC TCGCTTTAGT TAATTAGTGG CAGACGGGTG   120
AGTAACACGT GGGAATCTAC CCATCAGTAC GGAATAACTT TTAGAAATAA AGCTAATAC    180
CGTATATTCT CTACGGAGGA AAGATTTATC GCTGATGGAT GGGCCCGCGT CAGATTAGGT   240
```

```
AGTTGGTGAG GTAATGGCTC ACCAAGCCGA CGATCTGTAG CTGGTCTGAG AGGATGATCA      300

GCCACACTGG GACTGAGACA CGGCCCAGAC TCCTACGGGA GGCAGCAGTG GGGAATATTG      360

GACAATGGGC GAAAGCCTGA TCCAGCAATA CCGAGTGAGT GATGAAGGCC TTAGGGTTGT      420

AAAGCTCTTT TAGCAAGGAA GATAATGACG TTACTTGCAG AAAAAGCCCC GGCTAACTCC      480

GTGCCAGCAG CCGCGGTAAG ACGGAGGGGG CTAGCGTTGT TCGGAATTAC TGGGCGTAAA      540

GAGTGCGTAG GCGGTTTAGT AAGTTGGAAG TGAAAGCCCG GGGCTTAACC TCGGAATTGC      600

TTTCAAAACT ACTAATCTAG AGTGTAGTAG GGGATGATGG AATTCCTAGT GTAGAGGTGA      660

AATTCTTAGA TATTAGGAGG AACACCGGTG GCGAAGGCGG TCATCTGGGC TACAACTGAC      720

GCTGATGCAC GAAAGCGTGG GGAGCAAACA GGATTAGATA CCCTGGTAGT CCACGCCGTA      780

AACGATGAGT GCTAGATATC GGAGGATTCT CTTTCGGTTT CGCAGCTAAC GCATTAAGCA      840

CTCCGCCTGG GGAGTACGGT CGCAAGATTA AAACTCAAAG GAATTGACGG GGGCTCGCAC      900

AAGCGGTGGA GCATGCGGTT TAATTCGATG TTACGCGAAA AACCTTACCA ACCCTTGACA      960

TGGTGGTTAC GGATTGCAGA GATGCTTTCC TTCAGTTCGG CTGGGCCACA CACAGGTGTT     1020

GCATGGCTGT CGTCAGCTCG TGTCGTGAGA TGTTGGGTTA AGTCCCGCAA CGAGCGCAAC     1080

CCTTATTCTT ATTTGCCAGT GGGTAATGCC GGGAACTATA AGAAAACTGC CGGTGATAAG     1140

CCGGAGGAAG GTGGGGACGA CGTCAAGTCA TCATGGCCCT TACGGGTTGG GCTACACGCG     1200

TGCTACAATG GTGTTTACAG AGGGAAGCAA TACGGTGACG TGGAGCAAAT CCCTAAAAGA     1260

CATCTCAGTT CGGATTGTTC TCTGCAACTC GAGAGCATGA AGTTGGAATC GCTAGTAATC     1320

GCGGATCAGC ATGCCGCGGT GAATACGTTC TCGGGCCTTG TACACACTGC CCGTCACGCC     1380

ATGGGAGTTG GTTTTACCTG AAGGTGGTGA GCTAACGCAA GAGGCAGCCA ACCACGGTAA     1440

AATTAGCGAC TGGGGTGAAG TCGTAACAAG GTAGCCGTAG GGGAACCTGC GGCTGGATTA     1500

CCTCCTTA                                                              1508

(2) INFORMATION FOR SEQ ID NO:45:

(i) SEQUENCE CHARACTERISTICS:
            (A) LENGTH: 1458 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:45:

CAAACTTGAG AGTTTGATCC TGGCTCAGAA CGAACGCTAT CGGTATGCTT AACACATGCA       60

AGTCGAACGG ATTAATTAGA GCTTGCTCTA GTTAATTAGT GGCAGACGGG TGAGTAACAC      120

GTGGGAATCT ACCCATCAGT ACGGAATAAC TTTTAGAAAT AAAAGCTAAT ACCGTATATT      180

CTCTACGGAG GAAAGATTTA TCGCTGATGG ATGGGCCCGC GTCAGATTAG GTAGTTGGTG      240

TGGTAATGGC TCACCAAGCC GACGATCTGT AGCTGGTCTG AGAGGATGAT CAGCCACACT      300

GGGACTGAGA CACGGCCCAG ACTCCTACGG GAGGCAGCAG TGGGGAATAT TGGACAATGG      360

GCGAAAGCCT GATCCAGCAA TACCGAGTGA GTGATGAAGG CCTTAGGGTT GTAAAGCTCT      420

TTTAGCAAGG AAGATAATGA CGTTACTTGC AGAAAAAGCC CCGGCTAACT CCGTGCCAGC      480

AGCCGCGGTA AGACGGAGGG GGCTAGCGTT GTTCGGAATT ACTGGGCGTA AGAGTGCGT      540

AGGTGGTTTA GTAAGTTGGA AGTGAAAGCC CGGGGCTTAA CCTCGGAATT GCTTTCAAAA      600

CTACTAATCT AGAGTGTAGT AGGGGATGAT GGAATTCCTA GTGTAGAGGT GAAATTCTTA      660
```

```
GATATTAGGA GGAACACCGG TGGCGAAGGC GGTCATCTGG GCTACAACTG ACGCTGATGC      720

ACGAAAGCGT GGGGAGCAAA CAGGATTAGA TACCCTGGTA GTCCACGCCG TAAACGATGA      780

GTGCTAGATA TCGGAGGATT CTCTTTCGGT TTCGCAGCTA ACGCATTAAG CACTCCGCCT      840

GGGGAGTACG GTCGCAAGAT TAAAACTCAA AGGAATTGAC GGGGGCTCGC ACAAGCGGTG      900

GAGCATGCGG TTTAATTCGA TGTTACGCGA AAAACCTTAC CAACCCTTGA CATGGTGGTT      960

ATGGATTGCA GAGATGCTTT CCTTCAGTTC GGCTGGGCCA CACACAGGTG TTGCATGGCT     1020

GTCGTCAGCT CGTGTCGTGA GATGTTGGGT TAAGTCCCGC AACGAGCGCA ACCCTTATTC     1080

TTATTTGCCA GCGGGTAATG CCGGGAACTA TAAGAAAACT GCCGGTGATA AGCCGGAGGA     1140

AGGTGGGGAC GACGTCAAGT CATCATGGCC CTTACGGGTT GGGCTACACG CGTGCTACAA     1200

TGGTGTTTAC AGAGGGAAGC AAGACGGTGA CGTGGAGCAA ATCCCTAAAA GACATCTCAG     1260

TTCGGATTGT TCTCTGCAAC TCGAGAGCAT GAAGTTGGAA TCGCTAGTAA TCGCGGATCA     1320

GCATGCCGCG GTGAATACGT TCTCGGGCCT TGTACACACT GCCCGTCACG CCATGGGAGT     1380

TGGTTTTACC TGAAGGTGGT GAGCTAACGC AAGAGGCAGC CAACCACGGT AAAATTAGCG     1440

ACTGGGGTGA AGTCGTAA                                                  1458

(2) INFORMATION FOR SEQ ID NO:46:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

CCTGGCTCAG AACGAACGCT ATCGGTATGC TTAACACATG CAAGTCGAAC GGATTAATTA       60

GAGCTTGCTC TAGTTAATTA GTGGCAGACG GGTGAGTAAC ACGTGGGAAT CTACCCATCA      120

GTACGGAATA ACTTTTAGAA ATAAAAGCTA ATACCGTATA TTCTCTACGG AGGAAAGATT      180

TATCGCTGAT GGATGGGCCC GCGTCAGATT AGGTAGTTGG TGTGGTAATG GCTCACCAAG      240

CCGACGATCT GTAGCTGGTC TGAGAGGATG ATCAGCCACA CTGGGACTGA GACACGGCCC      300

AGACTCCTAC GGGAGGCAGC AGTGGGGAAT ATTGGACAAT GGGCGAAAGC CTGATCCAGC      360

AATACCGAGT GAGTGATGAA GGCCTTAGGG TTGTAAAGCT CTTTTAGCAA GGAAGATAAT      420

GACGTTACTT GCAGAAAAAG CCCCGGCTAA CTCCGTGCCA GCAGCCGCGG TAAGACGGAG      480

GGGGCTAGCG TTGTTCGGAA TTACTGGGCG TAAAGAGTGC GTAGGTGGTT TAGTAAGTTG      540

GAAGTGAAAG CCCGGGCTT AACCTCGGAA TTGCTTTCAA AACTACTAAT CTAGAGTGTA       600

GTAGGGGATG ATGGAATTCC TAGTGTAGAG GTGAAATTCT TAGATATTAG GAGGAACACC      660

GGTGGCGAAG GCGGTCATCT GGGCTACAAC TGACGCTGAT GCACGAAAGC GTGGGGAGCA      720

AACAGGATTA GATACCCTGG TAGTCCACGC CGTAAACGAT GAGTGCTAGA TATCGGAGGA      780

TTCTCTTTCG GTTTCGCAGC TAACGCATTA AGCACTCCGC CTGGGGAGTA CGGTCGCAAG      840

ATTAAAACTC AAAGGAATTG ACGGGGCTC GCACAAGCGG TGGAGCATGC GGTTTAATTC       900

GATGTTACGC GAAAAACCTT ACCAACCCTT GACATGGTGG TTATGGATTG CAGAGATGCT      960

TTCCTTCAGT TCGGCTGGGC CACACACAGG TGTTGCATGG CTGTCGTCAG CTCGTGTCGT     1020

GAGATGTTGG GTTAAGTCCC GCAACGAGCG CAACCCTTAT TCTTATTTGC CAGCGGGTAA     1080

TGCCGGGAAC TATAAGAAAA CTGCCGGTGA TAAGCCGGAG GAAGGTGGGG ACGACGTCAA     1140

GTCATCATGG CCCTTACGGG TTGGGCTACA CGCGTGCTAC AATGGTGTTT ACAGAGGGAA     1200
```

```
GCAAGACGGT GACGTGGAGC AAATCCCTAA AAGACATCTC AGTTCGGATT GTTCTCTGCA    1260

ACTCGAGAGC ATGAAGTTGG AATCGCTAGT AATCGCGGAT CAGCATGCCG CGGTGAATAC    1320

GTTCTCGGGC CTTGTACACA CTGCCCGTCA CGCCATGGGA GTTGGTTTTA CCTGAAGGTG    1380

GTGAGCTAAC GCAAGAGGCA GCCAACCACG GTAAAATTAG CGACTGGGGT GAAGTCGTAA    1440
```

(2) INFORMATION FOR SEQ ID NO:47:

(i) SEQUENCE CHARACTERISTICS:
        (A) LENGTH: 1569 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

```
TTTACGTTTC TTATATTTGT TTTTTTGCAT GAGTCCAAGC CATAAGTAAT TATGGTTTTG      60

TCAAACTTGA GAGTTTGATC CTGGCTCAGA ACGAACGCTG GCGGCAAGCT TAACACATGC     120

AAGTCGAACG GACAGTTATT TATAGCTTCG GCTATGAGTA TCTGTTAGTG GCAGACGGGT     180

GAGTAATGCG TAGGAATCTG CCTAGTAGTA TGGAATAGCT ATTAGAAATG ATAGGTAATA     240

CTGTATAATC CCTGCGGGGG AAAGATTTAT CGCTATTAGA TGAGCCTACG TTAGATTAGC     300

TAGTTGGTAA GGTAATGGCT TACCAAGGCA ATGATCTATA GCTGGTCTGA GAGGACGATC     360

AGCCACACTG GAACTGAGAT ACGGTCCAGA CTCCTACGGG AGGCAGCAGT GGGGAATATT     420

GGACAATGGG CGAAAGCCTG ATCCAGCTAT GCCGCGTGAG TGAAGAAGGC CTTCGGGTTG     480

TAAAACTCTT TTAATAGGGA AGATAATGAC GGTACCTATA GAAAAAGTCC CGGCAAACTC     540

CGTGCCAGCA GCCGCGGTAA TACGGAGGGG GCAAGCGTTG TTCGGAATTA TTGGGCGTAA     600

AGGGCACGTA GGTGGACTAG TAAGTTAAAA GTGAAATACC AAAGCTCAAC TTTGGAGCTG     660

CTTTTAATAC TGCTAGACTA GAGGTCGAGA GAGGATAGCG GAATTCCTAG TGTAGAGGTG     720

AAATTCGTAG ATATTAGGAG GAACACCGGT GGCGAAGGCG GCTATCTGGC TCGATACTGA     780

CACTGAGGTG CGAAAGCGTG GGGAGCAAAC AGGATTAGAT ACCCTGGTAG TCCACGCTGT     840

AAACGATGAG TGCTAAATGT GAGGATTTTA TCTTTGTATT GTAGCTAACG CGTTAAGCAC     900

TCCGCCTGGG GACTACGGTC GCAAGACTAA AACTCAAAGG AATTGACGGG GACCCGCACA     960

AGCGGTGGAG CATGTGGTTT AATTCGATGC AACGCGAAAA ACCTTACCAC TTTTTGACAT    1020

GAAGGTCGTA TCCCTTTTAA CCGAGGGAGT CAGTTCGGCT GGACCTTACA CAGGTGCTGC    1080

ATGGCTGTCG TCAGCTCGTG TCGTGAGATG TTGGGTTAAG TCCCGCAACG AGCGCAACCC    1140

TCATCCTTAG TTACCAACAG GTAATGCTGG GCACTCTAAG GAAACTGCCA GTGATAAACT    1200

GGAGGAAGGT GGGGATGATG TCAAGTCAGC ACGGCCCTTA TAGGGTGGGC TACACACGTG    1260

CTACAATGGC AACTACAATA GGTTGCGAGA CCGCGAGGTT TAGCTAATCC AAAAAAGTTG    1320

TCTCAGTTCG GATTGTTCTC TGCAACTCGA GAGCATGAAG TCGGAATCGC TAGTAATCGT    1380

GGATCATCAT GCCACGGTGA ATACGTTCTC GGGTCTTGTA CACACTGCCC GTCACGCCAT    1440

GGGAATTGGC TTAACTCGAA GCTGGTGTGC TAACCGTAAG GAAGCAGCCA TTTAAGGTTG    1500

GGTTAGTGAC TAGGGTGAAG TCGTAACAAG GTAGCTGTAG GTGAACCTGC GGCTGGATTA    1560

CCTCCTTTT                                                              1569
```

(2) INFORMATION FOR SEQ ID NO:48:

(i) SEQUENCE CHARACTERISTICS:

(A) LENGTH: 1435 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

CTCAGAACGA ACGCTGGCGG CAAGCCTAAC ACATGCAAGT CGAACGGACA ATTGCTTATA      60

ACCTTTTGGT TATAAATAAT TGTTAGTGGC AGACGGGTGA GTAATGCGTA GGAATCTACC     120

TAGTAGTATG GAATAGCCAT TAGAAATGAT GGGTAATACT GTATAATCCC TGCGGGGGAA     180

AGATTTATCG CTATTAGATG AGCCTACGTT AGATTAGCTA GTTGGTAAGG TAATGGCTTA     240

CCAAGGCTAT GATCTATAGC TGGTCTGAGA GGACGATCAG CCACACTGGA ACTGAGATAC     300

GGTCCAGACT CCTACGGGAG GCAGCAGTGG GGAATATTGG ACAATGGGCG AAAGCCTGAT     360

CCAGCTATGC CGCGTGAGTG AAGAAGGCCT TCGGGTTGTA AAACTCTTTC AATAGGGAAG     420

ATAATGACGG TACCTATAGA AGAAGTCCCG GCAAACTCTG TGCCAGCAGC CGCGGTAATA     480

CGGAGGGGGC AAGCGTTGTT CGGAATTATT GGGCGTAAAG GCACGTAGG TGGACTAGTA      540

AGTTAAAAGT GAAATACCAA GGCTTAACTT TGGAGCGGCT TTTAATACTG CTAGACTAGA     600

GGTCGAAAGA GGATAGCGGA ATTCCTAGTG TAGAGGTGAA ATTCGTAGAT ATTAGGAGGA     660

ACACCAGTGG CGAAAGCGGC TATCTGGTTC GATACTGACA CTGAGGTGCG AAAGCGTGGG     720

GAGCAAACAG GATTAGATAC CCTGGTAGTC CACGCTGTAA ACGATGAGTG CTAAATGTGA     780

GGATTTTATC TTTGTATTGT AGCTAACGCG TTAAGCACTC CGCCTGGGGA CTACGGTCGC     840

AAGACTAAAA CTCAAAGGAA TTGACGGGGA CCCGCACAAG CGGTGGAGCA TGTGGTTTAA     900

TTCGATGCAA CGCGAAAAAC CTTACCACTT TTTGACATGA AGGTCGTATC CCTCCTAATA     960

GGGGGAGTCA GTTCGGCTGG ACCTTACACA GGTGCTGCAT GGCTGTCGTC AGCTCGTGTC    1020

GTGAGATGTT GGGTTAAGTC CCGCAACGAG CGCAACCCTC ATCCTTAGTT ACCAACAGGT    1080

AATGCTGGGC ACTCTAAGGA AACTGCCAGT GATAAACTGG AGGAAGGTGG GGATGATGTC    1140

AAGTCAGCAC GGCCCTTATA AGGTGGGCTA CACACGTGCT ACAATGGCAA CTACAATAGG    1200

TCGCGAGACC GCAAGGTTTA GCTAATCCAT AAAAGTTGTC TCAGTTCGGA TTGTTCTCTG    1260

CAACTCGAGA GCATGAAGTC GGAATCGCTA GTAATCGTGG ATCATCATGC CACGGTGAAT    1320

ACGTTCTCGG GTCTTGTACA CACTGCCCGT CACGCCATGG GAATTGGCTT AACTCGAAGC    1380

TGGTGTGCTA ACCGCAAGGA AGCAGCCATT TAAGGTTGGG TTAGTGACTA GGGTG         1435

(2) INFORMATION FOR SEQ ID NO:49:

(i) SEQUENCE CHARACTERISTICS:
        (A) LENGTH: 1494 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

AGAGTTTGAT CCTGGCTCAG AACGAACGCT GGCGGCAAGC TTAACACATG CAAGTCGAAC      60

GGACCGTATA CGCAGCTTGC TGCGTGTATG GTTAGTGGCA GACGGGTGAG TAATGCATAG     120

GAATCTACCT AGTAGTATGG GATAGCCACT AGAAATGGTG GGTAATACTG TATAATCCTG     180

CGGGGGAAAG ATTTATCGCT ATTAGATGAG CCTATGTCAG ATTAGCTAGT TGGTGGGGTA     240

ATGGCCTACC AAGGCGGTGA TCTGTAGCTG GTCTGAGAGG ATGATCAGCC ACACTGGAAC     300

```
TGAGACACGG TCCAGACTCC TACGGGAGGC AGCAGTGGGG AATATTGGAC AATGGGCGCA    360

AGCCTGATCC AGCTATGCCG CGTGAGTGAG GAAGGCCTTA GGGTTGTAAA ACTCTTTCAG    420

TAGGGAAGAT AATGACGGTA CCTACAGAAG AAGTCCCGGC AAACTCCGTG CCAGCAGCCG    480

CGGTAATACG GAGGGGGCAA GCGTTGTTCG GAATTATTGG GCGTAAAGGG CATGTAGGCG    540

GTTTGGTAAG TTAAAGGTGA AATACCAGGG CTTAACCCTG GGGCTGCTTT TAATACTGCA    600

GGACTAGAGT CCGGAAGAGG ATAGCGGAAT TCCTAGTGTA GAGGTGAAAT TCGTAGATAT    660

TAGGAGGAAC ACCAGTGGCG AAGGCGGCTG TCTGGTCCGG TACTGACGCT GAGGTGCGAA    720

AGCGTGGGGA GCAAACAGGA TTAGATACCC TGGTAGTCCA CGCTGTAAAC GATGAGTGCT    780

GAATGTGGGG CTTTTGCCT CTGTGTTGTA GCTAACGCGT TAAGCACTCC GCCTGGGGAC    840

TACGGTCGCA AGACTAAAAC TCAAAGGAAT TGACGGGGAC NCGCACAAGC GGTGGAGCAT    900

GTGGTTTAAT TCGATGCAAC GCGAAAAACC TTACCACTTC TTGACATGGA GGCTAGATCC    960

TTCTTAACAG AAGGGCGCAG TTCGGCTGGG CCTCGCACAG GTGCTGCATG GCTGTCGTCA   1020

GCTCGTGTCG TGAGATGTTG GGTTAAGTCC CGCAACGAGC GCAACCCTCA TCCTTAGTTA   1080

CCAGCGGGTA ATGCCGGGCA CTTTAAGGAA ACTGCCAGTG ATAAACTGGA GGAAGGTGGG   1140

GATGATGTCA AGTCAGCACG GCCCTTATGG GGTGGGCTAC ACACGTGCTA CAATGGCGAC   1200

TACAATAGGT TGCAACGTCG CAAGGCTGAG CTAATCCGTA AAAGTCGTCT CAGTTCGGAT   1260

TGTCCTCTGT AACTCGAGGG CATGAAGTCG GAATCGCTAG TAATCGTGGA TCAGCATGCC   1320

ACGGTGAATA CGTTCTCGGG TCTTGTACAC ACTGCCCGTC ACGCCATGGG AATTGGCTTA   1380

ACTCGAAGCT GGTGCGCCAA CCGTAAGGAG GCAGCCATTT AAGGTTGGGT CGGTGACTGG   1440

GGTGAAGTCG TAACAAGGTA GCTGTAGGTG AACCTGCGGC TGGATCACCT CCTT         1494

(2) INFORMATION FOR SEQ ID NO:50:

(i) SEQUENCE CHARACTERISTICS:
        (A) LENGTH: 1325 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

GCTCAGAATG AACGCTGGCG GCAGGCCTAA CACATGCAAG TCGAACGGAG TTATATTGTA     60

GCTTGCTATG GTATAACTTA GTGGCAGACG GGTGAGTAAT GTATAGGAAT CTACCTAGTA    120

GTACGGAATA ATTGTTGGAA ACGACAACTA ATACCGTATA CGCCCTACGG GGGAAAAATT    180

TATTGCTATT AGATGAGCCT ATATTAGATT AGCTAGTTGG TGGGGTAATA GCCTACCAAG    240

GTAATGATCT ATAGCTGATC TGAGAGGATG ATCAGCCACA CTGGAACTGA GATACGGTCC    300

AGACTCCTAC GGGAGGCAGC AGTGGGGAAT ATTGGACAAT GGGCGAAAGC CTGATCCAGC    360

CATGCCGCAT GAGTGAAGAA GGCCTTTGGG TTGTAAAGCT CTTTTAGTGA GGAAGATAAT    420

GACGGTACTC ACAGAAGAAG TCCTGGCTAA CTCCGTGCCA GCAGCCGCGG TAATACGGAG    480

AGGGCTAGCG TTATTCGGAA TTATTGGGCG TAAAGGGCGC GTAGGCTGGT TAATAAGTTA    540

AAAGTGAAAT CCCGAGGCTT AACCTTGGAA TTGCTTTTAA AACTATTAAT CTAGAGATTG    600

AAAGAGGATA GAGGAATTCC TGATGTAGAG GTAAAATTCG TAAATATTAG GAGGAACACC    660

AGTGGCGAAG GCGTCTATCT GGTTCAAATC TGACGCTGAA GCGCGAAGGC GTGGGGAGCA    720

AACAGGATTA GATACCCTGG TAGTCCACGC TGTAAACGAT GAATGTTAAA TATGGGGAGT    780

TTACTTTCTG TATTACAGCT AACGCGTTAA ACATTCCGCC TGGGGACTAC GGTCGCAAGA    840
```

| TTAAAACTCA AAGGAATTGA CGGGGACCCG CACAAGCGGT GGAGCATGTG GTTTAATTCG | 900 |
| ATGCAACGCG AAAAACCTTA CCACTTCTTG ACATGAAAAT CATACCTATT CGAAGGGATA | 960 |
| GGGTCGGTTC GGCCGGATTT TACACAAGTG TTGCATGGCT GTCGTCAGCT CGTGTCGTGA | 1020 |
| GATGTTGGGT TAAGTCCCGC AACGAGCGCA ACCCTCATCC TTAGTTGCCA TCAGGTAATG | 1080 |
| CTGAGTACTT TAAGGAAACT GCCAGTGATA AGCTGGAGGA AGGTGGGGAT GATGTCAAGT | 1140 |
| CATCATGGCC TTTATGGAGT GGGCTACACA CGTGCTACAA TGGTGTCTAC AATGGGCTGC | 1200 |
| AAGGTGCGCA AGCCTAAGCT AATCCCTAAA AGACATCTCA GTTCGGATTG TACTCTGCAA | 1260 |
| CTCGAGTACA TGAAGTTGGA ATCGCTAGTA ATCGTGGATC AGCATGCCAC GGTGAATACG | 1320 |
| TTCTC | 1325 |

(2) INFORMATION FOR SEQ ID NO:51:

(i) SEQUENCE CHARACTERISTICS:
        (A) LENGTH: 1498 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

| CTGATTTGAG AGTTTGATCC TGGCTCAGAA CGAACGCTAG CGGTAGGCTT AACACATGCA | 60 |
| AGTCGAACGG AATCAGGGCT GCTTGCAGCC TTGGTCCCGT GGCAGACGGG TGCGTAACGC | 120 |
| GTGGGAACTT GCCTGGTAGT AGGGAATAAC CAGTGGAAAC ATTGGGCAAC ACCCTATACG | 180 |
| CCCTGAGGGG GAAAATTTAT TGCTATCAGA TAGGCCCGCG TTAGATTAGC TAGTTGGTGG | 240 |
| GGTAATGGCC TACCAAGGCG ACGATCTATA GCTGGTCTGA GAGGATGATC AGCCACACTG | 300 |
| GAACTGAGAC ACGGTCCAGA CTCCTACGGG AGGCAGCAGT GAGGAATATT GGACAATGGG | 360 |
| CGAAAGCCTG ATCCAGCCAT ACCGCATGAG TGATGAAGGC CCTTGGGTTG TAAAGCTCTT | 420 |
| TTAGTGGGGA AGATAATGAC GGTACCCACA GAAGAAGTCC CGGCTAACTC CGTGCCAGCA | 480 |
| GCCGCGGTAA TACGGAGGGG CTAGCGTTG TTCGGAATTA CTGGGCGTAA AGGGTGCGTA | 540 |
| GGCGGTCCCG TAAGTTAGGT GTGAAATCCT TGGGCTTAAC CCAAGAACTG CATTTAAAAC | 600 |
| TGTGGGACTC GAACGTGAGA GAGGGCAATG GAATTTTTGG TGTAGGGGTG AAATCCGTAG | 660 |
| ATATCAAGAG GAACGTCAGG GGCGAAAGCG ATTGCCTGGA TCACAGTTGA CGCTGAGGCA | 720 |
| CGAAAGCGTG GGGAGCAAAC AGGATTAGAT ACCCTGGTAG TCCACGCTGT AAACGATGAG | 780 |
| TGTTAAAAGT GGGTTATTTT ATCTGCTTTG TAGCTAACGC GTTAAACACT CCGCCTGGGG | 840 |
| ACTACGGTCG CAAGACTAAA ACTCAAAGGA ATTGACGGGG ACTCGCACAA GCGGTGGAGT | 900 |
| ATGTGGTTTA ATTCGATGCA ACGCGAAAAA CCTTACCATA CCTTGACATG TGGATTGTAT | 960 |
| CCCTCTGAAG GGAGGGAGTC AGTTCGGCTG GATCCAACAC AGGTGTTGCA TGGCTGTCGT | 1020 |
| CAGCTCGTGT CGTGAGATGT TGGGTTAAGT CCCGCAACGA GCGCAACCCT CATCCTTAGT | 1080 |
| TGCCAGCGGT TCGGCCGGGA ACTTTAAGGA AACTGCCAGT GACAAGCTGG AGGAAGGTGG | 1140 |
| GGACGACGTC AAGTCATCAT GGCCCTTATG GTATGGGCTA CACACGTACT ACAATGGCAA | 1200 |
| CTACAATGAG CTAGCTACAC CGTAAGGTGA CGCCAATCTC TTAAAGGTTG TCTCAGTACG | 1260 |
| GATTGCCTTC TGCAACTCGA AGGCATGAAG TTGGAATCGC TAGTAATCGC AGATCAGCAT | 1320 |
| GCTGCGGTGA ATACGTTCTC GGGTCTTGTA CACACTGCCC GTCAGGCCAT GGGAGTTCAT | 1380 |
| CTTACTCGAA GCTAGTGAGC TGACCGCAAG GAGGCAGCTA TCTACGGTGG GGTGGGTGAC | 1440 |

TGGGGTTAAG TCGTAACAAG GTAGCCGTAG GTGAACCTGC GGCTGGATTA CCTCCTTT        1498

(2) INFORMATION FOR SEQ ID NO:52:

(i) SEQUENCE CHARACTERISTICS:
        (A) LENGTH: 1415 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

CTCAGAACGA ACGCTGGCGG CAGGCTTAAC ACATGCAAGT CGAGCGCACT CTTTTAGAGT        60

GAGCGGCAAA CGGGTGAGTA ACGCGTGGGA ATCTACCCAT CTCTACGGAA TAACACAGAG       120

AAATTTGTGC TAATACCGTA TACGTCCCTC TGGGAGAAAG ATTTATCGGA GGTGGATGAG       180

CCCGCGTTGG ATTAGCTAGT TGGTGAGGTA AGGGCTCACC AAGGCGACGA TCCATAGCTG       240

GTCTGAGAGG ATGATCAGCC ACACTGGGAC TGAGACACGG CCCAGACTCC TACGGGAGGC       300

AGCAGTGGGG AATATTGGAC AATGGGGCA ACCCTGATCC AGCCATGCCG CGTGAGTGAT        360

GAAGGCCCTA GGGTTGTAAA GCTCTTTCAC CGGTGAAGAT AATGACGTTA ACCGGAGAAG       420

AAGCCCCGGC TAACTTCGTG CCAGCAGCCG CGGTAATACG AAGGGGGCTA GCGTTGTTCG       480

GATTTACTGG GCGTAAAGCG CATGTAGGCG GATATTTAAG TCAGAGGTGA AATCCCAGGG       540

CTCAACCCTG GAACTGCCTT TGATACTGGA TGTCTCGAGT GTGGAAGAGG TGAGTGGAAT       600

TCCGAGTGTA GAGGTAAAAT TCGTAGATAT TCGGAGGAAC ACCAGTGGCG AAGGCGGCTC       660

ACTGGTCCAT TACTGACGCT GAGGTGCGAA AGCGTGGGGA GCAAACAGGA TTAGATACCC       720

TGGTAGTCCA CGCCGTAAAC GATGAATGTT AGCCGTCGGG TGGTTTACTA CTCGGTGGCG       780

CACGTAACGC GTTAAACATT CCGCCTGGGG AGTACGGTCG CAAGATTAAA ACTCAAAGGA       840

ATTGACGGGG GCCCGCACAA GCGTGGAGCA TGTGGTTTAA TTCGAAGCAA CGCGCAGAAC       900

CTTACCAGCC CTTGACATCC CGATCGCGGA AGGTGGAGAC ACCCTCCTTC AGTTAGGCTG       960

GATCGGTGAC AGGTGCTGCA TGGCTGTCGT CAGCTCGTGT CGTGAGATGT TGGGTTAAGT      1020

CCCGCAACGA GCGCAACCCT CGCCCTTAGT TGCCATCATT AAGTTGGGCA CTCTAGGGGG      1080

ACTGCCGGTG ATAAGCCGAG AGGAAGGTGG GGATGACGTC AAGTCCTCAT GGCCCTTACG      1140

GGCTGGGCTA CACACGTGCT ACAATGGTGG TGACAGTGGG CAGCGAGACC GCGAGGTCGA      1200

GCTAATCTCC AAAAGCCATC TCAGTTCGGA TTGCACTCTG CAACTCGAGT GCATGAAGTT      1260

GGAATCGCTA GTAATCGTGG ATCAGCATGC CACGGTGAAT ACGTTCCCGG GCCTTGTACA      1320

CACCGCCCGT CACACCATGG GAGTTGGTTT TACCCGAAGG TGCTGTGCTA ACCGCAAGGA      1380

GGCAGGCAAC CACGGTAGGG TCAGCGACTG GGGTG                                 1415

(2) INFORMATION FOR SEQ ID NO:53:

(i) SEQUENCE CHARACTERISTICS:
        (A) LENGTH: 1484 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

NNATTGAAGA GTTTGATTCT GGCTCAGATT GAACGCTAGC GGCATGCTTA ACACATGCAA        60

GTCGAACGGC AGCGCAGGGA GNCTTNCTCC TGGCGGCGAG AGTGGCGGAC GGGTGAGTAA       120

-continued

| | | | | | |
|---|---|---|---|---|---|
| TGCGTAGGAA | TCTACCTTGT | AGTGGGGGAT | AACCTGGGGA | AACTCGGGCT | AATACCGTAT | 180 |
| AATCTCTTTG | GAGCAAAGCG | GGGGATCTTC | GGACCTCGTG | CTATAAGATG | AGCCTACGTC | 240 |
| GGATTAGCTT | GTTGGTGGGG | TAATGGCCTA | CCAAGGCGAC | GATCCGTAGC | TGGTCTGAGA | 300 |
| GGACGATCAG | CCACACTGGG | ACTGAGACNC | GGCCCAGACT | CCTACGGGAG | GCAGCAGTGG | 360 |
| GGAATATTGG | ACAATGGGGG | AAACCCTGAT | CCAGCAATGC | CGCGTGTGTG | AAGAAGGCCT | 420 |
| TCGGGTTGTA | AAGCACTTTC | GGTGGGGAAG | AAATTCTCAA | GGGTAATATC | CTNGGGCGTT | 480 |
| GACGTTACCC | ACAGAAGAAG | CACTGGCTAA | CTCTGTGCCA | GCAGCCGCGG | TAATACAGAG | 540 |
| AGTGCAAGCG | TTAATCGGAA | TCACTGGGCG | TAAAGCGCGC | GTAGGTGGAT | ATTTAAGTCG | 600 |
| GATGTGAAAG | CCCTGGGCTN | NNCCTGGGAA | TTGCACCCGA | TACTGGGTAT | CTTGAGTATG | 660 |
| GTAGAGGGAA | NTGGAATTTC | CGGTGTAGCG | GTGAAATGCG | TAGATATCGG | AAAGAACACC | 720 |
| AGTGGCGAAG | GCGACTTCCT | GGACCAATAC | TGACACTGAG | GCGCGAAAGC | GTGGGGAGCA | 780 |
| AACAGGATTA | GAGACCCTGG | TAGTCCACGC | NGTCAACGAT | GAGAACTAGC | TGTTGGGAAG | 840 |
| TTCCCTTCTT | AGTAGCGAAG | CTAACGCGTT | AAGTTCTCCG | CCTGGGGAGT | ACGGCCGCAA | 900 |
| GGTTAAAACT | CAAAGAAATT | GACGGGGGCN | CGCACAAGCG | GTGGAGCATG | TGGTTTAATT | 960 |
| CGATGCAACG | CGAAAAACCT | TACCTACCCT | TGACATCCTC | GGAACTTGTC | AGAGATGATT | 1020 |
| TGGTGCCTTC | GGGAACCGAG | TGACAGGTGC | TGCATGGCTG | TCGTCAGCTC | GTGTCGTGAG | 1080 |
| ATGTTGGGTT | AAGTCCCGTA | ACGAGCGCAA | CCCTCGTCCT | TAGTTGCCAG | CGAGTCAAGT | 1140 |
| CGGGAACTCT | AAGGAGACTG | CCGGTGATAA | ACCGGAGGAA | GGTGGGGATG | ATGTCAAGTC | 1200 |
| ATCATGGCCC | TTACGGGTAG | GGCTACACAC | GTGCTACAAT | GGGCAGTACA | AAGGGTTGCC | 1260 |
| AAGCCGCGAG | GTGGAGCTAA | TCCCAGAAAA | CTGCTCGTAG | TCCGGATTGG | AGTCTGCAAC | 1320 |
| TCGACTCCAT | GAAGTTGGAA | TCGCTAGTAA | TCGCGAATCA | GCATGTCGCG | GTGAATACGT | 1380 |
| TCTCGGGCCT | TGTACACACC | GCCCGTCACA | CCATGGGAGT | GAATTGTACC | AGAAGCGGGT | 1440 |
| AGGCTAACCT | TCGGGAGGCC | GCTCACCACG | GTATGATCCA | NGAC | | 1484 |

NUCLEOTIDE FRAGMENTS CAPABLE OF HYBRIDIZING SPECIFICALLY TO RICKETTSIA RDNA OR RRNA AND THEIR USE AS PROBES OR PRIMERS

The present invention falls within the field of techniques for the detection and/or identification of bacteria of the genus Rickettsia and more particularly of those using a genetic marker.

Rickettsias are Gram-negative bacteria which belong to the order Rickettsiales and to the family Rickettsiaceae comprising especially the subfamily Rickettsieae which is subdivided into three genera: Coxiella, of which the only known species is *Coxiella burnetti*; Rickettsia, including all the other species which are pathogenic to man and animals; and Rochalimea. The genus Rickettsia comprises three subgroups: the typhus group to which *R. typhi*, responsible for endemic typhus, *R. prowazekii*, responsible for epidemic typhus, and *R. canada* belong; the scrub typhus group to which *R. tsutsugamushi* belongs; and the eruptive fever group to which *R. rickettsii, R. siberica, R. conorii, R. australis, R. akari, R. montana* and *R. rhipicephali* in particular belong.

Rickettsias are intracellular parasitic bacteria which multiply in the nucleus and the cytoplasm of the host cells for the strains of the eruptive fever group and in the cytoplasm of these cells for the strains of the other groups. The transmission of the bacteria to man occurs through haematophagous insects such as ticks for *R. tsutsugamushi* (rickettsia of the eruptive fever group), lice for *R. prowazekii* or flea for *R. typhi*, during a blood meal followed by dejecta at the site of the bite.

Epidemic typhus due to *R. prowazekii* characterized by high fever, severe headaches and generalized rashes has nowadays become a rare disease. However, the risk still exists of an outbreak of an epidemic as long as the required conditions are brought together, in particular when the population is dense and hygienic conditions are lacking.

Scrub typhus or endemic typhus, caused by *R. typhi*, is widespread worldwide. Rats are the carriers and their presence determines the appearance of the disease in man. The infection is characterized by headaches, myalgia and fever but, most often, the disease is benign.

Some of the infections associated with rickettsias of the eruptive fever group, and especially the Rocky Mountains spotted fever caused by *R. rickettsii*, can have a fatal outcome for the patient or can at the very least be accompanied by severe complications such as myocarditis, phlebitis, syndrome of meningeal irritation, encephalitis, myelitis and coma.

Scrub typhus is an acute febrile disease the causative agent of which is *R. tsutsugamushi*. The disease is characterized by a rise in temperature and severe headaches, which may be associated with a pneumopathy during the first week of the disease. Moreover, the disease may affect the central nervous system, with clinical manifestations such as delirium, stupor and muscle fibrillation. The death rate varies from 1 to 60% depending on the geographical regions. It is particularly high in South-East Asia, Korea, Australia, Japan and India.

At the present time, no detection technique is, at the same time, specific, sensitive and rapid enough to diagnose an infection due to bacteria of the genus Rickettsia in a biological sample. Testing for the infection is carried out essentially either by direct diagnosis, which is very awkward to carry out because it presupposes the inoculation, using biological samples, of embryonated eggs or animals; or by serological diagnosis, which is often difficult because of the lack of specificity of the techniques used or because of the delayed appearance of antibodies in the sera of patients.

The present invention relates to a technique for the diagnosis of infections caused by bacteria of the genus Rickettsia, and more particularly those caused by *R. tsutsugamushi*, using a genetic marker in a process of detection by hybridization of nucleic acids, combining specificity, sensitivity and speed.

More particularly, the ribosomal RNA of the bacteria is used as target. Indeed, this molecule is found in abundance in all the cells of all living organisms. Moreover, it has a specific nucleotide sequence made up of a succession of regions characterized by a variable rate of evolution.

Bacterial ribosomes contain at least three distinct RNA molecules referenced 5S, 16S and 23S rRNA(s). Historically, these names were chosen with reference to their speed of sedimentation which reflects the size of these RNA molecules. However, the real size of these ribosomal constituents varies substantially, for a given type, from one cellular organism to another. However, the terminology 5S, 16S and 23S rRNA is confined to describing the RNA molecules which constitute the ribosomes in all bacteria.

The taxonomic value of the ribosomal 16S and 23S subunits of various bacterial species has been demonstrated in hybridization processes for quantifying levels of homology between these species. Thus, Woese et al., Microbiological Reviews 47: 621–669 (1983) and Grayet et al., Nucleic Acids Research 12: 5837–5852 (1984) show, by comparisons of 16S RNA sequences, that highly conserved regions are intercalated with regions of average and low homology, even in the case of close species.

To date, only six DNA sequences corresponding to the 16S ribosomal RNAs (rDNA) of bacteria belonging to the Rickettsiaceae family are described in the literature: *R. rickettsii, R. prowezekii, R. typhi, Coxiella burnetti, Ehrlichia ristierii* and *Wolbachia persicae*.

Somes zones of the DNA encoding the 16S subunit ribosomal RNA have now been discovered which are conserved for various species belonging to the genus Rickettsia. Moreover, there have now been discovered on the DNA encoding the 16S ribosomal RNA zones which are variable within the genus Rickettsia. These results have made it possible to prepare probes of the type which make it possible to discriminate between the genus Rickettsia and genera which are taxonomically close, as well as probes specific for species belonging to the genus Rickettsia. These results have been verified especially on the following species: *R. tsutsugamushi, R. canada, R. conorii, R. akari, R. mooseri, R. australis, R. rhipicephali, R. montana, R. bellii, R. japonica, R. parkeri, R. helvetica, R. sibirica, R. massiliae, R. slovaca* and *R. africae*.

Before presenting the invention, various terms used in the description and the claims are defined below:

a nucleotide fragment or an oligonucleotide is a chain of nucleotide units assembled together by phosphoric ester bonds, which is characterized by the informational sequence of the natural nucleic acids, capable of hybridizing to a nucleotide fragment under predetermined conditions, it being possible for the chain to contain monomers of differing structures and to be obtained from a natural nucleic acid molecule and/or by genetic recombination and/or by chemical synthesis, a unit is derived from a monomer which may be a natural nucleotide of a nucleic acid whose constituent elements are a sugar, a phosphate group and a nitrogenous base; in DNA, the sugar is 2-deoxyribose; in RNA, the sugar is ribose; depending on whether DNA or RNA is involved, the nitrogenous base is chosen from adenine, guanine, uracil, cytosine, thymine; or alternatively the monomer is a nucleotide modified in at least one of the three constituent components; by way of example, the modification may occur either at the level of the bases, with modified bases such as inosine, 5-methyldeoxycytidine, deoxyuridine, 5-dimethylaminodeoxyuridine, 2,6-diaminopurine, 5-bromodeoxyuridine or any other modified base capable of hybridization, or at the level of the sugar, for example the replacement of at least one deoxyribose with a polyamide (P. E. Nielsen et al., Science, 254, 1497–1500 (1991)), or alternatively at the level of the phosphate group, for example its replacement by esters especially chosen from diphosphates, alkyl and aryl phosphonates and phosphorothioates, "informational sequence" is understood to mean any orderly succession of nucleotide type units, the chemical nature and the order in a reference direction of which constitute information of the same quality as that of the natural nucleic acids, hybridization is understood to mean the process during which, under appropriate conditions, two nucleotide fragments, having sufficiently complementary sequences, are capable of forming a double strand with stable and specific hydrogen bonds. A nucleotide fragment "capable of hybridizing" with a polynucleotide is a fragment which can hybridize with the said polynucleotide under hybridization conditions, which can be determined in each case in a known manner. The hybridization conditions are determined by the stringency, that is to say the harshness of the operating conditions. The higher the stringency, the more specific the hybridization. The stringency is defined especially according to the base composition of a probe/target duplex, as well as by the degree of mismatch between two nucleic acids. The stringency may also depend on the reaction parameters, such as the concentration and the type of ionic species present in the hybridization solution, the nature and the concentration of the denaturing agents and/or the hybridization temperature. The stringency of the conditions under which a hybridization reaction should be carried out will depend mainly on the probes used. All these parameters are well known and the appropriate conditions can be determined by persons skilled in the art. In general, depending on the length of the probes used, the temperature for the hybridization reaction is between about 20 and 65° C., in particular between 35 and 65° C. in a saline solution at a concentration of about 0.8 to 1M, a probe is a nucleotide fragment comprising from 5 to 100 monomers, especially from 6 to 35 monomers, having a hybridization specificity under determined conditions for forming a hybridization complex with a nucleotide fragment having, in the present case, a nucleotide sequence included in a ribosomal RNA, the DNA obtained by reverse transcription of the said ribosomal RNA and the DNA (called here ribosomal DNA or rDNA) of which the said ribosomal RNA is the product of transcription; a probe may be used for diagnostic purposes (especially capture or detection probes) or for therapeutic purposes, a capture probe is immobilized or is capable of being immobilized on a solid support by any appropriate means, that is to say directly or indirectly, for example by covalent bonding or adsorption, a detection probe may be labelled by means of a marker chosen from radioactive isotopes, enzymes (especially a peroxidase, an alkaline phosphatase, or an enzyme capable of hydrolysing a chromogenic, fluorigenic or luminescent substrate), chromophoric chemical compounds, chromogenic, fluorigenic or luminescent compounds, nucleotide base analogues, and ligands such as biotin, a primer is a probe comprising from 5 to 100 nucleotide units and having a hybridization specificity under determined conditions for the initiation of an enzymatic polymerization, for example in an amplification technique such as PCR (Polymerase Chain Reaction), in a sequencing process, in a reverse transcription method, and the like, homology characterizes the degree of similarity between two nucleotide fragments which are compared, the probes and primers according to the invention are those whose sequences are identified below, as well as the analogues of these probes or primers which are those whose sequences exhibit at least 70% homology, and at least 5 consecutive nucleotide units of informational sequence identical therewith. Such sequences are called here "homologous sequences".

The probes according to the invention which are used for diagnostic purposes can be used in any known hybridization technique and especially the techniques for point deposition on filters called "DOT BLOTTING" (MANIATIS et al., Molecular Cloning, Cold Spring Harbor, 1982), the techniques for DNA transfer called "SOUTHERN BLOTTING" (SOUTHERN. E. M., J. Mol. Biol., 98, 503 (1975), the techniques for RNA transfer called "NORTHERN BLOTTING", or the SANDWICH techniques (DUNN A. R., HASSEL J. A., Cell, 12, 23 (1977)); the SANDWICH technique is used in particular, with a specific capture probe and/or a specific detection probe, it being understood that the capture probe and the detection probe should have at least partly different nucleotide sequences.

Another application of the invention is a therapy probe for treating infections caused by bacteria of the genus Rickettsia, the said probe being capable of hybridizing in vivo with the 16S ribosomal RNA of the said bacteria and/or with the genomic DNA to block the translation and/or transcription phenomena and/or replication.

Table 1 represents the rDNA sequences corresponding to the 16S rRNA of various bacteria of the genus Rickettsia, the list of which appears after the experimental part below. The numbering of the nucleotide sequence of the DNA corresponding to the 16S ribosomal RNA of *R. rickettsii*, completely identified by Weisburg et al. (1989, Genbank (M21293)), was used as reference to define the fragments and to align them. The nucleotide sequences corresponding to the sequences shown in Table 1 appear as SEQ ID NOS: 23–53.

The subject of the present invention is especially a single-stranded nucleotide fragment capable of hybridizing with Rickettsia rDNA or rRNA and not with non-Rickettsia rDNA or rRNA.

In particular, the single-stranded nucleotide fragment is not capable of hybridizing specifically to the rDNA or rRNA of *Cowdria ruminantium, Ehrlichia chaffeensis, Anaplasma marginale, Wolbachia pipientis, Ehrlichia risticii, Rochalimea quintana* and *Coxiella burnatti*.

TABLE 1

```
         10        20        30        40        50        60
 1  ------------------------------------------------------------     0
14  ------------------------------------------------------------     0
10  ------------------------------------------------------------     0
11  ------------------------------------------------------------     0
 3  ------------------------------------------------------------     0
18  ------------------------------------------------------------     0
13  ------------------------------------------------------------     0
 7  ------------------------------------------------------------     0
15  ------------------------------------------------------------     0
16  ------------------------------------------------------------     0
 8  ------------------------------------------------------------     0
17  ------------------------------------------------------------     0
 6  ------------------------------------------------------------     0
 9  ------------------------------------------------------------     0
12  ------------------------------------------------------------     0
 4  ------------------------------------------------------------     0
 5  ------------------------------------------------------------     0
31  ------------------------------------------------------------     0
 2  ------------------------------------------------------------     0
21  ------------------------------------------------------------     0
22  ------------------------------------------------------------     0
19  ----------------------------GA--------CAGAA-----------------     7
20  ----------------------------xx--------CA--------------------     2
23  ------------------------------------------------------------     0
26  TTTACGTTTCTTATATTTGTTTTTTTGCATGAGTCCAAGCCATAAGTAATTATGGTTTTG    60
25  ------------------------------------------------------------     0
27  ------------------------------------------------------------     0
28  ------------------------------------------------------------     0
24  CT----------------------------------------------------------     2
30  ------------------------------------------------------------     0
29  ---------------------------------------------x--------------     0
 C 70        80        90       100       110       120
 1  ------------------CCTGGCTCAGAACGAACGCTATCGGTATGCTTAACACATGC    41
14  ------------------xx......................................    39
10  ------------------xxxxxxxx................................    33
11  ------------------........................................    41
 3  ------------------xxxxxxxxxxxxx...........................    28
18  ------------------........................................    41
13  ------------------........................................    41
 7  ------------------........................................    41
15  ------------------xx......................................    39
16  ------------------xxxxxxxxxxx.............................    30
 8  ------------------........................................    41
17  ------------------xxxx....................................    37
 6  ------------------........................................    41
 9  ------------------........................................    41
12  ------------------.................A......................    41
 4  ------------------........................................    41
 5  ------------------........................................    41
31  ---------------------------------.........................    25
 2  ------------------........................................    41
21  ---------AGAGTTTGAT.......................................    51
22  ------------------........................................    41
19  TCAAACTTGAGAGTTTGAT.......................................    67
20  ---AACTTGAGAGTTTGAT.......................................    59
23  ------------------...............GG...C....C..............    39
26  TCAAACTTGAGAGTTTGAT...............GG...C.A................   120
25  ------------------...............GG...C.A..C..............    36
27  ---------AGAGTTTGAT...............GG...C.A................    51
28  ------------------........T.......GG...C.G..C.............    37
24  ---GATTTGAGAGTTTGAT.....................G.....G...........    59
30  ------------------...............GG...C.G................    36
29  ---xATTGAAGAGTTTGATT..........TT........G...C.............    56
 C  ------------------++++**********CCCT*+CGG+A*GC*TAACACATGC 130       140       150       160       170       180
 1  AAGTCGAACGGACTAATT---GGGGCTT----GCTCCAA--TT-AGTTAGTGGCAGACGG    91
14  ........................---.......---........-...........    89
10  ........................---.......---....--..-...........    83
11  ........................---.......---....--..-...........    91
 3  ........................---.......---.G--....-...........    78
18  ........................---.......---.G--....-...........    91
13  ........................---.......---.G--....-...........    91
 7  ..........T--...........---..............T...............    93
15  .............T--........---..........-...-...............    90
16  .........A......TTT.....---............--..-.............    83
```

TABLE 1-continued

```
 8  ................---.........----....T..---..-................  91
17  ................---.........----.........--..-................  87
 6  .....G..........---.........----.........--..-................  91
 9  ...............---..A......----.........--..-................  91
12  ................---.........----.T....G---..-................  91
 4  ......G.........G--....T..----..A...T..--..-................  92
 5  ......G.........G..---T....T.----T.....G---..-..G.......GA....  91
31  ......G.........---.........----.........--..-................  75
 2  ................G--...-.........----.........--..-................  91
21  .....A..........---.........----.........--..-................ 101
22  ..............--TA..........----.........T..--..-................  91
19  ............T...C---TA.A...C-----....TT.G--..-..A.........A... 117
20  ............T......--TA.A.........----....T.G--..-..A.........  109
23  ..........A.T....GCT--.A.T.------.....TAGT--A.T.A.........A...  91
26  .............AGT.ATTTATA..--TTCG...ATG.GTA.CT................ 178
25  ..............A.T.GCTTATAA.C.TTCG.T.AT..ATAATT................  96
27  .......... ...CGTA-TAC.CA.......-----....G.GT-G.ATG............ 105
28  ..........G.T..A-TT.TA.........-----....ATGG-TA.A.C............  91
24  .............A------TCA.......----GCT.G..GCC..GGTCCC.......... 109
30  .........G..C...------------...TTAG-------------...G..C....A...  73
29  ............--C.GCGCAG..A.xC.T---x....TGGCGGCG-AG......G..... 108
 C  AAGTC*CG*****+  .+*+**    *++*:   ***G*GGC**ACGG 190       200       210       220       230       240
 1  GTGAGTAACACGTGGGAATCTACCCATCAGTACGGAATAACTTTTAGAAATAAAAGCTAA  151
14  ............................................................  149
10  ............................................................  143
11  ............................................................  151
 3  .....................................T......................  138
18  .....................................T......................  151
13  .....................................T......................  151
 7  .....................................T......................  153
15  .....................................T......................  150
16  .....................................T......................  143
 8  ............................................................  151
17  ............................................................  147
 6  ............................................................  151
 9  ..........G.................................................  151
12  ...................................T........................  151
 4  ...............................G............................  152
 5  ...............................G............................  151
31  ...............................G............................  135
 2  ...............................G............................  151
21  ...............................C............................  161
22  ...............................G............................  151
19  ............................................................  177
20  ............................................................  169
23  ...............................G................A.......GT... 151
26  ........TG...A........G.T.GT....T......G..A.........G.T..G... 238
25  ........TG...A..........T.GT....T......G.CA........G.TG.G... 156
27  ........TG.A.A..........T.GT....T..G...G.CAC.......GGTG.G... 165
28  ........TGTA.A...........T.GT.............T.G..G....CG.C.A.... 151
24  ...C.....G........CT.G..TGGT....G........CAG.G....C.TTG.GC.. 169
30  .........G...................TC........ACAG......TTGT....... 133
29  ........TG...A..........TTGT...GG..G.....C.GGG....CTCGG..... 168
 C  ............................................................

250       260       270       280       290       300
 1  TACCGTATATTCTCTG------C--GGAGGAAA-------GATTTATCGCTGATGGATGAG  197
14  .....................-----.--.........-------................  195
10  .....................-----.--.........-------................  189
11  .....................-----.--.........-------...T............  197
 3  .....................-----.--.........-------................  184
18  .....................-----.--.........-------................  197
13  ................-----T--.........-------................  197
 7  .....................-----.--.........-------................  199
15  .....................-----.--.........-------................  196
16  .....................-----.--.........-------................  189
 8  ..............A-----.--.........-------................  197
17  ..............A-----.--.........-------................  193
 6  ..............A-----.--.........-------................  197
 9  ..............A-----.--..............G.-------................  197
12  ....A.........A-----T--.........-------................  197
 4  ..............A-----.--.........-------................  198
 5  ..............A-----.--.........-------................  197
31  ..............A-----.--A.........-------................  181
 2  ..............A-----.--.........-------................  197
21  ..............A-----.--.........-------................  207
22  ..............A-----.--A.........-------...G............  197
```

TABLE 1-continued

```
19  ............A-----.--.........------....................G.  223
20  ............A-----.--.........------....................G.  215
23  ......GCC....A-----TAA........------.......................  199
26  ...T.....A..C...-----.--...G.....------...........AT.A.....  284
25  ...T.....A..C...-----.--...G.....------...........AT.A.....  202
27  ...T.....A..C-..-----.--...G.....------...........AT.A.....  210
28  .......CG.C..A-----.--...G................A.....T...AT.A...  197
24  C..C.....CG.C...-----A--..G................------.T...ATCA...AG.  214
30  ........CGTC.CT------.T-..GA....------..........GA.G........  180
29  .........A.....TTGGAG.AAA.C..GGGATCTTCG..CC.CGT...ATAA......  228
C   *AC**TAT*+*****:      *  *G+*G*         T*G*+GAT**G
```

```
          310       320       330       340       350       360
1   CCCGCGTCAGATTAGGTAGTTGGTGAGGTAATGGCTCACCAAGCCGACGATCTGTAGCTG  257
14  ...........................................................  255
10  ...........................................................  249
11  ...........................................................  257
3   ...........................................................  244
18  ...........................................................  257
13  ...........................................................  257
7   ...........................................................  259
15  .......................................A...................  256
16  ...........................................................  249
8   ...........................................................  257
17  ...........................................................  253
6   ...........................................................  257
9   ...........................................................  257
12  ...............................C...........................  257
4   ...............................C...........................  258
5   ........G......................C......................T....  257
31  ...............................C...........................  241
2   .......................................T...................  257
21  .......................................T...................  267
22  .......................................A...................  257
19  ...........................................................  283
20  ........................T..................................  275
23  ........G...........A...........T........TGT................  259
26  ..TA...T.........C.........A...........T......G.A.T.....A...  344
25  ..TA...T.........C.........A...........T......G.T.T.....A...  262
27  ..TAT..............C...........G......CT...G..GT............  270
28  ..TATA.T.........C.........G........A..CT......GTA.T.....A...  257
24  .......T.........C.........G..........CT......G.........A...  274
30  .......TG.........C.........G.....................G........CA......  240
29  ..TA....G......C.T..........G...........CT..............C....  288
C   CC*******GATTAG+T*GTTGGTGGTAAGC*+ACCAAG+*+GATCTAG*TG
```

```
          370       380       390       400       410       420
1   GTCTGAGAGGATGATCAGCCACACTGGGACTGAGACACGGCCCAGACTCCTACGGGA-GG  316
14  ..........................................................-..  314
10  ..........................................................-..  308
11  ..........................................................-..  316
3   ..........................................................-..  303
18  ..........................................................-..  316
13  ..........................................................-..  316
7   ..........................................................-..  318
15  ..........................................................-..  315
16  ..........................................................-..  308
8   ..........................................................-..  316
17  ..........................................................-..  312
6   ..........................................................-..  316
9   ..........................................................-..  316
12  ..........................................................-..  316
4   ..........................................................-..  317
5   ..........................................................-..  316
31  ..........................................................-..  300
2   ..........................................................-..  316
21  ..........................................................-..  326
22  ..........................................................-..  316
19  ..........................................................-..  342
20  ..........................................................-..  334
23  ............C..A.....................................G-..  318
26  ............C..............A........T....T..............-..  403
25  ............C..............A........T....T..............-..  321
27  ............................A........T.................-..  329
28  A...........................A........T....T..............-..  316
24  ............................A........T..................-..  333
30  ..........................................................-..  299
29  ............C.............................x...............-..  346
C   *TCTGAGAGGA*GA*CAGCCACACTGG*ACTGAGA**CGG*CCAGACTCCTAGGG*  GG
```

TABLE 1-continued

```
       430       440       450       460       470       480
 1 CAGCAGTGGGGAATATTGGACAATGGGCGAAAGCCTGATCCAGCAATACCGAGTGAGTGA  376
14 ..........................................................  374
10 ..........................................................  368
11 ..........................................................  376
 3 ..........................................................  363
18 ..........................................................  376
13 ..........................................................  376
 7 ..........................................................  378
15 ..........................................................  375
16 ..........................................................  368
 8 ..........................................................  376
17 ..........................................................  372
 6 ..........................................................  376
 9 ..........................................................  376
12 ..........................................................  376
 4 ..........................................................  377
 5 ..........................................................  376
31 ..........................................................  360
 2 ..........................................................  376
21 ...............................CGx.........................  385
22 ..........................................................  376
19 ..........................................................  402
20 ..........................................................  394
23 ......................................G...C...............  378
26 ....................................T..G...C..............  463
25 ....................................T..G...C..............  381
27 ....................C...............T..G...C..............  389
28 ....................................C.G...CA..............  376
24 ........A...........................C......CA..............  393
30 ........G.C..C......................C..G...C..............  359
29 ...........................G....C...............G...C...T....  406
 C CAGCAGTG*GAATATTGGAVAATGG*G*AA***TVFATCCAGC*AT+CCG+*TG*GTGA 490       500       510       520       530       540
 1 TGAAGGCCTTAGGGTTGTAAAGCTCTTTTAGCAAGGAAGA------------TAAT----  420
14 ........................................------------....----  418
10 ........................................------------....----  412
11 ........................................------------....----  420
 3 ........................................------------....----  407
18 ........................................------------....----  420
13 ........................................------------....----  420
 7 ........................................------------....----  422
15 ........................................------------....----  419
16 ........................................------------....----  412
 8 ........................................------------....----  420
17 ........................................------------....----  416
 6 ........................................------------....----  420
 9 ...............................G.......------------....----  420
12 ........................................------------....----  420
 4 ........C...............................------------....----  421
 5 ........C...............................------------....----  420
31 ........C...............................------------....----  404
 2 ........C...............................------------....----  420
21 ........................................------------....----  429
22 ........................................------------....----  420
19 ........................................------------....----  446
20 ........................................------------....----  438
23 ........................T.G...T.........------------....----  422
26 A.........C.........A......AT.G..........------------....----  507
25 A.........C.........A......C.AT.G........------------....----  425
27 G.........C.........A......C..T.G........------------....----  433
28 A........T.................TG............------------....----  420
24 ........C.T................TGG............------------....----  437
30 ........C..................C.C.GGT........------------....----  403
29 A.........C............A....CG.TGG......AATTCTCAAGGG....ATCC  466
 C *GAAGGCC*T*GGGTTGTAAA*C*CTTT***+*+*GA*GA              TAAT 550       560       570       580       590       600
 1 ---------GACGTTACTTGCAGAAAAAGCCCCGGCTAACTCCGTGCCAGCAGCCGCGGT  471
14 ---------.................................................  469
10 ---------.................................................  463
11 ---------.................................................  471
 3 ---------.................................................  458
18 ---------.................................................  471
13 ---------.................................................  471
 7 ---------.................................................  473
15 ---------.................................................  470
```

TABLE 1-continued

```
16  --------........................................  463
 8  --------........................................  471
17  --------........................................  467
 6  --------........................................  471
 9  --------........................................  471
12  --------........................................  471
 4  --------........................................  472
 5  --------........................................  471
31  --------........................................  455
 2  --------........................................  471
21  --------.............T....x.....................  479
22  --------........................................  471
19  --------........................................  497
20  --------........................................  489
23  --------...AG...C.A.............................  473
26  ---------..G...C.AT........T......A.............  558
25  ---------..G...C.AT....G...T......A.....T.......  476
27  ---------..G...C.A.....G...T......A.............  484
28  ---------..G....CA.....G...T..T.................  471
24  ---------..G...CCA.....G...T....................  488
30  ---------.....ACC.G....G.................T......  454
29  TxGGGCGTT........CCA.....G....A.T.........T.....  525
 C            GAC**TA*+*+*AGAA*AAG**C*G*C*AACT**GTGCCAGCAGCCGCGGT 610       620       630       640       650       660
 1  AAGACGGAGGGGGCTAGCGTTGTTCGGAATTACTGGGCGTAAAGAGTGCG-TAGGCGGTT  530
14  ..........................................-..........         528
10  ..........................................-..........         522
11  ..........................................-..........         530
 3  ..........................................-..........         517
18  ..........................................-..........         530
13  ..........................................-..........         530
 7  ..........................................-..........         532
15  ..........................................-..........         529
16  ..........................................-..........         522
 8  ..........................................-..........         530
17  ..........................................-..........         526
 6  ..........................................-..........         530
 9  ..........................................-..........         530
12  ..........................................-..........         530
 4  ..........................................-..........         531
 5  ..........................................-..........         530
31  ..........................................-..........         514
 2  ..........................................-..........         530
21  ..........................................-..........         538
22  ..........................................-..........         530
19  ..........................................-..........         556
20  ..........................................-....T....         548
23  ...................................G.C...-..........         532
26  ..T..........A.............T.........G.CA..-....T..AC         617
25  ..T..........A.............T.........G.CA..-....T..AC         535
27  ..T..........A.............T.........G.CAT.-..........        543
28  ..T......A...........A.............T.........G.C...-....T.G.  530
24  ..T...................................G.....-..........C      547
30  ..T...A.................T................C.CAT.-........A.    513
29  ..T..A...A.T..A.......AA........C.........C.C....-....T..A.   584
 C  AA+AC**AG*G*GC*AGCGTT**TCGGA*T*A*TGGGCGTAAAG+G*G TAGGG**

670       680       690       700       710       720
 1  TAGTAAGTTGGAAGTGAAAGCCCGGGGCTT-AACCTCGGAATTGCTTTCAAAACTACTAA  589
14  .............................-..........................G    587
10  .............................-............................   581
11  .............................-............................   589
 3  .............................-............................   576
18  .............................-............................   589
13  .............................-............................   589
 7  .........G...................-............................   591
15  .............................-............................   588
16  .............................-............................   581
 8  .............................-............................   589
17  .............................-............................   585
 6  .............................-............................   589
 9  .............................-............................   589
12  .............................-......A.....................   589
 4  .............................-............................   590
 5  .............................-............................   589
31  .............................-............................   573
 2  .............................-............................   589
21  .............................-............................   597
```

TABLE 1-continued

```
22  .............................-............................ 589
19  .............................-............................ 615
20  .............................-............................ 607
23  ..A......A.G.......T...A......-....CT....C.....CT......GT..G 591
26  .........AA.........TA..AAA...C-...T.T...GC......T..T...G...G 676
25  .........AA.........TA..AA......-...T.T...GCG.....T..T...G...G 594
27  .G.......AA.G.......TA.A......-....CT...GGC......T..T...G.AGG 602
28  ..A......AA.........T...A......-....T.........T.......T... 589
24  CC.......A.GT.......T..TT.......-...CAA...C...A..T......GTGGG 606
30  ATT.....CA..G.......T...A......-C....CT....C...C..TG.T...GGATG 572
29  ATT.....C...T........T......-xxx...G.........ACC.G.T...GGGT. 640
C   ***TAAGT*+***GTGAAA+*C*+**GCT* C+*G**GC*+*A*ACT+***+

730       740       750       760       770       780
 1  TCTAGAGTGTAGTAGGGGATGATGGAATTCCTAGTGTAGAGGTGAAATTCTTAGATATTA 649
14  ............................................................ 647
10  ............................................................ 641
11  ............................................................ 649
 3  ............................................................ 636
18  ............................................................ 649
13  ............................................................ 649
 7  ............................................................ 651
15  ............................................................ 648
16  ............................................................ 641
 8  ............................................................ 649
17  ............................................................ 645
 6  ........A................................................... 649
 9  ............................................................ 649
12  ............................................................ 649
 4  ............................................................ 650
 5  ............................................................ 649
31  ............................................................ 633
 2  ............................................................ 649
21  ............................................................ 657
22  ............................................................ 649
19  ............................................................ 675
20  ............................................................ 667
23  G......A.G....A..G........T.............A................... 651
26  A......GTCGAG..A....AGC..................G.................. 736
25  A......GTCGAA..A....AGC..................G.................. 654
27  A......CCG.A..A....AGC..................G.................. 662
28  .......AT.GAA..A....AGA.........GA........A......G..A...... 649
24  A..C..AC..GAG..A..GCA........TT.G......G.........C.G.......C. 666
30  ...C......G.A..A...TGAG......G.........A......G.........C 632
29  ...T......A.G....A..GAAx.......T.CG......C.......G.G........CG 699
C   *CT*GA**+*+AG+GG+GGAATT***TGTAG*GGT*AAAT*C+TA*ATAT**+

790       800       810       820       830       840
 1  GGAGGAACACCGGTGGCG--AAGGCGGTCATCTGGGCTACCACTGACGCTGATGCACGAA 707
14  ..........A.......--......................A................ 705
10  ..................--......................A................ 699
11  ................A.--......................A................ 707
 3  ..................--......................A................ 694
18  ..................--......................A................ 707
13  ..................--......................A................ 707
 7  ..................--......................A................ 709
15  ..................--....G.................A................ 706
16  ..................--......................A................ 699
 8  ..................--......................A................ 707
17  ..................--......................A................ 703
 6  ..................--......................A................ 707
 9  ..................--...................G.A................ 707
12  ................A.--......................A................ 707
 4  ..................--......................A................ 708
 5  ..................--....G.................................. 707
31  ..................--......................A................ 691
 2  ..................--......................A................ 707
21  ..................--............x....A.....x................ 713
22  ..................--......A.......A.....TA................ 707
19  ..................--......................A................ 733
20  ..................--......................A.........x.... 724
23  .A........A......---..A..T..........C.TT..........G..G.... 709
26  ...........CT......--......CTCGAT......A....G.TG.... 794
25  ...........A......CT......TTCGAT......A....G.TG.... 712
27  ...........A......--......CTG.....T.CGGT.....G.TG.... 720
28  ..........A......--......TCT......TTC.AAT..........A..G.... 707
24  A........GT.A.G....--.. ...A.TGC....ATC..AGT..........G.... 724
30  ...........A......---.  ..CTCA....T.C.TT......G.TG.... 690
29  .A.A........A......--G. ....ACTTC....A.C.AT......A....G..G.... 757
```

TABLE 1-continued

```
 C  **A*GAAC**C+G*GGC*   AA*GC*+CT*G+*+*++**TGAC*CT*A+G*+CGAA 850       860       870       880       890       900
  1  AGCGTGGGGAGCAAACAGGATTAGATACCCTGGTAGTCCACGCCGTAAACGATGAGTGCT   767
 14  ............................................................   765
 10  ............................................................   759
 11  ............................................................   767
  3  ............................................................   754
 18  ............................................................   767
 13  ............................................................   767
  7  ............................................................   769
 15  ............................................................   766
 16  ............................................................   759
  8  ............................................................   767
 17  ............................................................   763
  6  ............................................................   767
  9  ............................................................   767
 12  ............................................................   767
  4  ............................................................   768
  5  ............................................................   767
 31  ............................................................   751
  2  ............................................................   767
 21  ............................................................   773
 22  ............................................................   767
 19  ............................................................   793
 20  ............................................................   784
 23  ...........................................T................   784
 26  ...........................................T................   854
 25  ........................T..................T................   772
 27  ...........................................T................   780
 28  G..........................................T..........A..T..   767
 24  ...........................................T................   784
 30  ...........................................T..........A..T..   750
 29  .....................G....................x..C.........AA..   816
  C  *GCGTGGGGAGCAAACAGGATTAGA*ACCCT*GTAGTCCACGC+GT*AACGATGA****T 910       920       930       940       950       960
  1  -AGATATCGGAA----GATTCT-CTTTCGGTTTCGCAGCTAACGCATTAAGCACTCCGCC   821
 14  -...........----......-......................................   819
 10  -...........----......-.........T............................   813
 11  -...........----......-......................................   821
  3  -...........----......-......................................   808
 18  -...........----...G..-......................................   821
 13  -...........----......T......................................   821
  7  -...........----......-......................................   823
 15  -...........----......-......................................   820
 16  -...........----......-......................................   813
  8  -...........----......-......................................   821
 17  -...........----......-......................................   817
  6  -...........----......-......................................   821
  9  -...........----......-......................................   821
 12  -...........----......-......................................   821
  4  -...........----.....T.-......................................   822
  5  -...........----..G...-......................................   821
 31  -...........----......-......................................   805
  2  -.......T..G.----......T.-...C..................................   821
 21  -...........----......A...-..C.............CG...................   826
 22  -.........G.----......A.A.-..C..................................   821
 19  -.........G.----......G---......................................   847
 20  -.........G.----......G---......................................   838
 23  -.......T..GG----......T.T.....A......T.........................   824
 26  -.A..G.-.AGG----A--.T.TA.C.TT..A.T.T.........G................   906
 25  -.A..G.-.AGG----A--.T.TA.C.TT..A.T.T.........G................   824
 27  -GA..G.-..GG----.C..T.-GCC..T..G.T.T.........G................   833
 28  -.A....G..G.-----.T.A.....T..A.TA............G...A..T.......   820
 24  -.A.AG.-.-GG----TTA.T.TA.C.---.C..T.T............G.....A......   835
 30  -..CCG....GT----.G..TACTAC.....GG....CG.......G....A..T.....   805
 29  -...C.G.T..----GAAG...CCT.C.TA..AG..A..........G.....TT.......   871
  C  *****T+G*++       *++T+*  **+T*+G***+ATAACGC+TTAA****TCCGCC 970       980       990      1000      1010      1020
  1  TGGGGAGTACGGTCGCAAGATTAAAACTCAAAGGAATTGACGGGGGCTCGCACAAGCGGT   881
 14  ............................................................   879
 10  ............................................................   873
 11  ............................................................   881
  3  ............................................................   868
 18  ............................................................   881
 13  ............................................................   881
  7  ............................................................   883
```

TABLE 1-continued

```
15      ............................................................  880
16      ............................................................  873
 8      ............................................................  881
17      ............................................................  877
 6      ............................................................  881
 9      ............................................................  881
12      ............................................................  881
 4      ............................................................  882
 5      ............................................................  881
31      ............................................................  865
 2      ............................................................  881
21      ............................................................  886
22      ............................................................  881
19      ............................................................  907
20      ............................................................  898
23      ...................................................C........  884
26      ......C.............C..............................A.C......  966
25      ......C.............C..............................A.C.....-.  883
27      ......C.............C..............................A.x......  892
28      ......C.............C..............................A.C......  880
24      ......C.............C..............................A........  895
30      ...................................................C.......-.  864
29      ...........C......G..........A.....................x........  930
 C TGGGGA*TACGG*CGCAAG**TAAAACTCAAAG*AATTGACGGGG*C+CGCACAAGCG*T 1030      1040      1050      1060      1070      1080
 1 GGAGCATGCGGTTTAATTCGATGTTACGCGAAAAACCTTACCAACCCTTGACATGGTGGT  941
14 ............................................................  939
10 ............................................................  933
11 ............................................................  941
 3 ............................................................  928
18 ............................................................  941
13 ............................................................  941
 7 ............................................................  943
15 ............................................................  940
16 ............................................................  933
 8 ............................................................  941
17 ............................................................  937
 6 ............................................................  941
 9 ............................................................  941
12 ............................................................  941
 4 ............................G...............................  942
 5 ..........................................T.................  941
31 ............................................................  925
 2 ............................................................  941
21 ............................................................  946
22 ............................................................  941
19 ............................................................  967
20 ............................................................  958
23 ...............A.C...................T...............A..      944
26 ........T..........CA.....................CTTT........AA...    1026
25 ........T..........CA.....................CTTT........AA...    943
27 ........T..........CA.....................CTT.........A..C    952
28 ........T..........CA.....................CTT.........AAAA.   940
24 ....T...T..........CA.....................TA..........TG.A.   955
30 ........T..........A.CA.....C.G..........G...........CCC.A.   924
29 ........T..........CA...............T..................CC.C.-  989
 C GGAG*ATG+GGTTTAATTCGA*G++*CGCG*A*AACCTTACC*****TTGACAT******

1090      1100      1110      1120      1130      1140
 1 TGCGGATCGCAGAGATGCTTTTCTTCAGCTCGGCTGGACCACAC-ACAGGTGTTGCATGG  1000
14 C...........................................-...............  998
10 C...........................................-...............  992
11 C.....................................T....-...............  1000
 3 C...........................................-...............  987
18 C...........................................-...............  1000
13 C...........................................-...............  1000
 7 C...........................................-...............  1002
15 C...........................................-...............  999
16 C.T.........................................-...............  992
 8 C...........................................-...............  1000
17 C...........................................-...............  996
 6 C...........................................-...............  1000
 9 C.T.A.......................................-...............  1000
12 C...............................C...........-...............  1000
 4 ................................C...........-...............  1001
 5 ................................C......T....-...............  1000
31 C...............................C...........-...............  984
 2 C...............................C......T....-...............  1000
```

TABLE 1-continued

```
21 C....................C......T.............-................ 1005
22 C......T.............C......T.............-................ 1000
19 .A.....T.............C......T................-............. 1026
20 .AT....T.............C......T.........G......-............. 1017
23 C...A.AAATG....CAT..........T.T.........T....-.............. 1003
26 C.TATCC.TTTT.-.CCGAGGGAG....T...........TT..-.......C....... 1084
25 C.TATCC.T.CT.-..AGGGGGAG....T...........TT..-.......C....... 1001
27 .AGATCCTT.TT.-.CAGAAGGGCG...T........G...T.G.-.......C....... 1010
28 CATACC.ATTC..-.G.GA.AGGG...G.T.....C...TTTT..-...A........... 998
24 ..TATCC.T.T..-.G.GAGGGAG....T.........T.CA..-................ 1013
30 C.....AG.TG....CA.CC.C......T.A.......T.GGTG-................ 983
29 -.AACT.GT........A...GG.G.C-T....--.A...GAGTG.......C....... 1045
 C +*+*+**++*+*A*A+*:*C:T*GGG+* ACA*GTG*TGCATGG 1150       1160       1170       1180       1190       1200
 1 CTGTCGTCAGCTCGTGTCGTGAGATGTTGGGTTAAGTCCCGCAACGAGCGCAACCCTCAT 1060
14 ............................................................ 1058
10 ............................................................ 1052
11 ............................................................ 1060
 3 ............................................................ 1047
18 ............................................................ 1060
13 ............................................................ 1060
 7 ............................................................ 1062
15 ............................................................ 1059
16 ............................................................ 1052
 8 ............................................................ 1060
17 ............................................................ 1056
 6 ............................................................ 1060
 9 ............................................................ 1060
12 ............................................................ 1060
 4 ............................................................ 1061
 5 ............................................................ 1060
31 ............................................................ 1044
 2 ............................................................ 1060
21 ............................................................ 1065
22 ............................................................ 1060
19 ..........................................................T.. 1086
20 ..........................................................T.. 1077
23 ..........................................................T.. 1063
26 ............................................................ 1144
25 ............................................................ 1061
27 ............................................................ 1070
28 ............................................................ 1058
24 ............................................................ 1073
30 ........................................................GC 1043
29 ....................................T..................G. 1105
 C CTGTCGTCAGCTCGTGTCGTGAGATGTTGGGTTAAGTCCCG*AACGAGCGCAACCCT***

1210       1220       1230       1240       1250       1260
 1 TCTTATTTGCCAGCGGGTAATGCCGGGAACTATAAGAAAACTGCCGGTGATAAGCCG-GA 1119
14 .........................................................-.. 1117
10 .........................................................-.. 1111
11 .........................................................-.. 1119
 3 .........................................................-.. 1106
18 .........................................................-.. 1119
13 .........................................................-.. 1119
 7 .........................................................-.. 1121
15 .........................................................-.. 1118
16 .........................................................-.. 1111
 8 .........................................................-.. 1119
17 .........................................................-.. 1115
 6 .........................................................-.. 1119
 9 .........................................................-.. 1119
12 ......................A..................................-.. 1119
 4 .........................................................-.. 1120
 5 .........................................................-.. 1119
31 .........................................................-.. 1103
 2 .........................................................-.. 1119
21 ......................A..................................-A- 1123
22 ......................A......................A........T.-.. 1119
19 ...............T.........................................-.. 1145
20 .........................................................-.. 1136
23 ........................G.................C.............-.. 1122
26 C....G..A...A.A........T...C...C........G.........A........A.T.-.. 1203
25 C....G..A...A.A............T...C...C........G........A.T.-.. 1120
27 C....G..A...........................C...T...G........A.T.-.. 1129
28 C....G.......T.A........T.A.T...T....G........A........T.-.. 1117
24 C....G........T.CG-........T...........G........A....C...T.-.. 1131
30 C....G......T.ATTA.G.--T...C...C..G.GGG................A... 1101
```

TABLE 1-continued

```
29 C....G.........A..C.A.T........C....G.G..............A...-..  1164
 C +CTTA+TT*CCA*************G*ACT+TA*G+**ACTGCC*GTG**AA*C*G **

1270      1280      1290      1300      1310      1320
 1 GGAAGGTGGGGACGACGTCAAGTCATCATGGCCCTTACGGGTTGGGCTACACGCGTGCTA   1179
14 ............................................................   1177
10 ............................................................   1171
11 ............................................................   1179
 3 ............................................................   1166
18 ............................................................   1179
13 ............................................................   1179
 7 ............................................................   1181
15 ............................................................   1178
16 ............................................................   1171
 8 ...............T............................................   1179
17 ...............T............................................   1175
 6 ............................................................   1179
 9 ............................................................   1179
12 ............................................................   1179
 4 ............................................................   1180
 5 ..............................................T.............   1179
31 ............................................................   1163
 2 ............................................................   1179
21 -.....................................................G.....   1182
22 ............................................................   1179
19 ............................................................   1205
20 ............................................................   1196
23 ............T..G..................T..A......................   1182
26 ............T..T........G..C........TA..G..........A........   1263
25 ............T..T........G..C........TAA.G..........A........   1180
27 ............T..T........G..C........T...G..........A........   1189
28 ............T..T....................T...T..AG......A........   1177
24 .....................................T..TA.........A...A....  1191
30 ............T.........C.................C..........A........  1161
29 ............T..T..GTCAAGTC**CA*GGCC*TTA+*****GGGCT*CAC+CGT*CTA  1224
 C *GAAGGTGGGGA+GA*GTCAAGTC**CA*GGCC*TTA+*****GGGCT*CAC+CGT*CTA 1330      1340      1350      1360      1370      1380
 1 CAATGGTGTTTACAG-AGGGAAGCAAGACG-GCGACGTGGAGCAAATCCC-TAAAAGACA   1236
14 ...............-.............-...................-.........   1234
10 ...............-.............-...................-.........   1228
11 ...............-.............-...................-.........   1236
 3 ...............-.............-...................-.........   1223
18 ...............-.............-...................-.........   1236
13 ...............-.............-...................-.........   1236
 7 ...............-.............-...................-.........   1238
15 ...............-.............-...................-.........   1235
16 ...............-.............-...................-.........   1228
 8 ...............-.............-...................-.........   1236
17 ...............-.............-...................-.........   1232
 6 ...............-.............-...................-.........   1236
 9 ...............-.............-...................-.........   1236
12 ...............-.............-...................-.........   1236
 4 ...............-.............-...................-.........   1237
 5 ...............-........TA...-...................-.........   1236
31 ...............-.............-...................-.........   1220
 2 ...............-.............-...................-.........   1236
21 ...............-.............-...................-.........   1239
22 ................A...-.............................-.........   1236
19 ...............-......T....-.T....................-.........   1262
20 ...............-............-.T...................-.........   1253
23 .......ACC.....-..T..T..G.T....-.T.............T....AT-......GT.  1239
26 ......CAAC....AT...TT-..G....C-.....G..TT...T.....-.AA.....TTG  1320
25 ......CAAC....AT...TC-..G....C--..A.G..TT...T.....-.A......TTG  1237
27 ......C.AC....AT...TT-....CGTC-..A.G.CT....T.....-.G......T.G  1246
28 .......C....AT-...CT.....GT.C..A.GCCTA....T...............  1235
30 ........G.G....T-...C...G.....C-....G..C....T....T.-C......C..  1218
29 ......GCAG....A-.....TT..C.-.GCC.....G........T......AG....CTGC  1282
 C CAATGG**++*ACA* ****+*GC*A**** G**A+*****GC+AATC** *AAA**+**

1390      1400      1410      1420      1430      1440
 1 TCTCAGTTCGGATTGTTCTCTGCAACTCGAGAGCATGAAGTT-GGAATCGCTAGTAATCG  1295
14 ..........................................-...............  1293
10 ..........................................-...............  1287
11 ..........................................-...............  1295
 3 ..........................................-...............  1282
18 ..........................................-...............  1295
```

TABLE 1-continued

```
13  ..........................................-..............  1295
 7  ..........................................-..............  1297
15  ..........................................-..............  1294
16  ..........................................-..............  1287
 8  ..........................................-..............  1295
17  ..........................................-..............  1291
 6  ..........................................-..............  1295
 9  ..........................................-..............  1295
12  ..........................................-..............  1295
 4  ..........................................-..............  1296
 5  ..........................................-..............  1295
31  ..........................................-..............  1279
 2  ..........................................-..............  1295
21  ..............C...........................-..............  1298
22  ..........................................-..............  1295
19  ..........................................-..............  1321
20  ..........................................-..............  1312
23  ..............CA...........T.........C-..................  1298
26  .....................................C-..................  1379
25  .....................................C-..................  1296
27  ..............C....T........G........C-..................  1305
28  ..............A.............TA........-..................  1294
24  ........A......CCT...........AG........-..................  1309
30  ..............CA............T.........-..................  1277
29  ..GT...C.......GAG...........CTC.......-T.................  1341
 C  TC**AGT*CGGATTG***TCTG*AACTCGA***CATGAAGT* GGAATCGCTAGTAATCG 1450      1460      1470      1480      1490      1500
 1  CGGATCAGCATGCCGCGGTGAATACGTTCTCGGGCCTTGTACACACTGCCCGTCACGCCA  1355
14  ............................................................  1353
10  ............................................................  1347
11  ............................................................  1355
 3  ............................................................  1342
18  ............................................................  1355
13  ............................................................  1355
 7  ............................................................  1357
15  ............................................................  1354
16  ............................................................  1347
 8  ............................................................  1355
17  ............................................................  1351
 6  ............................................................  1355
 9  ............................................................  1355
12  ............................................................  1355
 4  ............................................................  1356
 5  ............................................................  1355
31  ............................................................  1339
 2  ............................................................  1355
21  ............................................................  1358
22  ............................................................  1355
19  ............................................................  1381
20  ............................................................  1372
23  ........................................................G.A...  1358
26  T.....T......A....................T......................  1439
25  T.....T......A....................T......................  1356
27  T............A....................T......................  1365
28  T............A....------------------------  1325
24  .A...........T....................T.................G....  1369
30  T............A..........C...............C..........A....  1337
29  ..A..........T..........................C..........A....  1401
 C  ***ATCA*CATG***CGGTGAATACGTTC*C****************************

1510      1520      1530      1540      1550      1560
 1  TGGGAGTTAGTTTTACCTGAAGGTGGTGAGCTAAC-G-CAAG-AGGCAGCCAACCACGGT  1412
14  ...............................-.-....-.................  1410
10  ...............................-.-....-.................  1404
11  ........G......................-.-....-.................  1412
 3  ...............................-.-....-.................  1399
18  ...............................-.-....-.................  1412
13  ...............................-.-....-.................  1412
 7  ...............................-.-....-.................  1414
15  ...............................-.-....-.................  1411
16  ...............................-.-....-.................  1404
 8  ........G......................-.-....-.................  1412
17  ........G......................-.-....-.................  1408
 6  ........G.............A........-.-....-.................  1412
 9  ........G......................-.-....-.................  1412
12  ........G......................-.-....-.................  1412
 4  ........G......................-.-....-.................  1413
 5  ........G......................-.-....-.................  1412
```

TABLE 1-continued

```
31      .......G...................-.-....-.................. 1396
 2      .......G...................-.-....-.................. 1412
21      .......G...........G......C.-....-.................. 1416
22      .......G...................-.-....-.................. 1412
19      .......G...................-.-....-.................. 1438
20      .......G..........T........-.-....-.................. 1429
23      .....C...GG........T.......-.-T...-..........T....... 1415
26      .....A..G.C..A..TC....C......T......C.-T...G.A.......TTT.A... 1498
25      .....A..G.C..A..TC....C......T......C.-....G.A.......TTT.A... 1415
27      .....A..G.C..A..TC....C.....C..C...C.-T...G..........TTT.A... 1424
28      ------------------------------------------------------ 1325
24      .....CA.C....TC....C.A........G..C.-....G.......T.T.T..... 1428
30      .......G......C.......C..T......C.-....G.......G........ 1396
29      .......G.A..G....A....CG...AG......CTT.GG.AG.C.-..TC........ 1460
 C      *******:********+****+*****+******.* **** ****************

1570      1580      1590      1600      1610      1620
 1      AAAATTAGCGACTGGGGTGAAGTCGTAA-------------------------------- 1440
14      ...........................-------------------------------- 1438
10      ...........................-------------------------------- 1432
11      ...........................-------------------------------- 1440
 3      ...........................-------------------------------- 1427
18      ...........................-------------------------------- 1440
13      ...........................-------------------------------- 1440
 7      ...........................-------------------------------- 1442
15      ...........................-------------------------------- 1439
16      ...........................-------------------------------- 1432
 8      ...........................-------------------------------- 1440
17      ...........................-------------------------------- 1436
 6      ...........................-------------------------------- 1440
 9      ...........................-------------------------------- 1440
12      ...........................-------------------------------- 1440
 4      ...........................-------------------------------- 1441
 5      .G.........................-------------------------------- 1440
31      ...........................-------------------------------- 1408
 2      ...........................-------------------------------- 1440
21      ...........................-------------------------------- 1435
22      ...........................-------------------------------- 1440
19      ...........................CAAGGTAGCCGTAGGGGAACCTGCGGCTGGAT 1498
20      ...........................-------------------------------- 1441
23      .G..C.G.T..........A.........CAAGG-------------------------- 1448
26      TGGG....T....A...............CAAGGTAGCTGTAGGTGAACCTGCGGCTGGAT 1558
25      TGGG....T....A...............-------------------------------- 1434
27      TGGG.CG.T....................CAAGGTAGCTGTAGGTGAACCTGCGGCTGGAT 1484
28      ------------------------------------------------------------ 1325
24      GGGG.GG.T.........T..........CAAGGTAGCCGTAGGTGAACCTGCGGCTGGAT 1488
30      .GGG.C.......................-------------------------------- 1415
29      .TG..CCAx...-------------------------------------------------- 1471
 C      ++++++++++++++++++++++++++++

1630
 1      ----------                                                    1440
14      ----------                                                    1438
10      ----------                                                    1432
11      ----------                                                    1440
 3      ----------                                                    1427
18      ----------                                                    1440
13      ----------                                                    1440
 7      ----------                                                    1442
15      ----------                                                    1439
16      ----------                                                    1432
 8      ----------                                                    1440
17      ----------                                                    1436
 6      ----------                                                    1440
 9      ----------                                                    1440
12      ----------                                                    1440
 4      ----------                                                    1441
 5      ----------                                                    1440
31      ----------                                                    1408
 2      ----------                                                    1440
21      ----------                                                    1435
22      ----------                                                    1440
19      TACCTCCTTA-                                                   1508
20      ----------                                                    1441
23      ----------                                                    1448
26      TACCTCCTTTT                                                   1569
25      ----------                                                    1434
27      CACCTCCTT--                                                   1493
28      ----------                                                    1325
```

TABLE 1-continued

| 24 | TACCTCCTTT- | 1498 |
| 30 | ----------- | 1415 |
| 29 | ----------- | 1471 |

The single-stranded nucleotide fragment of the invention has a nucleotide sequence of at least 5 consecutive nucleotides chosen from the following sequences:

starting at nucleotide No. 130 and ending at nucleotide No. 170 starting at nucleotide No. 181 and ending at nucleotide No. 201 starting at nucleotide No. 241 and ending at nucleotide No. 272 starting at nucleotide No. 284 and ending at nucleotide No. 298 starting at nucleotide No. 299 and ending at nucleotide No. 315 starting at nucleotide No. 334 and ending at nucleotide No. 357 starting at nucleotide No. 460 and ending at nucleotide No. 481 starting at nucleotide No. 504 and ending at nucleotide No. 536 starting at nucleotide No. 550 and ending at nucleotide No. 570 starting at nucleotide No. 561 and ending at nucleotide No. 585 starting at nucleotide No. 661 and ending at nucleotide No. 684 starting at nucleotide No. 710 and ending at nucleotide No. 739 starting at nucleotide No. 903 and ending at nucleotide No. 929 starting at nucleotide No. 940 and ending at nucleotide No. 960 starting at nucleotide No. 1035 and ending at nucleotide No. 1055 starting at nucleotide No. 1078 and ending at nucleotide No. 1107 starting at nucleotide No. 1199 and ending at nucleotide No. 1213 starting at nucleotide No. 1330 and ending at nucleotide No. 1350 starting at nucleotide No. 1361 and ending at nucleotide No. 1387 starting at nucleotide No. 1429 and ending at nucleotide No. 1463 starting at nucleotide No. 1501 and ending at nucleotide No. 1520 starting at nucleotide No. 1555 and ending at nucleotide No. 1576 and their complementary sequences.

The invention relates especially to the single-stranded nucleotide fragments having a sequence of at least 8, and in particular of at least 10, consecutive nucleotides which is chosen from the abovementioned sequences (or from complementary sequences). Of course, the invention extends to any nucleotide fragment which is sufficiently homologous to a fragment as defined above to be capable of hybridizing specifically with Rickettsia rDNA or rRNA.

More particularly, the nucleotide sequences of the fragments of the invention are chosen from the sequences SEQ ID NO 1 to SEQ ID NO 22, which are described at the end of the description, or their complementary sequences.

The numbering of the sequence of the 16S rRNA of *R. rickettsii*, applied to the sequences SEQ ID NO 1 to SEQ ID NO 22 above, does not always reflect the number of nucleotides or monomers constituting these sequences because of the size variations existing between the sequences and the sequence of the 16S rRNA of *R. rickettsii*. The variations are due to natural insertions or deletions in the genetic material.

In accordance with the above definition, the fragments of the invention are DNA fragments, but they may also be single-stranded RNA fragments, or their complementary fragments, as well as single-stranded genomic DNA fragments whose transcription products are the abovementioned RNA fragments, or their complementary fragments.

The single-stranded nucleotide fragments of the invention can be used in particular as probes, especially as capture or detection probes, according to known hybridization techniques.

The probes specific for the genus Rickettsia are especially those having a sequence chosen from the sequences:

- starting at nucleotide No. 181 and ending at nucleotide No. 201
- starting at nucleotide No. 284 and ending at nucleotide No. 298
- starting at nucleotide No. 561 and ending at nucleotide No. 585
- starting at nucleotide No. 940 and ending at nucleotide No. 960
- starting at nucleotide No. 1199 and ending at nucleotide No. 1213
- starting at nucleotide No. 1429 and ending at nucleotide No. 1463 and their complementary sequences, or their analogues.

The probes for the species R. tsutsugamushi are especially those having a sequence chosen from the sequences:

- starting at nucleotide No. 130 and ending at nucleotide No. 170
- starting at nucleotide No. 241 and ending at nucleotide No. 272
- starting at nucleotide No. 299 and ending at nucleotide No. 315
- starting at nucleotide No. 334 and ending at nucleotide No. 357
- starting at nucleotide No. 460 and ending at nucleotide No. 481
- starting at nucleotide No. 504 and ending at nucleotide No. 536
- starting at nucleotide No. 550 and ending at nucleotide No. 570
- starting at nucleotide No. 661 and ending at nucleotide No. 684 starting at nucleotide No. 710 and ending at nucleotide No. 739 starting at nucleotide No. 903 and ending at nucleotide No. 929 starting at nucleotide No. 1035 and ending at nucleotide No. 1055 starting at nucleotide No. 1078 and ending at nucleotide No. 1107 starting at nucleotide No. 1330 and ending at nucleotide No. 1350 starting at nucleotide No. 1361 and ending at nucleotide No. 1387 starting at nucleotide No. 1501 and ending at nucleotide No. 1520 starting at nucleotide No. 1555 and ending at nucleotide No. 1576 and their complementary sequences, or their analogues.

Another subject of the invention is a therapy probe for the treatment of infections caused by bacteria of the genus Rickettsia and especially a therapy probe for the treatment of infections caused by a determined species of Rickettsia, both comprising at least one single-stranded nucleotide fragment as defined above.

Another subject of the invention is a primer for the specific reverse transcription to a DNA sequence complementary to a Rickettsia 16S ribosomal RNA sequence belonging either to a region conserved only in Rickettsia, or to a region specific for the species R. tsutsugamushi; or a primer, especially for the specific amplification of a DNA or RNA sequence complementary or homologous to the sequence of the Rickettsia 16S ribosomal RNA, belonging either to a region conserved only in Rickettsia, or to a region specific for the species R. tsutsugamushi. Such a primer comprises or consists of a single-stranded nucleotide fragment as defined above.

The invention also relates to a reagent for detecting and/or identifying at least one species of Rickettsia in a biological sample comprising at least one probe of the invention, and in particular a capture probe and/or a detection probe corresponding to the definition of a probe given above. The reagent may comprise a mixture of probes.

Finally, the invention provides a process for detecting and/or identifying at least one species of Rickettsia in a biological sample according to which either ribosomal RNA, in particular 16S rRNA, extracted from rickettsias and optionally denatured, or genomic DNA, extracted and denatured, from the bacteria, or alternatively the DNA obtained from the reverse transcription of the 16S ribosomal RNA is brought into contact with at least one probe of the invention, and then the possible hybridization of the said probe is detected in a manner which is known per se.

Of course, it is advisable to carry out the hybridization under conditions which are sufficiently discriminating (stringency) for the hybridization of at least one of the probes to be specific.

If desired, before exposing the nucleic acid to the probe of the invention, this nucleic acid is amplified in the presence of a suitable enzymatic system and of at least one amplification primer of the invention.

The invention relates in particular to a process for the detection and/or identification of Rickettsia in a biological sample, characterized in that it comprises:

a—the bringing of the said sample into contact with at least one single-stranded nucleotide fragment as defined above under predetermined conditions which allow the said fragment to hybridize to the rDNA or rRNA of a bacterium of the genus Rickettsia, if present; and b—the detection of the said hybrid as an indicator of the presence of Rickettsia in the sample.

Of course, the predetermined hybridization conditions are those which allow a specific hybridization.

The following examples illustrate the invention.

EXAMPLE 1

Determination of the nucleotide sequence of the DNA corresponding to the 16S ribosomal RNA of rickettsias. The nucleotide sequence of the DNA corresponding to the 16S ribosomal RNA of the following 16 strains was determined:

| | | |
|---|---|---|
| R. tsutsugamushi | ATCC | Gilliam |
| R. canada | Gamaleya Research Institute Collection 2678 | |
| R. conorii | ATCC | VR-141 |
| R. akari | ATCC | VR-148 |
| R. mooseri | ATCC | VR-144 |
| R. australis | | |
| R. rhipicephali | | |
| R. montana | | |
| R. bellii | | |
| R. japonica | | |
| R. parkeri | | |
| R. helvetica | | |
| R. sibirica | ATCC | VR-151 |
| R. massiliae | | |
| R. slovaca | | |
| R. africae | Gamaleya Research Institute Collection | |

The total DNA of the strains was isolated according to the technique described by Maniatis et al. (Molecular cloning, Cold Spring Harbor, 1982). PCR amplification products were generated from the genomic DNA isolated from these strains with the aid of amplification primers chosen from conserved regions in the known sequences of R. rickettsii, R. typhi and R. prowazekii.

The amplification products obtained were purified on magnetic beads labelled with streptavidin (Dynabead M-280; Dynal Inc., N.Y.) and sequenced using the technique recommended in the commercial kit "Autoread sequencing kit".

EXAMPLE 2

Use of a specific probe directed against the 16S ribosomal RNA for the identification of R. tsutsugamushi. The probe starting at nucleotide No. 903 and ending at nucleotide No. 929 of SEQ ID NO 13 is specific for the R. tsutsugamushi strains. A collection of rickettsia strains was tested by hybridization on the 16S ribosomal RNA and made it possible to observe the specificity of this probe.

The hybridization of the ribosomal RNAs of a target bacterium was performed according to the non-radioactive and semiautomated detection process described in French Patent No. 90 07249 and modified for the detection of ribosomal RNA by the addition of a destabilizer. This destabilizer (which is a capture probe, starting at nucleotide No. 940 and ending at nucleotide No. 970 of the R. tsutsugamushi (referenced 23 in the accompanying figure)) and an oligonucleotide-enzyme detection conjugate (the oligonucleotide corresponding to the probe defined at the beginning of the present example) are used. The operation was performed in a microtitre plate according to the following procedure.

The ribosomal RNA of the strains was extracted according to the basic procedure for the extraction of RNA from Gram-positive bacteria described in "Current Protocols in Molecular Biology" 1987, Ausubel FM et al., Wiley interscience, New York. A solution of 1 ng/µl of the capture oligonucleotide whose 5' end has reacted with the reagent Aminolink 2 (Applied Biosystems, Foster city, California) in 3× PBS (0.45 M NaCl, 0.15 M sodium phosphate pH 7.0), is deposited in a microtitre plate (Nunc 439454). The plate is incubated for 2 h at 37° C. and then washed 3 times with 300 µl of PBST (1× PBS, 0.05% Tween 20 (Merck 822184)). The Aminolink 2 reagent makes it possible to add to the 5' end of the probe an arm comprising a 6-aminohexyl group. The probe thus coupled to a ligand having a polar group (primary amine), and passively attached to the support, provides an enhanced signal; see Application FR 91 09057.

The target consisting of 10 µl of total RNA extract is mixed with 40 µl of PBS-salmon buffer (3× PBS+10 µg/ml of salmon sperm DNA (Sigma D 9156)). The whole mixture is added in the well to 50 µl of a solution of oligonucleotide-peroxidase conjugate, constituting the detection probe, at the concentration of 0.1 ng/µl of oligonucleotide in a PBS-horse buffer (3× PBS +10% horse serum (BioMerieux 55842)). The plate is incubated for 1 h at 37° C. and then washed 3 times with 300 µl of PBST buffer. To each well are added 100 Al of OPD substrate (ortho-phenylenediamine, Cambridge Medical Biotechnology ref/456) in a 0.055 M citric acid, 0.1 M sodium monohydrogen phosphate buffer, pH 4.93) at a concentration of 4 mg/ml, to which hydrogen peroxide at 30%, diluted 1/1000, is added immediately before use. After reacting for 20 min, the enzymatic activity is blocked with 100 µl of 1N sulphuric acid and the reading is carried out on an Axia Microreader apparatus (AXIA : registered trademark) (BioMérieux) at 492 nm.

The target bacteria were especially the following:
30 strains belonging to the order Rickettsiales
20 strains belonging to the genus Rickettsia
7 strains belonging to the species *R. tsutsugamushi*

The specific combination was adapted on the VIDAS automatic machine (registered trademark—marketed by the company BioMérieux-VITEK). The wall of the microplate well is replaced here by the SPR (trademark) (Solid Phase Receptacle) which is a conical support made from a material sold under the name K resin (butadiene-styrene copolymer) and marketed by the company BioMérieux-VITEK (USA). The various reagents are deposited in a strip with several cuvettes and the various stages take place in the SPR which is capable of sucking in and of expelling the reagents and which therefore acts as pipette. The sandwich hybridization reaction described in the procedure below takes place on the inner wall of the cone.

On the inner surface of the SPR is passively attached the capture oligonucleotide comprising at its 5' end the Aminolink 2 ligand (Applied Biosystems-ref. 400808) at a concentration of 1 ng/µl in a volume of 315 µl of a 4× PBS solution (200 mM sodium phosphate pH 7.0, 600 mM NaCl). After one night at room temperature or two hours at 37° C., the cones are washed twice with a PBS-Tween solution and then dried under vacuum. The strip contains, in cuvettes, the reagents necessary for the detection, that is to say: 200 µl of a solution at 0.1 ng/µl of the oligonucleotide-alkaline phosphatase detection conjugate, twice 600 µl of PBS-Tween washing solution and a substrate cuvette.

In the first well of the strip 10 µl of extracted RNA are deposited in the same buffer as for the above microplate procedure.

After incubating the cone for 30 minutes with the target plus detection probe mixture, the cone is washed twice with a PBS-Tween solution. 250 µl of MUP (4-methyl-umbelliferyl phosphate) substrate in solution in a diethanolamine buffer are sucked into the cone and then released into a reading cuvette. The apparatus measures the fluorescent signal, expressed in RFU (relative fluorescence units), of the cuvette.

The results obtained with this system are the same as those obtained in a microplate.

In the same manner, it is possible to verify the specific character of the genus or of the species of other nucleotide fragments which are the subject of the invention.

List and origin of the bacteria whose rDNA sequence corresponding to the 16S rRNA is represented in the annex.

1 *R.rickettsii* (SEQ ID NO: 23) Genbank 14 thai (tick typhus rickettsia) (SEQ ID NO: 24)

10 *R.slovaca* (M-91 isolate different from *R.siberica*) (SEQ ID NO: 25)

11 *R.japonica* (SEQ ID NO: 26)

3 *R.conorii* (SEQ ID NO: 27)

18 astrakan fever rickettsia (SEQ ID NO: 29)

13 israeli tick typhus rickettsia (SEQ ID NO: 29)

7 *R.sibirica* (SEQ ID NO: 30)

15 *R.parkeri (SEQ ID NO:* 31)

16 *R.africae* (SEQ ID NO: 32)

8 *R.massiliae* (SEQ ID NO: 33)

17 Bar29 (GS isolate different from R massiliae) (SEQ ID NO: 34)

6 *R.rhipicephali* (SEQ ID NO: 35)

9 *R.montana* (SEQ ID NO: 36)

12 *R.helvetica* (SEQ ID NO: 37)

4 *R.australis* (SEQ ID NO: 38)

5 *R.akari* (SEQ ID NO: 39)

31 RSDNAX (EBL bacterium) (SEQ ID NO: 40) Genbank

2 *R.bellii* (SEQ ID NO: 41)

21 Coccinelle (AB bacterium) (SEQ ID NO: 42) Genbank

22 *R.canada (SEQ ID NO:* 43)

19 *R.prowazekii* (SEQ ID NO: 44) Genbank

20 *R.typhi* (SEQ ID NO: 45) Genbank

23 *R. tsutsugamushi* (SEQ ID NO: 46)

26 *Cowdria ruminantium* (CRDNA) (SEQ ID NO: 47) Genbank

25 *Ehrlichia chaffeensis* (EHRRRNAF) (SEQ ID NO: 48) Genbank

27 *Anaplasma marginale* (APMRR16SA) (SEQ ID NO: 49) Genbank

28 *Wolbachia pipientis* (WP16SCP) (SEQ ID NO: 50) Genbank

24 *Ehrlichia risticii* (EHRRGBSA) (SEQ ID NO: 51) Genbank

30 Rochalimea (Bartonella)quintana ROCRR16SA (SEQ ID NO: 52) Genbank

29 *Coxiella burnatti* COXRRSA (SEQ ID NO: 53) Genbank

We claim:

1. A single-stranded nucleotide fragment of up to 35 nucleotide units, said fragment being capable of hybridizing to rDNA or rRNA of at least one bacterium of the genus Rickettsia and not hybridizing to non-Rickettsia rDNA or rRNA, wherein said fragment comprises an oligonucleotide selected from the group consisting of:

a) polynucleotide fragments of a range of nucleotides selected from the group of ranges consisting of bases 130 to 170, 181 to 201, 241 to 272, 284 to 298, 299 to 315, 334 to 357, 460 to 481, 504 to 536, 550 to 570,561 to 585, 661 to 684, 710 to 739, 940 to 960, 1035 to 1055, 1078 to 1107, 1199 to 1213, 1330 to 1350, 1361 to 1387, 1429 to 1463, 1501 to 1520 and 1555 to 1576 as numbered in Table 1 of a nucleic acid oligomer selected from the group consisting of SEQ ID NOS: 23–45, and their complementary sequences, analogues of said SEQ ID NOS, and analogues of said complementary sequences, said oligonucleotide having at least eight consecutive nucleotides of said polynucleotide fragments;

b) polynucleotide fragments of a range of nucleotides selected from the group of ranges consisting of bases 130 to 170, 181 to 201, 241 to 272, 284 to 298, 299 to 315, 334 to 357, 460 to 481, 504 to 536, 550 to 570, 561 to 585, 661 to 684, 710 to 739, 940 to 960, 1035 to 1055, 1078 to 1107, 1199 to 1213, 1330 to 1350, 1361 to 1387, 1429 to 1463, and 1555 to 1576 as numbered in Table 1 of a nucleic acid oligomer as set forth in SEQ ID NO: 46, its complementary sequences, analogues of said SEQ ID NO, and analogues of said complementary sequence, said oligonucleotide having at least eight consecutive nucleotides of said polynucleotide fragments; and c) polynucleotide fragments of a range of nucleotides of a range of bases 903 to 929 as numbered in Table 1 of a nucleic acid oligomer selected from the group consisting of SEQ ID NOS: 28 39, 41–43 and 46, and their complementary sequences, analogues of said SEQ ID NOS, and analogues of said complementary sequences, said oligonucleotide having at least ten consecutive nucleotides of said polynucleotide fragments.

2. A single-stranded nucleotide fragment according to claim 1, wherein said oligonucleotide comprises at least ten consecutive nucleotides of said polynucleotide.

3. A single-stranded nucleotide fragment according to claim 1, wherein said non-Rickettsia comprise *Cowdria ruminantium, Ehrlichia chaffeensis, Anaplasma marginale, Wolbachia pipientis, Ehrlichia risticii, Rochalimea quintana* and *Coxiella burnatti.*

4. A single-stranded nucleotide fragment according to claim 1, consisting of said oligonucleotide.

5. A single-stranded nucleotide fragment of up to 35 nucleotides capable of hybridizing to rDNA or rRNA of at least one bacterium of the genus Rickettsia and not hybridizing to non-Rickettsia rDNA or rRNA, comprising an oligonucleotide of at least eight consecutive nucleotides of a polynucleotide selected from the group consisting of SEQ ID NOS: 1–20 and 22, complementary sequences of SEQ ID NOS: 1–20 and 22, analogues of said SEQ ID NOS: 1–20 and 22 and analogues of said complementary sequences of SEQ ID NOS: 1–20 and 22.

6. A single-stranded nucleotide fragment of RNA, comprising a transcription product of an oligonucleotide fragment of DNA according to claim 1.

7. A single-stranded nucleotide fragment of DNA, wherein said fragment is obtained by reverse transcription of an oligonucleotide fragment of RNA according to claim 5.

8. A single-stranded nucleotide fragment of genomic DNA, wherein a transcription product of said fragment is an oligonucleotide fragment of RNA according to claim 5.

9. A probe for identification of bacteria of the genus Rickettsia comprising a probe sequence of eight to thirty-five nucleotide units of a polynucleotide fragment as defined in claim 1.

10. A probe for identification of bacteria of the species *R. tsutsugamushi*, comprising a probe sequence of eight to thirty-five nucleotide units of a polynucleotide fragment as defined in claim 1.

11. A probe according to claim 8, wherein said fragment is selected from the group of polynucleotide fragments of a range of nucleotides consisting of bases 181 to 201, 284 to 298, 561 to 585, 940 to 960, 1199 to 1213 and 1429 to 1463 as numbered in Table 1 and their complementary sequences.

12. A probe according to claim 9, wherein said polynucleotide fragment is selected from the group consisting of SEQ ID NOS: 1, 3, 5, 6, 7, 8, 9, 11, 12, 13, 15, 16, 18, 19 and 22 and their complementary sequences.

13. A therapy probe for treatment of infection caused by the genus Rickettsia or by a determined species of rickettsias, comprising a nucleotide fragment according to claim 1.

14. A primer for specific reverse transcription of a 16S ribosomal RNA sequence of Rickettsia, said sequence belonging to a region uniquely conserved among rickettsias, comprising a nucleotide fragment according to claim 1.

15. A primer for specific enzymatic amplification of a DNA or RNA sequence complementary or homologous to a sequence of a 16S ribosomal RNA of Rickettsia, comprising a nucleotide fragment according to claim 1.

16. A reagent for detecting or identifying at least one species of Rickettsia in a biological sample, comprising at least one single-stranded nucleotide fragment according to claim 1.

17. A reagent according to claim 16, wherein said nucleotide fragment is attached to a solid support.

18. A reagent according to claim 16, wherein said nucleotide fragment is labelled.

19. A reagent according to claim 16, wherein said at least one probe comprises at least one primer selected from the group consisting of a primer for specific reverse transcription of a 16S ribosomal RNA sequence of Rickettsia, said RNA sequence belonging to a region uniquely conserved among rickettsias, and a primer for specific enzymatic amplification of DNA or RNA complementary or homologous to a sequence of a 16S ribosomal RNA of Rickettsia.

20. A process for detection or identification of Rickettsia in a biological sample, comprising:
 a. bringing said sample into contact with at least one single-stranded nucleotide fragment as defined in claim 1, under predetermined conditions which allow the fragment to hybridize to rDNA or rRNA of a bacterium of the genus Rickettsia, if present, to form a hybrid; and
 b. detecting said hybrid.

21. A process for detection or identification of at least one species of the genus Rickettsia in a biological sample, comprising:
 a. extracting 16S ribosomal RNA from bacteria contained in the said sample to form an analyte;
 b. contacting said analyte with at least one probe as defined in claim 9, and
 c. detecting possible hybridization of the said probe.

22. A process for detection or identification of at least one species of the genus Rickettsia in a biological sample, comprising:
 a. extracting and denaturing genomic DNA from bacteria contained in the said sample to form a denatured analyte;
 b. contacting said denatured analyte with at least one probe as defined in claim 9; and
 c. detecting possible hybridization of said probe to said denatured analyte.

23. A process for detection or identification of a species of the genus Rickettsia in a biological sample, comprising:
 a. obtaining DNA by reverse transcription of 16S ribosomal RNA of bacteria contained in said sample;
 b. contacting said DNA with at least one probe as defined in claim 9; and
 c. detecting possible hybridization of said probe to said DNA.

24. A process according to claim 21, further comprising amplifying said RNA or reverse transcripts thereof contained in said analyte in the presence of an enzymatic amplification system having at least one primer selected from the group consisting of a primer for a specific reverse transcription of a 16S ribosomal RNA sequence of genus Rickettsia, said sequence belonging to a region uniquely conserved among Rickettsia, and a primer for specific enzymatic amplification of a DNA or RNA sequence complementary or homologous to a sequence of a 16S ribosomal RNA of Rickettsia to form said analyte, then contacting the amplified nucleic acid to said probe.

25. A single-stranded nucleotide fragment according to claim 1, capable of distinguishing non-Rickettsia from Rickettsia selected from the group consisting of *R. tsutsugamushi, R. canada, R. conorii, R. akari, R. mooseri, R. australis, R. rhipicephali, R, montana, R. bellii, R. japonica, R. parkeri, R. helvetica, R. sibirica. R. massiliae, R. slovaca* and *R. africae.*

26. A single-stranded nucleotide fragment of up to 35 nucleotide units, said fragment being capable of hybridizing to rDNA or rRNA of at least one bacterium of the genus Rickettsia and not hybridizing to non-Rickettsia rDNA or rRNA, wherein said fragment comprises an oligonucleotide of at least ten consecutive nucleotides of a polynucleotide selected from the group consisting of polynucleotide fragments of a range of nucleotides selected from the group of ranges consisting of:
 bases 130 to 170, 181 to 201, 241 to 272, 284 to 298, 299 to 315, 334 to 357, 460 to 481, 504 to 536, 550 to 570, 561 to 585, 661 to 684, 710 to 739, 903 to 929, 940 to 960, 1035 to 1055, 1078 to 1107, 1199 to 1213, 1330 to 1350, 1361 to 1387, 1429 to 1463, 1501 to 1520 and 1555 to 1576 as numbered in Table 1 of a nucleic acid oligomer selected from the group consisting of SEQ ID NOS: 28, 39,41,42 and 43, and their complementary sequences;

bases 130 to 170, 181 to 201, 241 to 272, 284 to 298, 299 to 315, 334 to 357, 460 to 491, 504 to 536, 550 to 570, 561 to 585, 661 to 684, 710 to 739, 940 to 960, 1035 to 1055, 1078 to 1107, 1199 to 1213, 1330 to 1350, 1361 to 1387, 1429 to 1463, 1501 to 1520 and 1555 to 1576 as numbered in Table 1 of a nucleic acid oligomer selected from the group consisting of SEQ ID NOS: 23–27, 29–38, 40, 44, and 45, and their complementary sequences; and bases 130 to 170, 181 to 201, 241 to 272, 284 to 298, 299 to 315, 334 to 357, 460 to 491, 504 to 536, 550 to 570, 561 to 585, 661 to 684, 710 to 739, 903 to 929, 940 to 960, 1035 to 1055, 1078 to 1107, 1199 to 1213, 1330 to 1350, 1361 to 1387, 1429 to 1463 and 1555 to 1576 as numbered in Table 1 of a nucleic acid oligomer SEQ ID NO: 46, and its complementary sequence.

27. A single-stranded nucleotide fragment of up to 35 nucleotide units capable of hybridizing to rDNA or rRNA of at least one bacterium of the genus Rickettsia and not hybridizing to non-Rickettsia rDNA or rRNA, comprising an oligonucleotide of at least 10 consecutive nucleotides of a polynucleotide selected from the group consisting of SEQ ID NOS: 1–20 and 22, and complementary sequences thereof.

* * * * *